United States Patent [19]
Maeno

[11] Patent Number: 5,619,232
[45] Date of Patent: Apr. 8, 1997

[54] MAINTENANCE STATION OF INK JET PRINTER AND CAP AND PUMP INCLUDED THEREIN

[75] Inventor: Fumio Maeno, Saitama-ken, Japan

[73] Assignee: Citizen Watch Co., Ltd., Tokyo, Japan

[21] Appl. No.: 307,628

[22] PCT Filed: Dec. 15, 1993

[86] PCT No.: PCT/JP93/01820

§ 371 Date: Sep. 20, 1994

§ 102(e) Date: Sep. 20, 1994

[87] PCT Pub. No.: WO94/13488

PCT Pub. Date: Jun. 23, 1994

[30] Foreign Application Priority Data

| Dec. 16, 1992 | [JP] | Japan | 4-354453 |
| Jul. 2, 1993 | [JP] | Japan | 5-190898 |
| Sep. 1, 1993 | [JP] | Japan | 5-239239 |
| Sep. 28, 1993 | [JP] | Japan | 5-263033 |

[51] Int. Cl.⁶ ................................ B41J 2/165
[52] U.S. Cl. ............................ 347/30; 417/464
[58] Field of Search .................. 347/22, 30, 31, 347/32; 417/415, 464, 510

[56] References Cited

U.S. PATENT DOCUMENTS

| 4,577,203 | 3/1986 | Kawamura | 347/30 |
| 4,800,403 | 1/1989 | Accattino et al. | 347/30 |
| 5,086,305 | 2/1992 | Terasawa | 347/30 |

FOREIGN PATENT DOCUMENTS

| 352866 | 12/1905 | France | 415/464 |
| 2460 | of 1883 | United Kingdom | 415/464 |

Primary Examiner—John E. Barlow, Jr.
Attorney, Agent, or Firm—Wenderoth, Lind & Ponack

[57] ABSTRACT

An ink jet printer includes a maintenance station which is simple in construction and small-sized. A cap holder is provided with a suction port communicating with a cap through a communication hole, a discharge port and a vent port. Provided in the cap holder is a cylinder which rotates upon actuation of a piston and which is provided on an outer diameter portion thereof with connection holes such that a pressure chamber is connected to the suction port in a suction stroke, the pressure chamber is connected to the discharge port and the suction port is connected to the vent port in an exhaust stroke. The cap holder contains therein the vent port for a suction pump and an atmospheric opening valve.

66 Claims, 37 Drawing Sheets

MAINTENANCE STATION OF INK JET PRINTER AND CAP AND PUMP INCLUDED THEREIN

BACKGROUND OF THE INVENTION

The present invention relates to an ink jet printer for printing by jetting ink droplets, and more particularly relates to a maintenance station employed therewith to cap and apply suction to a nozzle of an ink jet head in order to achieve and maintain printing quality.

Non-impact recording methods recently have been employed because printing noise is reduced and such methods are suitable for color printing. Many new ink jet printers employ such methods and provide high speed recording and can be employed to be an ordinary paper. Drop-on-demand type ink jet printers widely are used as output equipment of personal computers because means for recovering waste ink are unnecessary and because such type printer can be miniaturized and of simple structure. This type of ink jet printer may be divided roughly into the heat machine transformation type and the electric machine transformation type.

The heat machine transformation type has an electric circuit mounted along the path of liquid passing to a nozzle. Ink is ejected by steam pressure on applying electric current and heat. This type of ink jet printer is suitable for miniaturization. However, scorching can occur over long periods of use. Therefore, special ink must be used to prevent such scorching.

The electric machine transformation type uses deformation occurring by applying an electric field to energy supply means in the form of a piezoelectric element. Use is not limited to a particular ink and this ink which is most suitable to obtain quality printing for a particular use can be employed. This type printer however requires a large space for the energy supply means and therefore is not suitable for miniaturization.

For resolving this problem, an ink jet for supplying energy to liquid by deformation of a side wall by utilizing electric deformation of a shear mode type is shown in Japanese Laid Open Patent Application 150355/1990. The most important feature is to give eject energy to liquid by deformation of a side wall which opens to a nozzle. Therefore, liquid paths may be arranged in a plane with an interval between nozzles.

In such ink jet printer, when an ink jet head is changed, when the printer is started after a long period of time, or when printing quality is reduced during printing, old ink is exhausted from the ink jet head by applying suction to a nozzle hole from a rubber cap pressed to a face of a plate of the nozzle. The circumference of the cap is pressed against the nozzle plate to seal the interior of the cap. At such time, an interior volume of the cap is reduced. Since air flows in the ink jet head from a nozzle hole, the cap interior is opened to the atmosphere in advance to eject a droplet. Next, the cap interior is shut off from the atmosphere for suctioning the ink jet head through the cap by a pump under airtight conditions. When the cap is detached from the nozzle plate, the cap interior is opened to the atmosphere to prevent a pressure drop therein. A pressure drop in the cap interior would cause poor election of an ink droplet because ink passing from the nozzle would adhere to the surface of the nozzle plate.

Therefore, such a maintenance station which is used for recovering ink quality includes a cap, an atmosphere opening valve, a pump, cams for driving such elements and a vacuum pipe. Such construction is complicated.

A maintenance station disclosed is Japanese Laid Open Patent Application 87267/1991 is shown in FIG. 56 and includes a pump carriage 50 slidable in opposite directions. When a printer head carriage moves to the left as shown and contacts a carriage arm 51, it moves while pressing the pump carriage 50. A cap 52 moves along a first rail 54 and covers a nozzle. An atmosphere opening valve 53 is installed at a back surface of the pump carriage 50. The atmosphere opening valve 53 moves to the left on opening state when touched to a second rail 55. When the pump carriage 50 stops at the end of a stroke, an atmosphere opening valve cam 56 rotates second rail 55 apart from the atmosphere opening valve 53 and the valve is shut by action of a spring. First and second pump cams 57, 58 run a suction pump 59 and make a vacuum condition. Cap 52 and an ink jet head are suctioned through a suction tube 60 connected between the suction pump 59 and the cap 52. Such conventional maintenance station has to include an arrangement of the cap, the atmosphere opening valve, the suction pump, the cams for moving such parts and the vacuum tube. Therefore, such construction is complicated and miniaturization is not easy.

The object of the present invention is to remove such defects and to provide a small maintenance station having a simple construction.

BRIEF DESCRIPTION OF THE DRAWINGS

FIGS. 50(a) and 59(b) are similar views but with the cap holder just before a second reverse rotation of the cam;

DETAILED DESCRIPTION OF THE INVENTION

Figure 1:
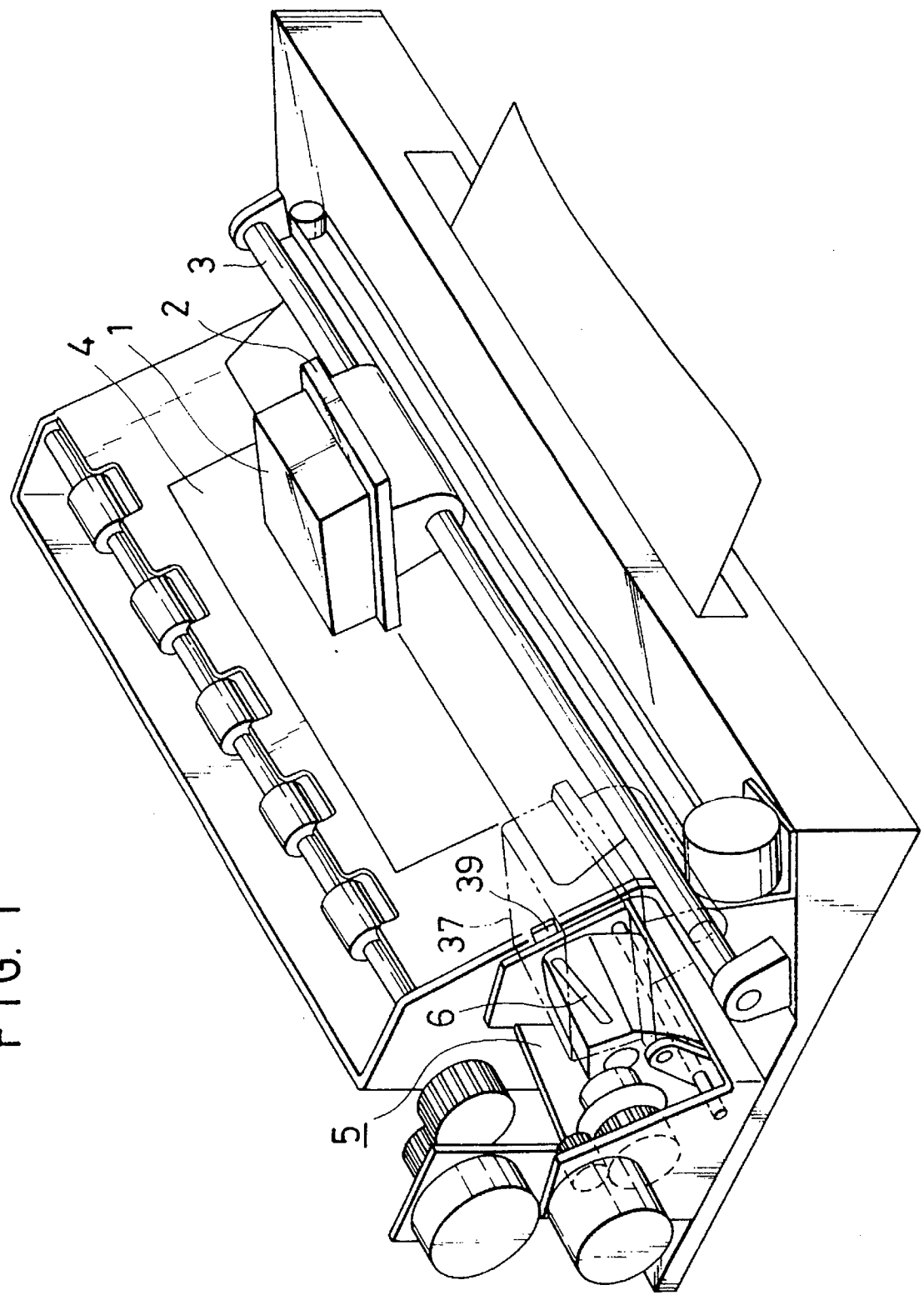
FIG. 1 is a perspective view of an ink jet printer having a maintenance station according to the present invention.

FIG. 1 is a perspective view of an ink jet printer having a maintenance station 5 according to a first embodiment of the present invention. Plural nozzle holes of an ink jet heat 1 face a paper sheet 4. The ink jet head 1 is mounted on a carriage 2 which is movable in opposite directions on a guide rod 3. The ink jet head may be positioned precisely by a motor. The paper sheet 4 may be moved up and down precisely. Ink is ejected from the nozzle holes to print letters and figures by controlling the relative position between the paper sheet 4 and ink jet head 1. The maintenance station 5 is installed outwardly of a side of a printing area of head 1. A home position 37 is a position of the carriage 2 at which a nozzle plate 35 of the ink jet head 1 (FIG. 5) is positioned at the front of a cap 6 of the maintenance station 5 when the head is to be capped.

Figure 2:
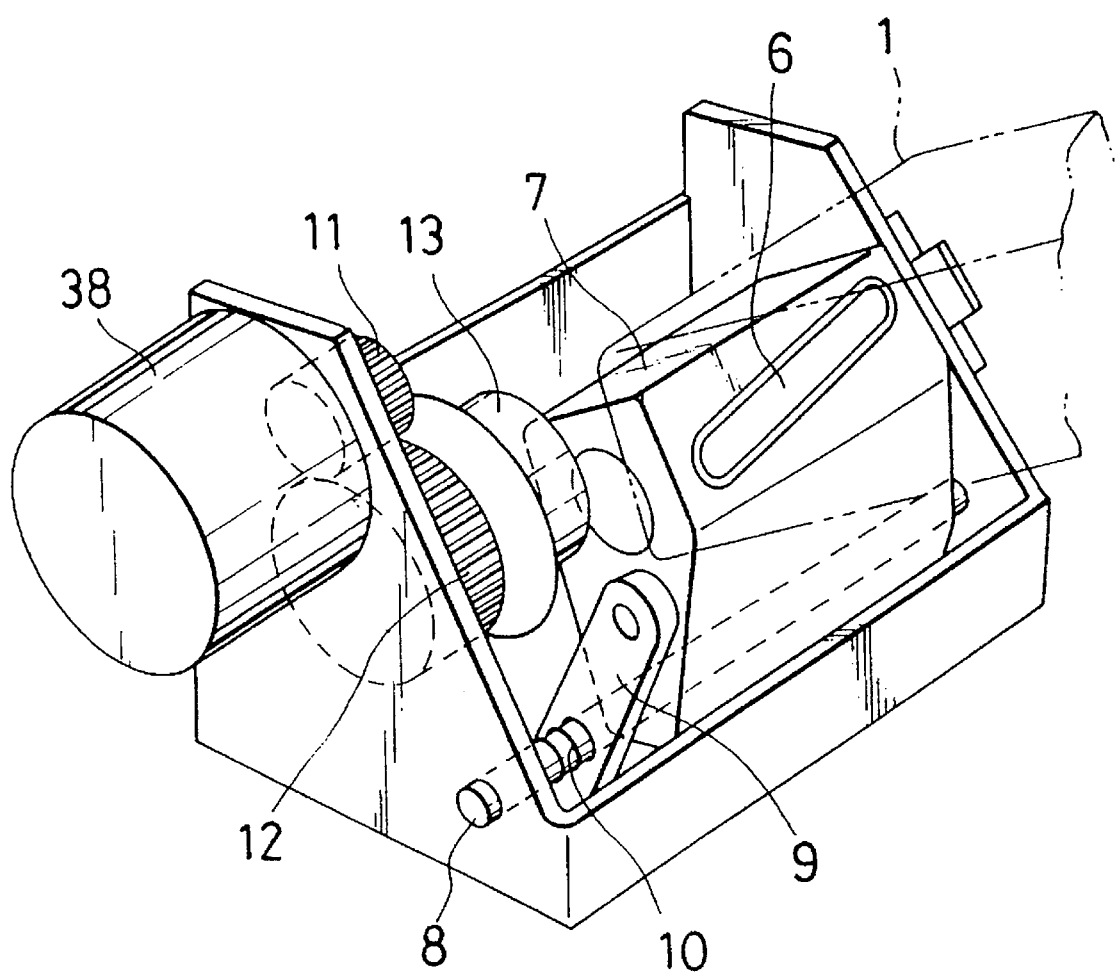
FIG. 2 is a perspective view of the maintenance station according to a first embodiment of the present invention.
Figure 3:
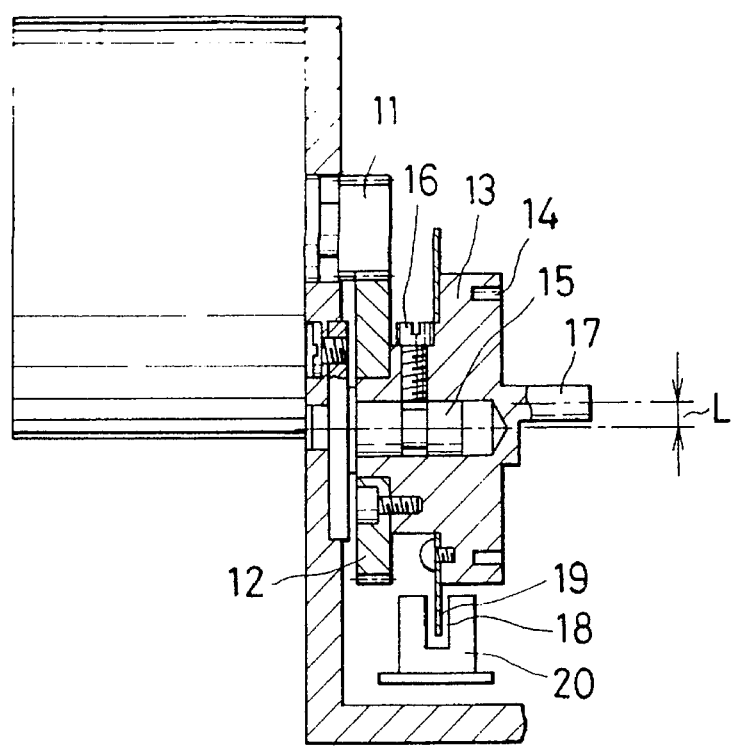
FIG. 3 is a sectional view of a cam portion of the first embodiment of the present invention.
Figure 4:
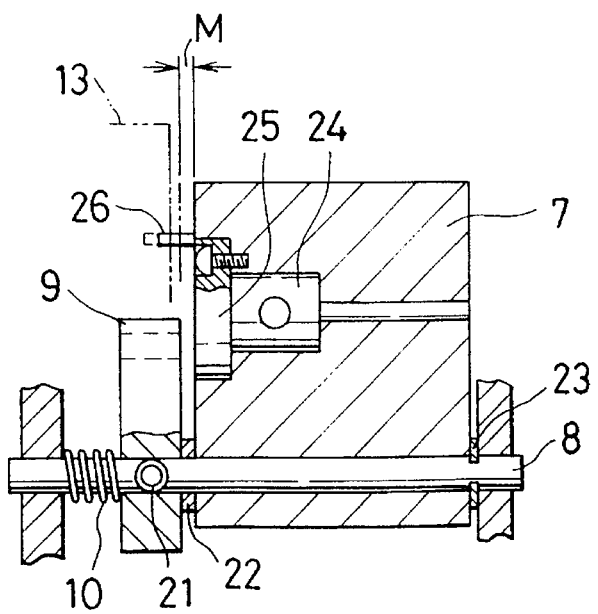
FIG. 4 is a sectional view of a cap holder of the first embodiment of the present invention.
Figure 5:
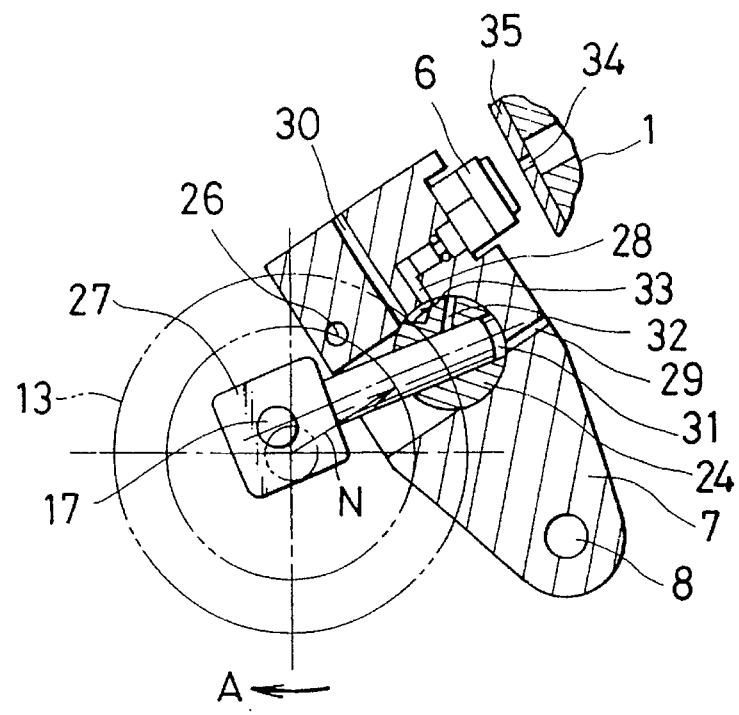
FIG. 5 is a sectional view at a starting point of a cam of the first embodiment.

FIG. 2 is a perspective view of the maintenance station 5. A cap holder 7 supporting cap 6 is mounted on a guide shaft 8. A stop 9 and a pressing spring 10 are mounted on the guide shaft 8. A small gear 11 mounted on the output shaft of a motor 38 engages with a gear 12 that is rigid with a cam 13. Rotation of motor 38 controls rotation of the cam 13 through the small gear 11 and the gear 12. A cam groove 14 is formed at the end surface of the cam 13, and a cam follower 26 of the cap holder 7 extends into the cam groove 14 (FIGS. 3 and 4). By increase and decrease of the radius of the cam groove 14, the cap holder 7 swings or pivots about the guide shaft 8 as a center and moves away from and toward a nozzle plate 35 of the ink jet head 1 (FIG. 5). When the cap holder moves away from the ink jet head 1, head 1 then is movable to the right and left along guide rod 3, since the cap 6 is spaced fully from the nozzle plate 35. When the ink jet head 1 is located at the home position 37, the cap 6 caps the nozzle holes by moving with the cap holder 7 toward head 1, due to rotation of the cam 13. Stopper 9 is located precisely on the guide shaft 8 to determine the capping position exactly. When the ink jet head 1 moves towards the home position, a side face of the carriage 2 presses the spring 10 at the front of the home position 37 and the ink jet head 1 moves to the home position 37 to align with cap holder 7.

FIG. 3 is a sectional view of the cam 13. A cam supporting shaft 15 is fixed on a side wall of the maintenance station 5. Cam 13, a glare protection or light shielding plate 18 and gear 12 are mounted rotatably on the cam supporting shaft 15. A thrust pin 16 screwed into cam 13 extends into a groove of the cam supporting shaft 15 for preventing cam 13 from moving axially of shaft 15. Cam groove 14 and an eccentric shaft 17 are on a face or side of the cam 13. Eccentric shaft 17 is offset by a distance L from the center of rotation of the cam 13. A hole 19 is formed in the glare protection plate 18. When the cam 13 is positioned at a starting point, the glare protection plate 18 is positioned at an optical axis of an optical sensor 20. When the cam 13 rotates to a position corresponding to a middle point of a closing stroke of a piston 27 (to be discussed below), the optical sensor 20 generates a signal.

FIG. 4 is a sectional view of the cap holder 7. Guide shaft 8 is mounted on a frame of the maintenance station 5. A stop ring 23 is mounted in a groove at an end of shaft 8. Cap holder 7, a spacer 22, stop 9 and pressing spring 10 are mounted in that order on shaft 8. The stop ring 23 abuts the frame. Stop 9 is fixed on the guide shaft 8 by a stopper screw 21. Thus, spring 10 does not act on cap holder 7. Cap holder 7 has sufficient clearance at opposite ends thereof to be rotatable about the guide shaft 8 as a center axis. A cylinder 24 is mounted in the cap holder 7 and fixed by a cover 25. Cam follower 26 is mounted on a side of the cap holder. The cam follower 26 is inserted slidably in the cam groove 14 of the cam 13. When the carriage 2 meets with the stop 9 and moves the stop 9 a distance M, the carriage 2 is stopped at the home position 37, and the cap holder 7 also moves the distance M. The cam follower 26 moves by the same distance further into the cam groove 14. Thus, the cam groove 14 is formed to be deeper than M.

FIG. 5 is a sectional view of the cap holder 7. The cam 13 and eccentric shaft 17 are rigid. A piston 27 is mounted on the eccentric shaft 17, and cam follower 26 is fixed on a side of the cap holder 7. When the cam is rotated such that the radius of the cam groove 14 is increased, the cap holder 7 rotates about the guide shaft 8. Cylinder 24 is rotatably fitted into the cap holder 7. One end of the piston 27 is fitted onto the eccentric shaft 17 and another end of the piston 27 is fitted into the cylinder 24.

A pressure chamber 31 is formed in the cap holder 7 by the piston 27 and cylinder 24. When the eccentric shaft 17 rotates, the piston 27 reciprocates in the cylinder 24, into and from chamber 31. This reciprocation creates suction and compression conditions in the pressure chamber 31 and also pivots or rocks the cylinder 24 about the axis thereof. When cam 13 rotates in the direction of arrow A to a lower dead center point from a upper dead center point, the piston 27 withdraws from the creates suction in the pressure chamber 31. This is called a suction stroke. When the cam rotates to the upper dead center point from the lower dead center point, the piston 27 moves into and creates compression in the pressure chamber 31. This is a compression stroke.

The above movement causes reciprocating rotation of the cylinder 24. An exhaust port 29 which connects with the pressure chamber 31 only during the compression stroke is formed in the cap holder 7. Cap 6 is connected to a suction port 28 formed in the cap holder. When the piston 27 is positioned near the end of suction stroke (FIG. 9), a connecting hole 32 formed in the cylinder 24 connects between suction port 28 and pressure chamber 31. Such connection stops upon start of the compression stroke. An atmosphere port 30 is formed in the cap holder 7 and a connecting hole 33 is formed on the cylinder 24 connects port 30 to the suction port 28 near the center of the compression stroke.

Operation of the maintenance station of the above structure now will be described with reference to FIG. 5 to 11.

FIG. 5 shows the cap holder 7, cam 13 and eccentric shaft 17 in the home position. In such position, the hole 19 of the light shielding plate 18 is aligned with the optical axis of the optical sensor 20. The cam holder 7 is retracted about shaft 8 from head 1, with cap 6 separated from the nozzle plate 35. The piston 27 is in the middle of the compression stroke. The pressure chamber 31, which is defined by the cylinder 24 and the piston 27, is in communication with the discharge port 29. The cam groove 14 along which the cam follower 26 slides has a radius of N. As cam 13 is rotated in the direction of arrow A so that the radius of the cam groove 14 increases, the cap holder 7 is rotated around the guide shaft 8 so that the cap 6 approaches toward the nozzle plate 35. When the cap 6 is brought into contact with the nozzle plate 35, the suction or intake port 28 is connected with the connecting recess or hole 33 and is in communication with the air port 30 through the connection hole 33. That is a capping condition.

Figure 6:
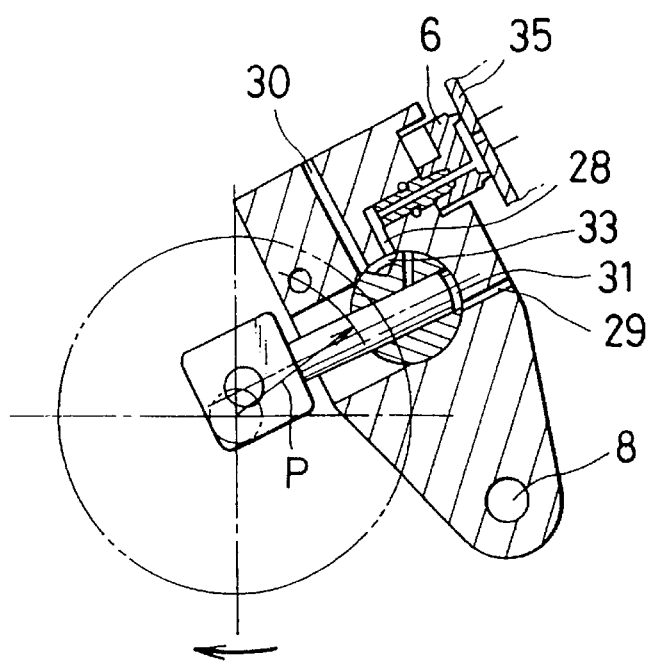
FIG. 6 is a similar sectional view showing the cap holder open to the atmosphere.

FIG. 6 shows the cap holder 7 when it is in the capping and idling discharge condition. Under this condition, the radius of the cam groove 14 becomes P and the cap holder 7 is advanced until the cap 6 is in contact with the nozzle plate 35. The intake port 28 is connected with the connecting hole 33 so that it is in communication with the air port 30 via the connecting hole 33. The pressure chamber 31 is in communication with the discharge port 29.

Figure 7:
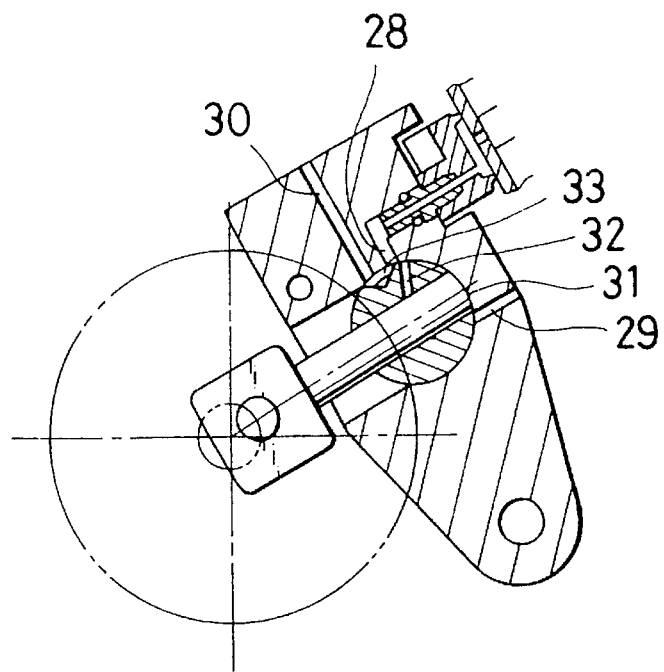
FIG. 7 is a similar sectional view showing the cap holder in a capping state.

FIG. 7 shows the section of the cap holder 7 when it is in the capping condition. The cam groove 14 has a radius of P. The cap 6 is in contact with the nozzle plate 35. The connecting hole 33 separates from the intake port 28 but connecting hole 33 is close thereto. The cap 6 is shielded from the atmosphere.

Figure 8:
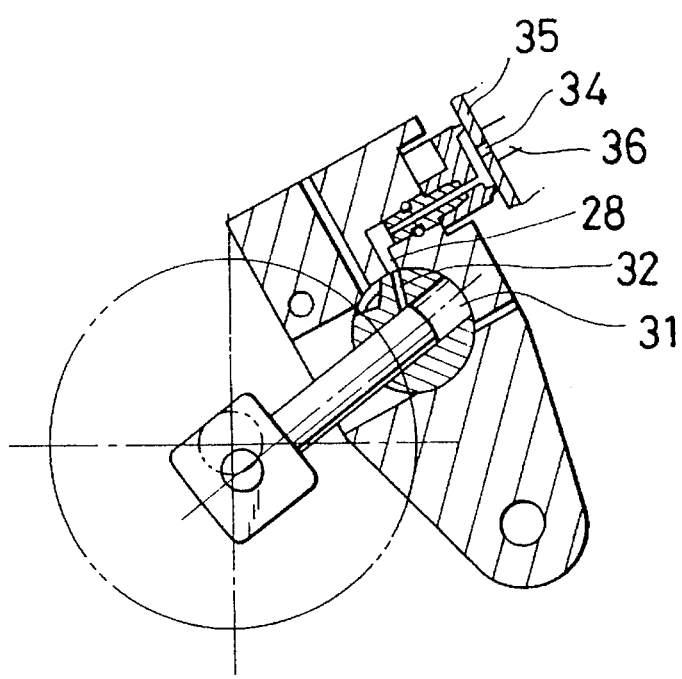
FIG. 8 is a similar sectional view of the cap holder at the start of suction.

FIG. 8 shows a sectional view of the cap holder when the piston is retracted to evacuate the pressure chamber 31 in the course of the intake or suction stroke so that the connecting hole 32 is connected with the pressure chamber 31. The cam groove 14 has a radius of P. The cap 6 is in contact with the nozzle plate 35. The cylinder 24 has passed through a turning point of the intake stroke in the reciprocal movement. The connecting hole 32 which is connected with the intake port 28 is brought into communication with the pressure chamber 31. When the cam 13 is rotated, the communication between the intake port 28 and the connecting hole 32 is interrupted at the lower dead center point. The cam does not stop, but passes through this point. Rotation of the cam is stopped while the intake port 28 is in communication with the pressure chamber 31. After sufficient ink is withdrawn by suction, the next stroke begins.

Figure 9:
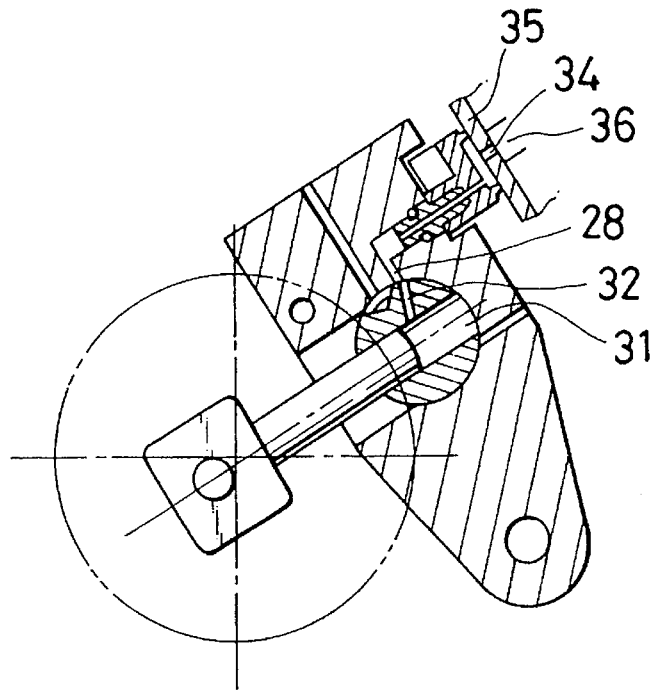
FIG. 9 is a similar sectional view of the cap holder stopped at a center point of suction.

FIG. 9 shows a section of the cap holder when it is stopped in the stop position in the intake stroke. The cam groove 14 has a radius of P. The cap 6 is in contact with the nozzle plate 35. The intake port 28 is in communication with the pressure chamber 31 via the connecting hole 32. Thus, the ink 36 can be withdrawn by the vacuum pressure in the pressure chamber 31.

Figure 10:
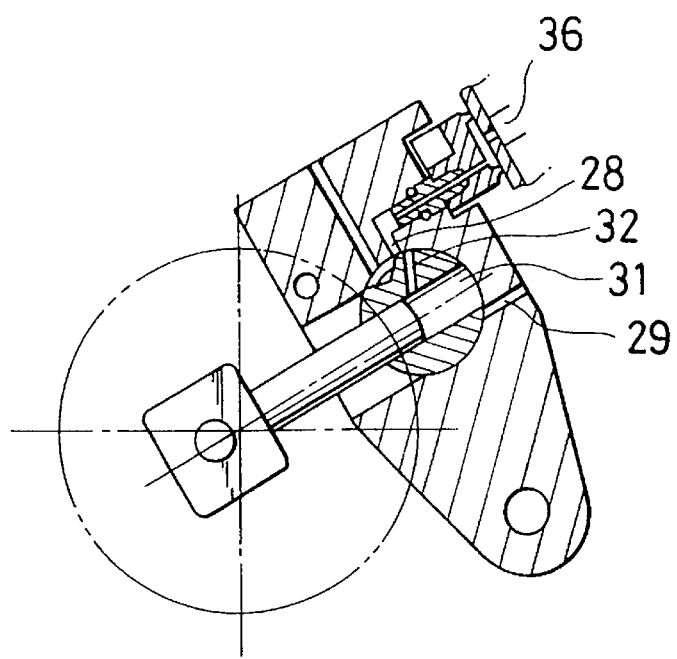
FIG. 10 is a similar sectional view of the cap holder at a dead point of a piston.

FIG. 10 shows a section of the cap holder in the lower dead center point. The intake port 28 is not connected with the connecting hole 32. The pressure chamber 31 is in a condition immediately before it is connected with the discharge port 29.

Figure 11:
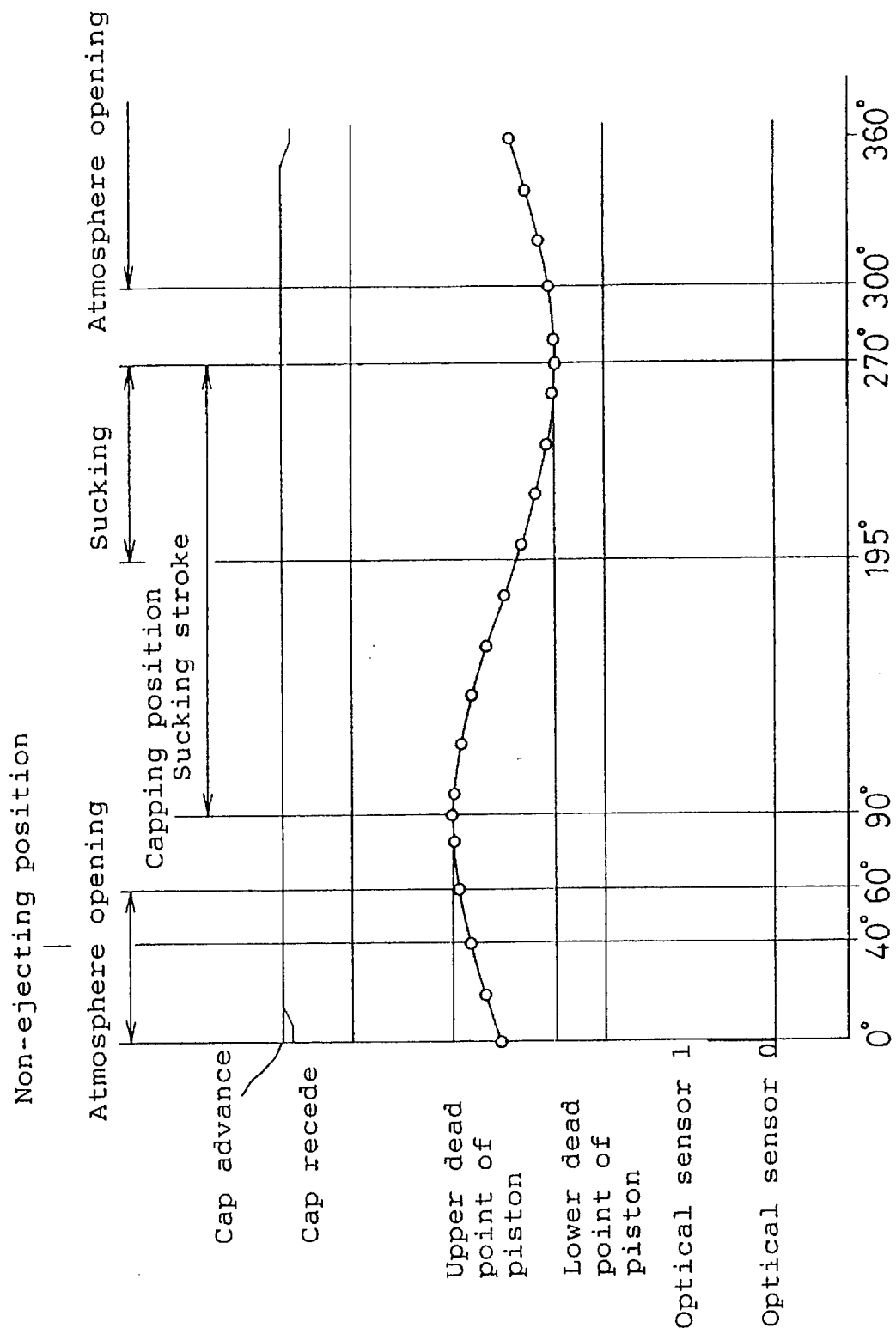
FIG. 11 is a graph of operation of the piston and cam of the maintenance station according to the first embodiment.

FIG. 11 is a cam trace diagram showing the connection between the intake port 28 and the air port 30 and the extension and the retraction of the cap 6, changes in position of piston 27 in association with rotation of the eccentric shaft 17 and turning on or off of the optical sensor 20. The optical sensor 20 generates a turn-on signal only when it is in the home position. At this time, the cap 6 is retracted. As the cam 13 is rotated, the cap 6 is moved forwardly until it reaches the maximum radius position corresponding to the capping position. At this time, the cap 6 is in communication with the air port 30. Communication with the atmosphere last until a 60° position. 40° corresponds to an idling discharge position. At 90°, the cap 6 is shielded again and is in communication with the atmosphere again at 300°. The cap is retracted to the home position. The cam diagram does not illustrate the actual sequence of the maintenance station. The driving method is adopted so that the piston advances, for example, 0° to 60° for performing idling discharge and reverses 60° to 0° to end the stroke, depending upon the printer condition. A conventional ink jet printer comprises a cap, a cap holder, an air release valve, an intake pump and a cam of the maintenance station used for maintaining good print quality, individually provided. Therefore, the conventional printer is very complicated in structure. In contrast, the present invention provides an ink jet printer with a maintenance station which is compact in structure and is capable of positively operating since the pump is incorporated within the cap holder.

Figure 12:
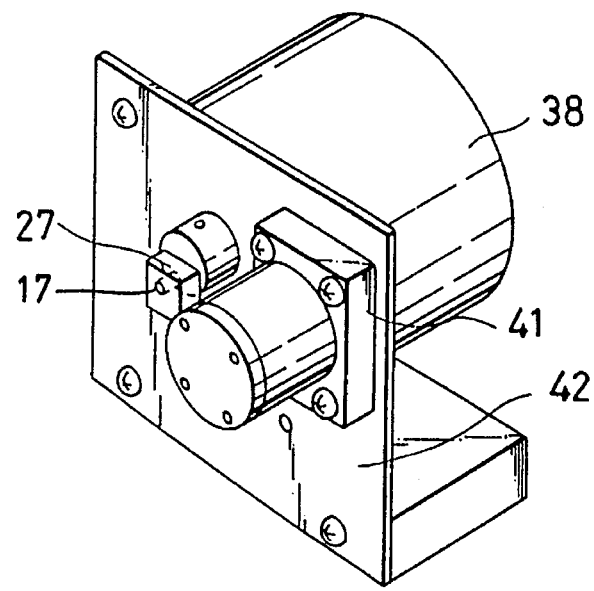
FIG. 12 is a perspective view of a pump of a second embodiment.
Figure 13:
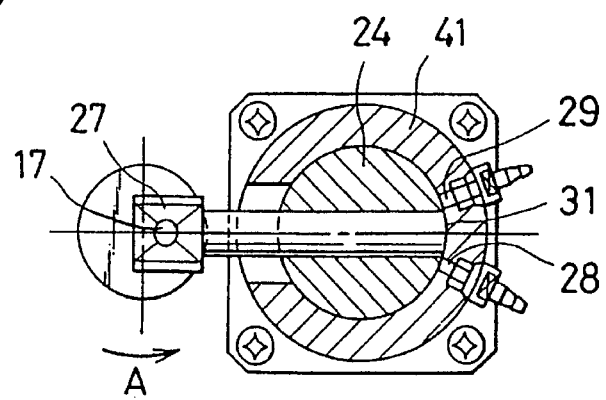
FIG. 13 is a sectional view at an upper dead point of the pump of the second embodiment.
Figure 14:
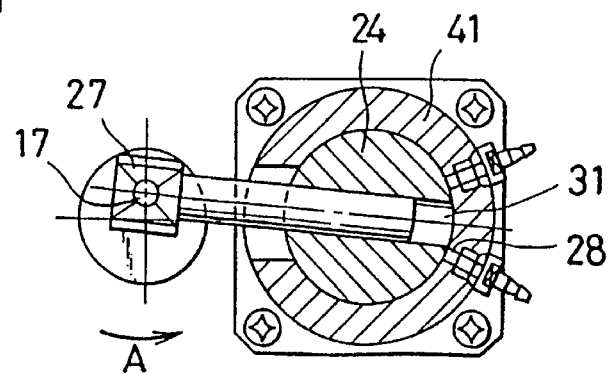
FIG. 14 is a sectional view showing an eccentric shaft of the pump of the second embodiment rotated 90°.
Figure 15:
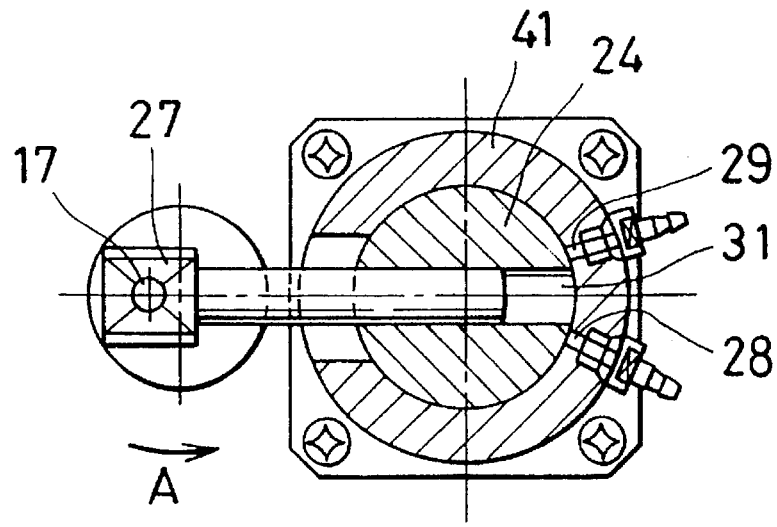
FIG. 15 is a similar sectional view showing the eccentric shaft rotated 180°.
Figure 16:
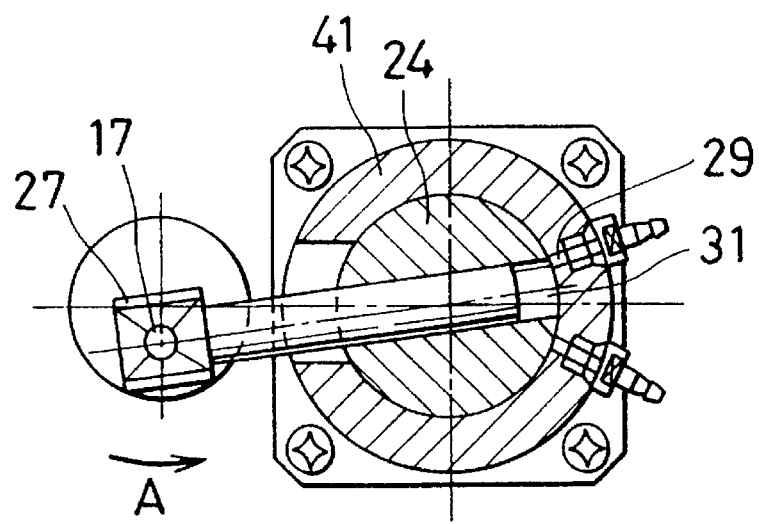
FIG. 16 is a similar sectional view showing the eccentric shaft rotated 270°.

FIG. 12 is the perspective view showing the outward appearance of a pump of a second embodiment of the present invention. A casing 41 and motor 38 are disposed on attachment board 42. An eccentric shaft 17 is attached to the motor 38 and a piston 27 is attached to the eccentric shaft 17. FIG. 13 is a sectional view of the pump. The piston 27 is inserted so as to be able to slide in a cylinder 24 disposed in the casing 41. The piston 27 is driven by the eccentric shaft 17. In FIG. 13 the piston 27 is shown at an upper dead center point and the volume of pressure chamber 31 is at a minimum. An intake or absorption port 28 and an exhaust port 29 are disposed adjacent to the pressure chamber 31. As the eccentric shaft rotates in the direction of arrow A, the piston 27 moves into the intake or absorbing condition or stroke. FIG. 14 shows a sectional view of the pump after the eccentric shaft is rotated by 90° in the direction of arrow A. The piston 27 slides in the cylinder 24 to increase the volume of the pressure chamber 31, and the pressure chamber 31 and the intake or absorption port 28 become connected so that ink can be absorbed through the absorption port. FIG. 15 shows a sectional view of the pump after the eccentric shaft 17 is rotated by 180° in the direction of the arrow A. When the piston 27 slides in cylinder 24 to reach to the lower dead center point, the volume of the pressure chamber 31 reaches a maximum. The cylinder 24 rotates at the same time to interrupt the connection between the absorption or intake port 28 and the pressure chamber 31. FIG. 16 shows a sectional view of the pump after the eccentric shaft 17 is rotated by 270° in the direction of the arrow A. The piston 27 slides in the cylinder 24 so as to compress the volume of the pressure chamber 31. The pressure chamber 31 and the exhaust or discharge port 29 are connected at the same time so that ink flows out of the exhaust port 29. According to the so constructed pump, even if the ink becomes dry and solid as it has not been used for a long period of time, a pump which is suitable for absorbing and exhausting liquid containing solid substance can be realized, unlike the conventional pump wherein the valve will not close if a lump of ink is positioned between the valve and the valve seat.

A third embodiment of the present invention now will be described. The structure and operation of the ink-jet printer provided with the maintenance station of this embodiment is the same as that of the first embodiment and thus will be described referring to FIG. 1. A nozzle plate 35 having a plurality of nozzle holes is on the side of an ink-jet head 1 facing a paper sheet 4. The ink-jet head 1 is disposed on the carriage 2 which moves to the right and left on the guide rod 3. Head 1 can be positioned precisely by a motor. Paper sheet 4 is positioned accurately in the vertical direction, and ink is jetted from the nozzle holes for printing out characters or symbols by controlling the relative positions of the paper sheet 4 and the ink-jet head 1. A maintenance station 5 is provided outwardly of the printing area, and a cap 6 is disposed thereat. The position of the carriage 2 where the nozzle slot of the ink-jet heat 1 is located at the front of the cap 6 is the home position. A wiper 39 is provided at the side of the home position 37 for wiping the nozzle plate every time the ink jet head 1 is moved from the home position 37 to the printing position and from the printing position to the home position 37.

Figure 17:
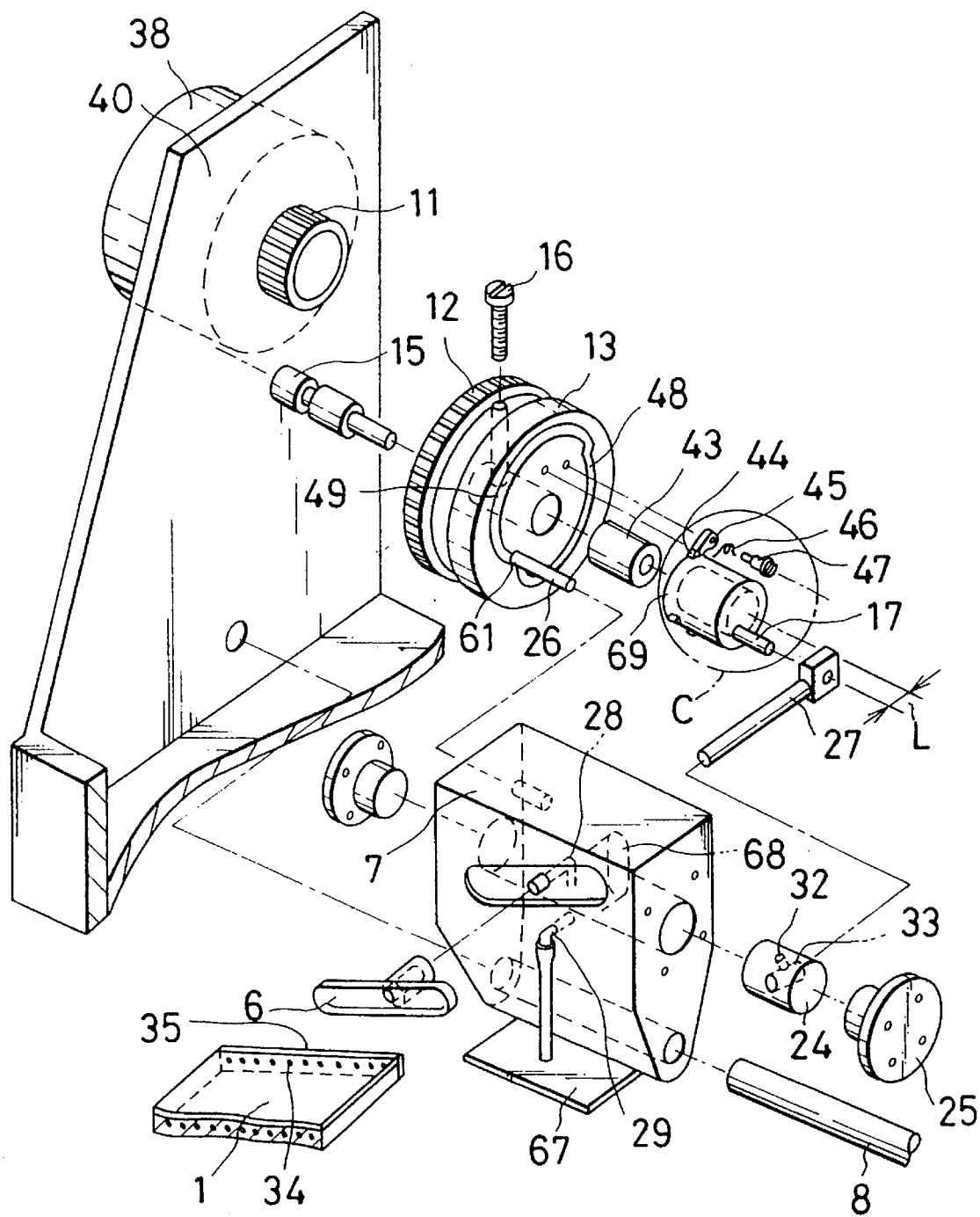
FIG. 17 is a perspective view of a maintenance station of a third embodiment.

FIG. 17 is a perspective view of the maintenance station 5. Cap holder 7 is attached to guide shaft 8 and provided with cap 6. Motor 38 and cam supporting shaft 15 are connected to attachment plate 40 of the maintenance station 5. Cam 13 provided with gear 12 is pivotally disposed on the cam supporting shaft 15. An end of thrust pin 16 screwed into the cam 13 is inserted in the slot of cam supporting shaft 15 for preventing the cam 13 from moving in the axial direction of the shaft 15. Small gear 11 on the shaft of motor 38 engages with gear 12 incorporated with the cam 13. Rotation of the cam 13 is controlled by rotating reversing or stopping the motor 38. Cam follower 26 on a side of the cap holder 7 extends into the groove in the side of the cam 13. As the cam 13 rotates, the cam follower 26 moves through a minimum radius section 61, a maximum radius section 49, and an intermediate section 48 of the groove cam, and the cap holder 7 reciprocates pivotally or swingingly around guide shaft 8 as a center, and cap 6 moves toward or away from the ink-jet head 1. Nozzle plate 35 with nozzle holes 34 is positioned on the side of the ink-jet head 1 facing the cap.

The cam 13 and a one-way clutch 43 are inserted onto the cam supporting shaft 15 individually in order. The cam 13 is rotatable in opposite directions relative to the cam supporting shaft 15, while the one-way clutch can rotate only counter-clockwise relative thereto. A drive shaft 69 of the piston is fitted on the one-way clutch 43 and fixed thereto. The eccentric shaft 17 is attached to the drive shaft 69 of the piston and is offset by an eccentric distance L from the center of rotation of the drive shaft 69 of the piston. Four catches or cogs 44 are provided on the drive shaft 69 of the piston at intervals of 90°. Each cog 44 is shaped almost as a right triangle. A right angle section or side is engaged by a ratchet, and a non-right angle section or side is not engaged by such ratchet. Therefore, when a cog 44 is pressed at the right angle section thereof by the ratchet, the drive shaft 69 of the piston rotates in the corresponding direction. However, the ratchet runs over the non-right angle section of cog 44, so that the drive shaft 69 of the piston does not rotate in the opposite direction.

A ratchet shaft 47 supports a ratchet 45 on the side of the cam 13, and a torsion spring 46 engages with the ratchet 45 and ratchet shaft 47. The ratchet 45 always receives counterclockwise force (as shown in FIG. 17) relative to the cam 13 by the force of the torsion spring 46, but the rotation of the ratchet 45 is suppressed by the support of the drive shaft 69 of the piston. The ratchet 45 is engaged with a cog 44 only when the cam 13 rotates counterclockwise. Rotation of other cam 13 rotates ratchet 45 that engages with a cog 44 so as to rotate the drive shaft 69 of the piston. When the cam 13 rotates clockwise, the drive haft 69 of the piston does not rotate since engagement between the ratchet 45 and the cogs is canceled by ratchet 45 running over the non-right angle sides of cogs 44. Even if a clockwise rotation force is attempted to be imported to the drive shaft 69 of the piston by external action, the drive shaft 69 of the piston does not rotate clockwise since the one-way clutch 43 does not allow the drive shaft 69 of the piston to rotate clockwise. Therefore, when the cam 13 rotates clockwise, the end of the ratchet 45 simply runs over the next cog 44. When the cam 13 rotates counterclockwise again, the drive shaft 69 of the piston rotates counterclockwise since the ratchet 45 engages with a cog 44. Thus, the drive shaft 69 of the piston can be operated intermittently by control of the cam 13.

Figure 22:
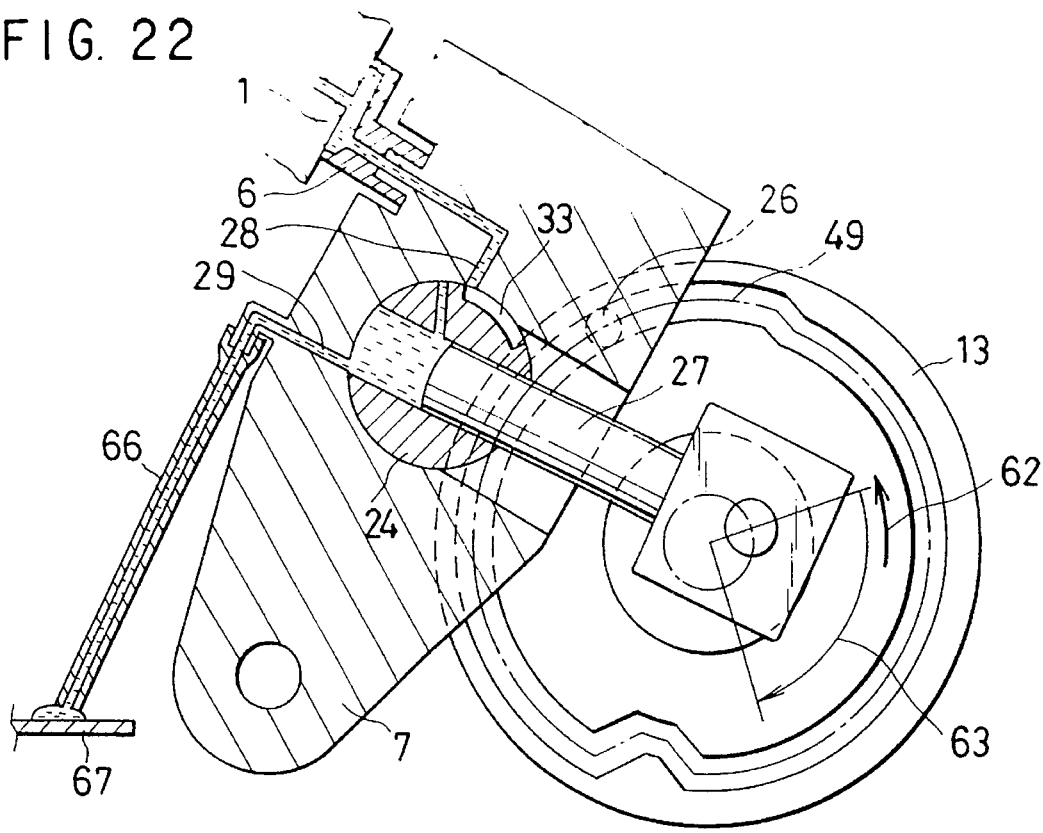
FIG. 22 is a similar sectional view of the cap holder just before a third reverse rotation of the cam.

The cap holder 7 has a cylindrical hollow internal recess section wherein cylinder 24 of almost the same diameter as that of the cylindrical hollow section is rotatably disposed. Lids 25 are provided at both opposite end openings of the hollow section of the cap holder 7, and such lids 25 suppress axial movement of the cylinder 24. One end of piston 27 is engaged with the eccentric shaft 17, and the other end of piston 27 is inserted into a cylindrical hollow opening in cylinder 24 that is disposed perpendicular to the direction of the axis of the cylinder 24. When the eccentric shaft 17 rotates, the piston 27 slides inside the opening of the cylinder 24 and at the same time the cylinder 24 rotates about its axis. The rotation of the cylinder 24 is a reciprocating rotational motion, a center of which occurs when the piston 27 is at an upper dead center point or a lower dead center point. At the cap holder 7 are provided exhaust port 29 which is connected, only during compression, to one end of the hollow opening section of the cylinder 24, and absorption or suction port 28 which is connected, only during absorption or intake, to connection slot 32 of the cylinder 24. The port 28 opens at the hollow section or recess and the external surface of the cap holder 7. The opening of port 28 to the hollow section in cap holder 7 is adapted to be connected to the slots 32 and 33 in cylinder 24 by rotation of the cylinder 24. The external opening of the port 28 external side is connected to the cap 6 for ink absorption. Exhaust port 29 opens to the hollow section and to the external surface section of the cap holder 7. The opening of port 29 to the hollow section in cap holder 7 is adapted to be connected to a pressure chamber by rotation of cylinder 24. The external opening of port 29 is connected to a tube 66 (FIG. 22).

One end of connection hole or slot 32 is connected to the hollow opening in the cylinder 24, and the other end of slot 32 opens on the outer surface of the cylinder so as to be able to be connected with the absorption port 28 by rotation of cylinder 24. When the piston 27 passes through the upper dead center point, the absorption process or intake stroke is started to generate a vacuum in pressure chamber 31 formed by the hollow section of the cap holder 7, the hollow opening of the cylinder 24 and the upper face of the piston 27. When piston 27 reaches the connection hole or slot 32, the inside of cap 6 is evacuated via connection hole 32 and absorption port 28. As the process moves from absorption or intake stroke or process to a compression process or stroke, the connection between the absorption port 28 and the connection hole 32 is cut off, and, alternatively, the connection groove or hole 33 disposed on the exterior of cylinder 24 is connected with the absorption port 28. As one end of connection hole 33 is communicated with a hole 68 in the cap holder 7, the inside of the cap 6 is open to atmospheric pressure via the port 28 and the connection hole 38. Ink drawn out through exhaust port 29 is exhausted to an ink absorber 67 via tube 66.

Figure 18:
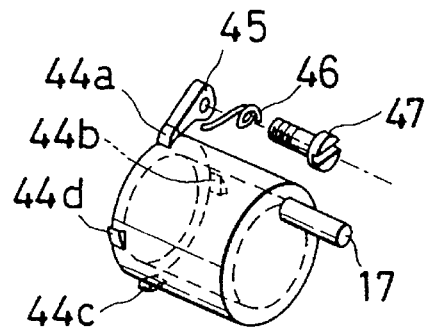
FIG. 18 is an enlarged perspective view of part C of FIG. 17.

FIG. 18 is an enlargement of area C in FIG. 17, showing the configurations of cogs 44, ratchet 45, torsion spring 46 and ratchet shaft 47. Cogs 44 in FIG. 17 correspond to first cog 44a, second cog 44b, third cog 44c and fourth cog 44d in FIG. 18. The first cog 44a and the eccentric shaft 17 are aligned in a plane containing the central axis. The cogs 44a, 44b, 44c and 44d are disposed with 90 degree intervals therebetween. The ratchet 46 is pivotally mounted on the ratchet shaft 47, and threads at a front end of the ratchet shaft 47 are threaded into the side of the cam 13. Opposite ends of the torsion spring 46 are abutted against cam 13 and ratchet 45. The ratchet 45 receives a counterclockwise moment about ratchet shaft 47 as a center by the action of the torsion spring 46.

The operation of the maintenance station 5 constructed as above will be explained below, with reference to FIGS. 1, 17, 18, 19, 20, 21, 22, 23, 24, 25 and 26.

Figure 25:
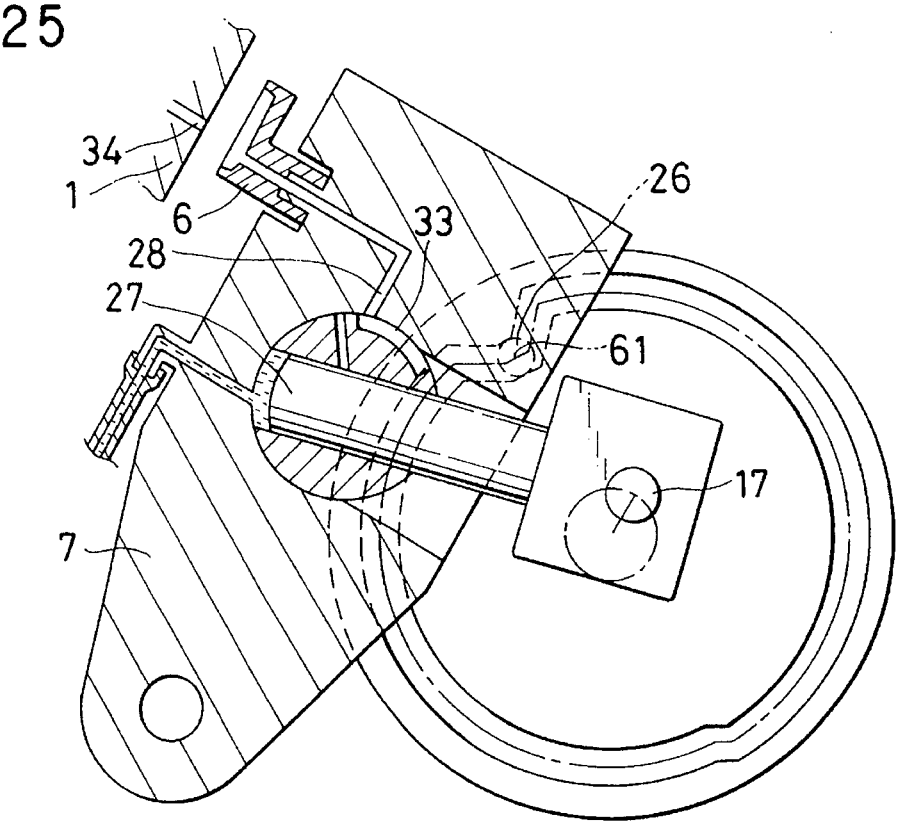
FIG. 25 is a similar sectional view of the cap holder in a stopped state at a starting point of the cam.

The cam follower 26 originally is at minimum radial portion 61 of the cam, and the piston 27 is during the process of a compression stroke as shown in FIG. 25. The carriage 2 moves to the home position 37 and motor 38 is driven. The cam 13 and the eccentric shaft 17 rotates together counterclockwise. When the motor 28 starts, the cam follower 26 moves to the maximum radial portion 49 of the cam and the cap 6 moves against ink-jet head 1. The ratchet 45 is in mesh with the first cog 44a, and the cam 13 drives the eccentric shaft 17, causing the piston 27 to move forward and the cylinder 24 to rotate clock-wise.

Figure 19:
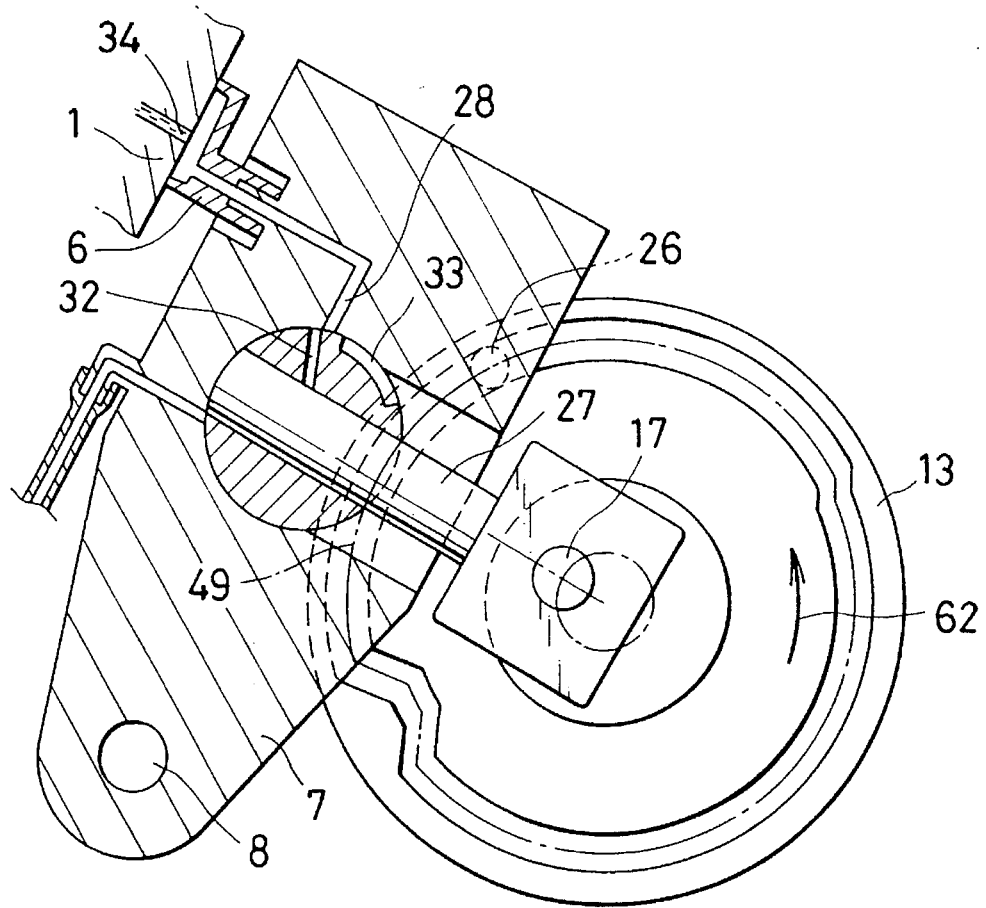
FIG. 19 is a sectional view showing a cap holder of the third embodiment shut off from atmosphere.

FIG. 19 is a cross sectional view showing a section of the cap holder 7 when the cam 13 has swung 90° in the counterclockwise direction from the origin of the cam. The cam follower 26 is at the maximum radial portion 49 of the cam groove, and the cap 6 is against the ink-jet head 1. The piston 27 which has ended the compression process or stroke is at the upper dead center point. Since the linking hole or groove 33 is cut off from the absorbing port 28, the inside of the cap 6 is isolated from the exterior atmosphere. When ending the use of the ink-jet printer, a change in viscosity of the ink component within the ink-jet head resulting from evaporation can be prevented at such condition. In a usual absorbing operation, the cam 13 is further rotated in the counterclockwise direction indicated by arrow 62 showing the rotation of the cam. The ratchet 45 is in mesh with the first click 44a. The eccentric shaft 17 rotates, the piston backs away or retracts, and the cylinder 34 rotates in the clockwise direction.

Figure 20:
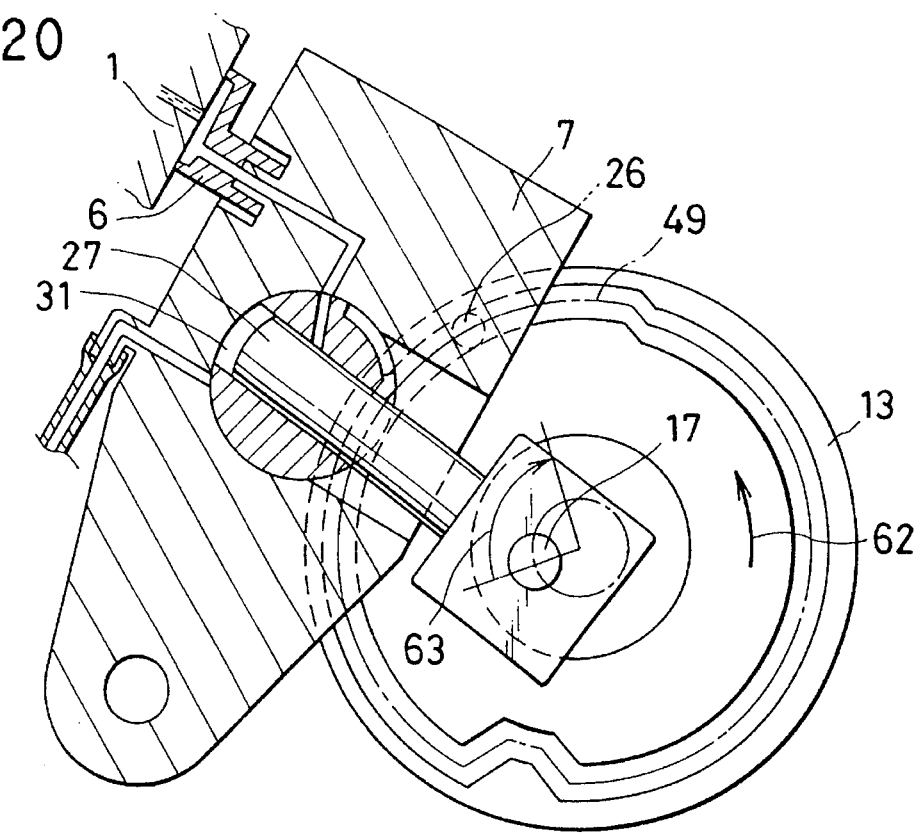
FIG. 20 Is a similar sectional view of the cap holder just before a first reverse rotation of the cam.

FIG. 20 is a cross sectional view showing a section of the cap holder 7 when the cam 13 has rotated 150° in the counterclockwise direction from the origin of the cam. The cam follower 26 is at the maximum radial portion 49 of the cam groove, and the cap 6 is against the ink-jet head. The piston 27 has passed the upper dead point and is in an absorption or intake stroke or process, creating pressure chamber 31. The linking hole 32 and the absorbing port 28 are connected to each other, but connection between the pressure chamber 31 and the linking hole 32 is blocked by the piston 27.

When the motor 38 is reversed by a control device, now shown, the cam 13 rotates in the direction of arrow 63 which shows the return of the cam. Because of clutch 43, the eccentric shaft 17 is not reversely rotated. When the cam 13 reverses by 100°, the ratchet 45 passes over the second cog 44b. Since the cam follower 26 is at the maximum radial portion 49 of the cam groove during this time, the cap 6 is maintained against the ink-jet head. Thereafter, when the motor 38 is rotated normally by the control device, not shown, the cam 13 begins to rotate in the direction of arrow 62. Thus, the ratchet 45 comes into engagement with the second cog 44b. The eccentric shaft 17 rotates, and the piston 27 is retracted further, thus enlarging the pressure chamber 31.

Figure 21:
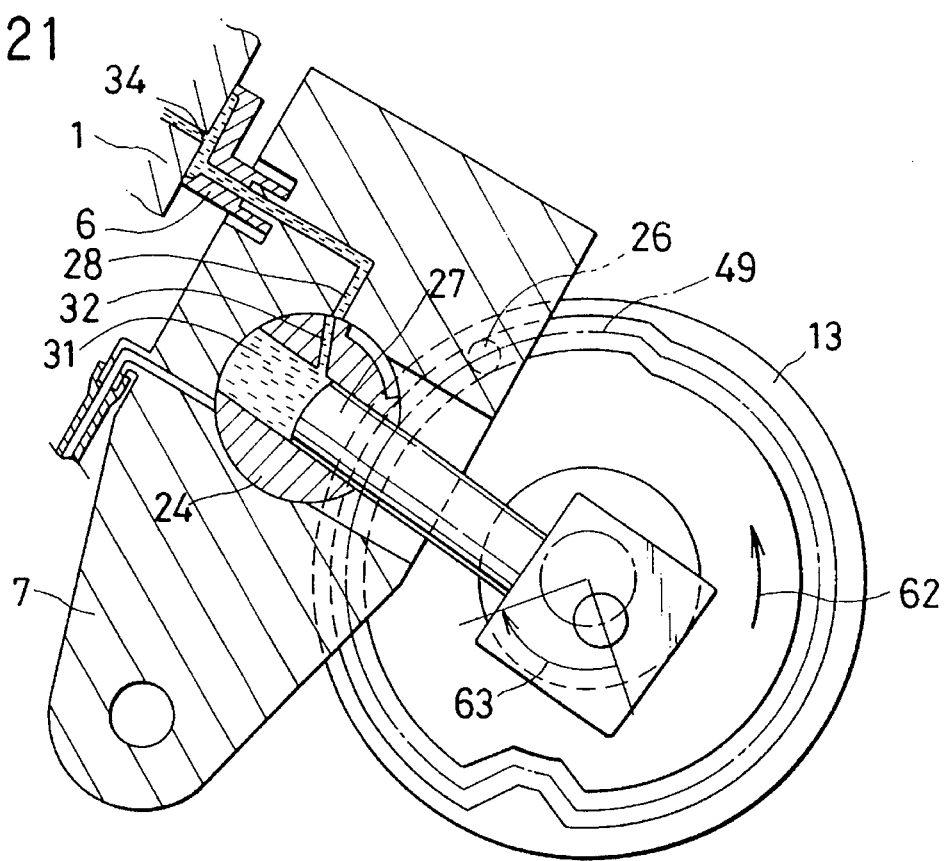
FIG. 21 is a similar sectional view of the cap holder just before a second reverse rotation of the cam.

FIG. 21 is a cross sectional view showing a section of the cap holder 7 when the cam 13 has rotated back by 100° in the counterclockwise direction after rotating 100° from the condition shown in FIG. 20. Since the cam follower 26 is on the maximum radial portion 49, the cap 6 is against the ink-jet head 1. As the top plane of the piston 27 passes the linking hole 32, ink within the ink-jet head 1 is absorbed or drawn into the cylinder 24 via the linking hole 32 and the absorbing port 28. To absorb ink by destroying the meniscus of ink in the nozzle holes 34, the pressure chamber, where vacuum condition has been sufficiently increased, is connected to the cap 6. As shown above, old ink is absorbed from the nozzle holes 34 which will not be used for a long time, and bubbles within the ink-jet head 1 are discharged to recover the flow of ink. Next, the cam 13 is reversed by 100° in the direction of the arrow 63. The ratchet 45 runs over the third cog 44c. The cam 13 rotates in the direction of the arrow 62, and the ratchet 45 comes in mesh with the cog 44c. From this condition, the cam 13 is rotated, and the cylinder 24 is rotated in the counterclockwise direction after backing away and then forwarding the piston by the rotation of the eccentric shaft.

FIG. 22 is a cross sectional view showing a section of the cap holder 7 when the cam 13 has rotated back by 100° in the counterclockwise direction after rotating 100° in from the condition shown in FIG. 21. Since the cam follower is in the maximum radial portion 49 of the cam groove, the cap 6 is against the ink-jet head 1. The piston 27 has passed the lower dead center point, and is in a compression process. The discharge port 29 is connected to chamber 31, and ink is discharged to the absorbing body 67 after passing through tube 66. The absorbing port 28 is connected to the linking hole 33. Next, the cam 13 is reversed by 100° in the direction of the arrow 63. The ratchet 13 rotates in the direction of the arrow 62, and the ratchet 45 comes into mesh with the fourth cog 44d.

Figure 23:
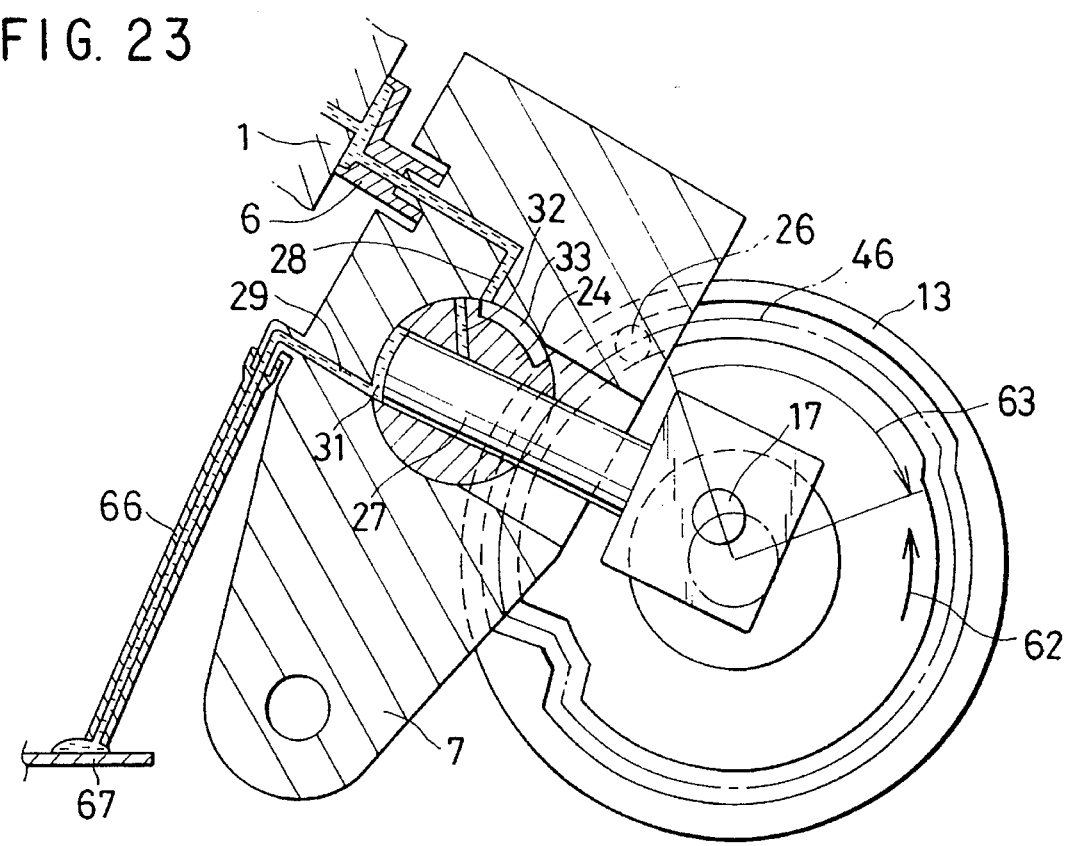
FIG. 23 is a similar sectional view of the cap holder just before a fourth reverse rotation of the cam.

FIG. 23 is a cross sectional view showing a section of the cap holder 7 when the cam 13 has rotated back by 100° in the counterclockwise direction after rotating 100° from the condition shown in FIG. 22. Ink of the cylinder 24 is discharged to the absorbing body 67 after passing the discharge port 29 and the tube 66. Since the cam follower is on the maximum radial portion of the cam groove, the cap 6 is against to the ink-jet head 1. Although the absorbing port 28 is connected to the linking hole 33, ink within the absorbing port 28 will not flow out since the cap 6 and the ink-jet head 1 are in contact with each other. Ink is filled inside the cap 6, the absorbing port 28, and the linking hole 32. Next, the cam 13 is reversed by 100° as indicated by arrow 63. The ratchet 45 passes over the first cog 44a. Then the cam 13 rotates in the direction of the arrow 62, and the ratchet 45 comes into mesh with the first cog 44a. When the eccentric shaft 17 rotates, the cylinder 24 rotates clockwise, and the piston 27 passes the upper dead center point, to be in the absorbing process. The absorbing port 28 and the linking hole 32 are connected to each other.

Figure 24:
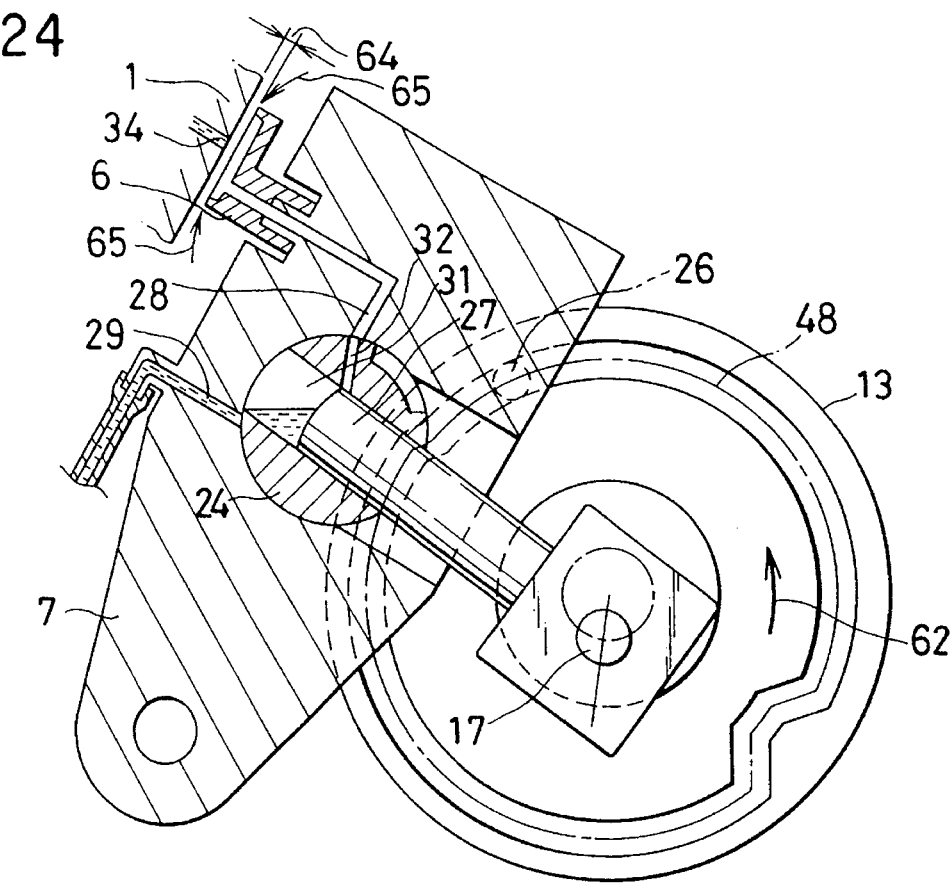
FIG. 24 is a similar sectional view of the cap holder showing suction with the cap partially open.

FIG. 24 is a cross sectional view showing a section of the cap holder 7 when the cam 13 has rotated back by 150° after rotating 100° from the condition shown in FIG. 23 and 200° from the origin of the cam, in the counterclockwise direction. The radius of the cam 13 changes at the position 180° from the origin of the cam, and the cap 6 recedes or withdraws from the ink-jet head by a gap 64. The gap 64 between the ink-jet head and the cap is 0.1 to 0.5 millimeters. The cam follower 26 is at the half-opened or intermediate portion 48 of the cam groove, and there is a gap of, e.g., 0.2 millimeters between the ink-jet head 1 and the cap 6. When the cam 13 is rotated by an extra 50°, the piston 27 passes the linking hole 32, absorbs air from the gap 64 between the ink-jet head and the cap, as shown by arrow 65, and absorbs ink at the surface of the nozzle hole 34 and within the cap 6. Ink within the absorbing port 28 and the linking hole 32 is also absorbed.

The wiping of the nozzle surface is necessary to improve the quality of printing, in removing ink or paper powder stuck to the nozzle plate 35 when trying to spread ink in the correct direction. However, when ink on the nozzle plate 35 is wiped, ink is scraped toward the nozzle hole 34, creating a puddle of ink with bubbles. Since the pressure of ink within the ink-jet head is negative, ink including bubbles is absorbed or drawn inside the ink-jet head 1, and no ink spreads out from the nozzle hole 34. Functions such as moving the wiper 39 are unnecessary because the spreading direction will not be disordered by the ink remaining around the nozzle holes 34, since ink at the surface of the nozzle holes 34 which has absorbed ink from the ink-jet head 1 is removed, and because no bubbles get into the ink-jet head 1 even after wiping. Since ink filled in the cap 6 and the absorbing port 28 is removed, bubbles are pressed into the ink-jet head 1 by the capillary pressure of ink within the cap 6 or the absorbing port 28 during the next capping operation, and ink will be spread for sure. The cam 13 and the eccentric shaft 17 rotate in the direction of the arrow 62. The piston 27 passes the lower dead center point, the discharge port 29 and the cylinder 24 come into contact with each other, the piston 27 goes into the compression process, and ink and air is discharged from the discharge port 29. Finally, the radius of the cam 13 shortens, nearing the origin.

FIG. 25 shows a cross sectional view of the cap holder at the origin of the cam. The cam follower 26 is on the minimum radial portion 61 of the cam groove, and the cap 6 is spaced from the ink-jet head 1. The eccentric shaft 17 is in the middle of the operating direction of the piston 27, and will not interfere with the point of the piston 27 even if the cap holder 7 backs away. The ink-jet head 1 moves to the printing position from the home position 37, and the surface of the nozzle hole 34 is wiped with the wiper 39. The head then again returns to the home position 37, and the above operation of the maintenance station 5 starts again.

Figure 26:
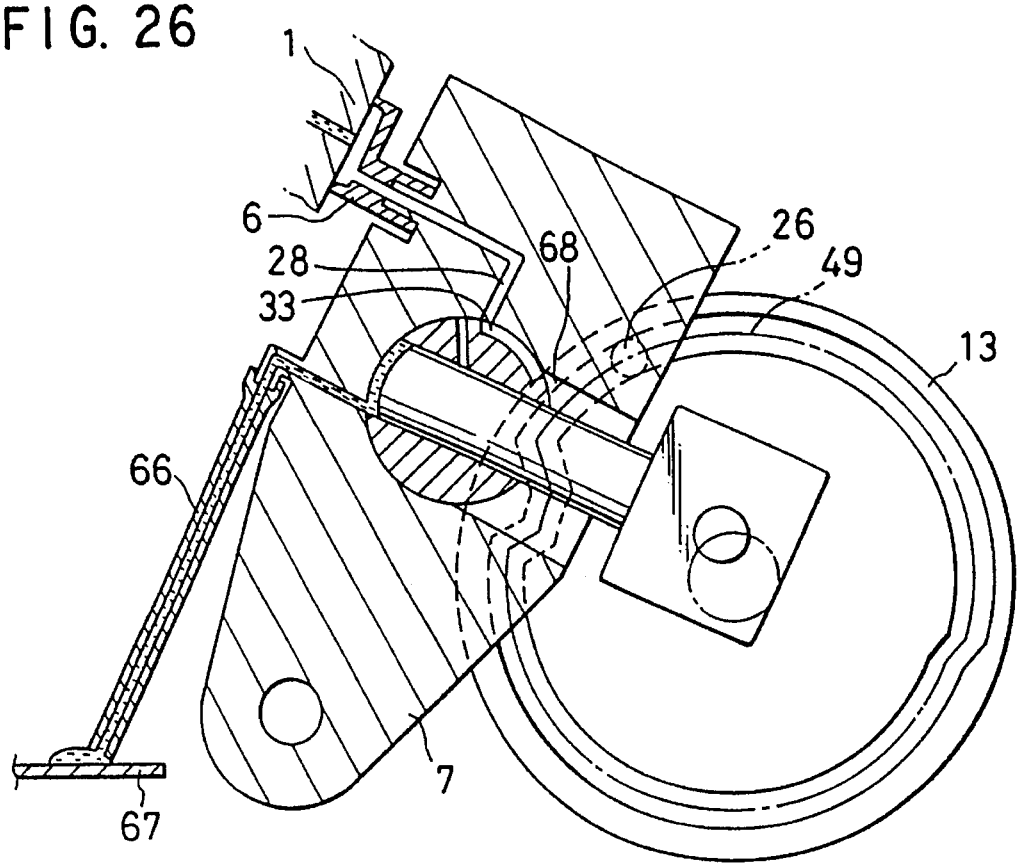
FIG. 26 is a similar sectional view of the cap holder with an inner part of the cap is opened to the atmosphere.

FIG. 26 is a cross sectional view showing a section of the cap holder 7 after the cam 13 has rotated by 45° counterclockwise from the origin of the cam. The cam follower 26 is on the maximum radial portion 49 of the cam groove, and the cap 6 is against the ink-jet head 1. The inside of the cap 6 is opened to atmospheric pressure via the absorbing port 28, the linking hole 33, and releasing hole 68 of the piston. After the cap 6 has come into contact with the ink-jet head 1 in the process of capping, it is further pressed toward the ink-jet head 1 by about 0.5 millimeter. Although the volume within the cap 6 decreases, the pressure will not increase. Thus, no bubbles are pressed into the ink-jet head 1.

According to the maintenance station which operates as stated above, the pump can be operated many times during an opening-and-shutting movement of the cap. Therefore, after a used ink cartridge is replaced by a new one, an appropriate method of drawing ink into the ink-jet head 1 can be provided.

For example, by rotating the cam 13 by 150° from the origin as in the condition shown in FIG. 20, and then reversing it by 100° to place it at a position 50° from the origin, and further rotating to-and-fro between the section of 50° and 150°, the cap 6 intermittently rotates the eccentric shaft 17 a plural number of times. Further, by driving the piston at the condition where the cap 6 is in contact with the ink-jet head 1 to repeat the absorbing/compressing process of the piston 27, air within the ink-jet head 1 is intermittently absorbed and ink can be filed. In this case, the inside of the cap is opened to the atmosphere in the compressing process. In the absorbing process, however, the inside of the cap is shut off from the atmosphere, so that the vacuum condition within the cap can be made higher to absorb air within the ink-jet.

According to the embodiment as stated above, the present ink-jet printer is smaller and its construction is simpler than a conventional ink-jet printer, because a pump is built into the cap holder, using a construction different from that of the past. The construction of a conventional ink-jet printer is complicated since each of a cap of a maintenance station, a cap holder, an atmosphere releasing valve, an absorbing pump, and a cam used for maintaining printing quality is individually provided.

When ending the use of the ink-jet printer, a change in viscosity of the ink component within the ink-jet head resulting from evaporation can be prevented. To improve the flow of ink, ink is drawn from the cap via linking hole 32 and absorbing port 28 by destroying a meniscus at a vacuum higher in pressure than capillary pressure of ink within the nozzle. Old ink is absorbed from the nozzle which has not been used for a long time, and bubbles within the ink-jet head are discharged. Ink within the ink-jet head is drawn to the cylinder in a condition where the cap is in contact with the ink-jet head.

After providing a small gap between the ink-jet head and the cap, air is absorbed from such gap. At the same time, ink at the nozzle surface and within the cap is absorbed, and ink inside the absorbing port and the linking hole is absorbed. By removing ink from the nozzle which has absorbed ink, the direction of spreading will not be directed by the tension of remaining ink near the nozzle. Also, since no bubbles get into the ink-jet head even after wiping, functions such as moving the wiper are not necessary. Further, since ink filled into the cap and the absorbing port is removed, bubbles are pressed into the ink-jet head by the capillary pressure of ink within the cap or the absorbing port during the next capping operation, and ink will be spread for sure. Furthermore, since the pump can be operated many times during one opening-and-shutting movement of the cap, an appropriate absorbing method for filling ink into the ink-jet head 1 is provided when a used ink cartridge is replaced by a new one. In this way, an ink-jet printer provided with a maintenance station which operates accurately is achieved.

Figure 27:
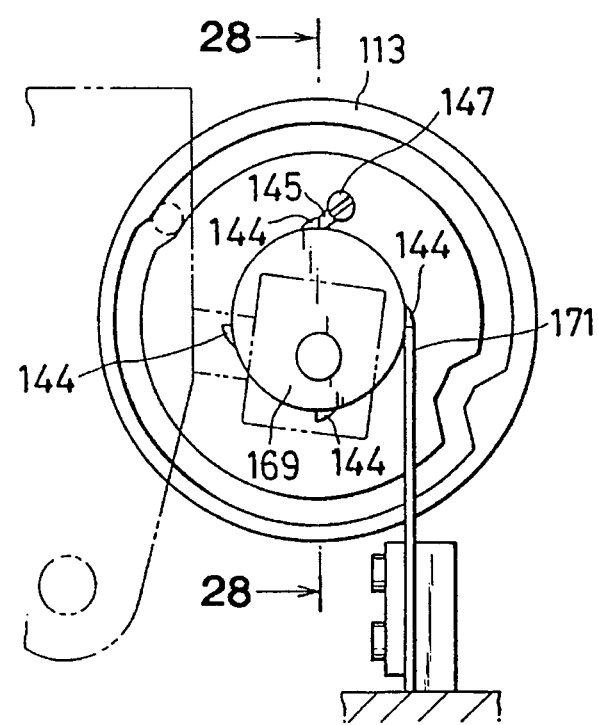
FIG. 27 is a side view of one-way transfer member.

FIG. 27 relates to a one directional transfer sending means constituting a fourth embodiment of the present invention. As in the third embodiment, a cam 13 is mounted on a piston drive shaft 169 having four cogs 144. A ratchet 145 is rotatably provided about a ratchet shaft 147 on a side surface of cam 113 to be engageable with the cogs 144. The ratchet 145 receives moment in counterclockwise direction (as shown) by a torsion spring (not shown). A plate spring 171 is fixed to a fixed portion of the maintenance station, and an end of the plate spring engages with one of the cogs 144.

Figure 28:
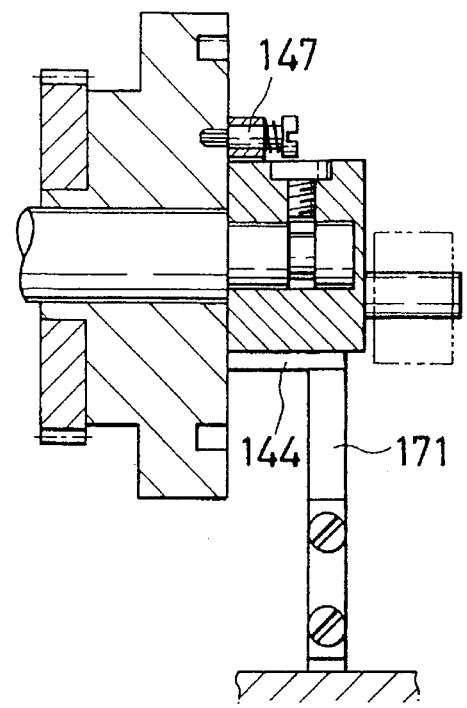
FIG. 28 is a sectional view of the fourth embodiment.

FIG. 28 is a cross-sectional view, taken along a line 28—28 of FIG. 27, showing that the ratchet shaft 147 and the plate spring 171 are axially spaced in the direction of the shaft to avoid interference with each other, and the axial width of the cog 144 is long enough to engage both with the ratchet and the plate spring.

Figure 29:
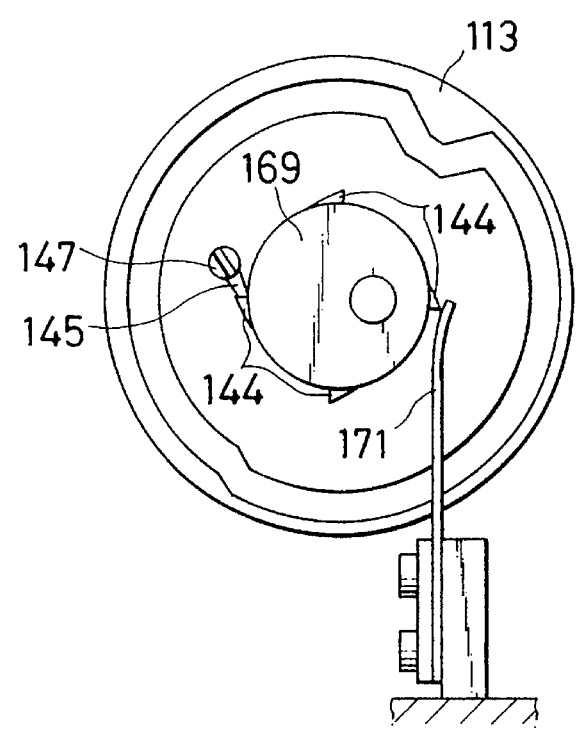
FIG. 29 is a side view showing operation of the fourth embodiment.

FIG. 29 is a view similar to FIG. 27 for explaining the operation of the one directional transfer means thus constructed. When cam 113 rotates counterclockwise, the rotating force is transmitted to piston drive shaft 169 through the ratchet shaft 147, the ratchet 145, and a cog 144. According to the rotation of the cam 113, the cogs 144 deflect the plate spring 171. When the cam rotates by 150°, an end portion of a cog passes the plate spring 171, and the plate spring snaps back toward a rear surface of such cog. Then cam 113 moves counterclockwise. As the cog 144 is contacting the plate spring 171, the piston drive shaft 169 is not rotatable. As the cam 13 rotates clockwise, the ratchet 145 rides over the next cog as the torsion spring bends, and ratchet 145 rotating with the ratchet shaft as its center. When the cam 113 rotates up to 100 degrees clockwise, it stops. When the cam 113 moves further counterclockwise, the ratchet 145 and a cog 144 will engage with each other, and the piston drive shaft 169 rotates with the cam 113, the plate spring 171 passes over the next click 144 and stops after the rotation of 100 degrees. In this manner, the same function as the maintenance station disclosed above may be realized. This embodiment provides that plate spring 171 is used instead of a one directional clutch which is very expensive.

Figure 30:
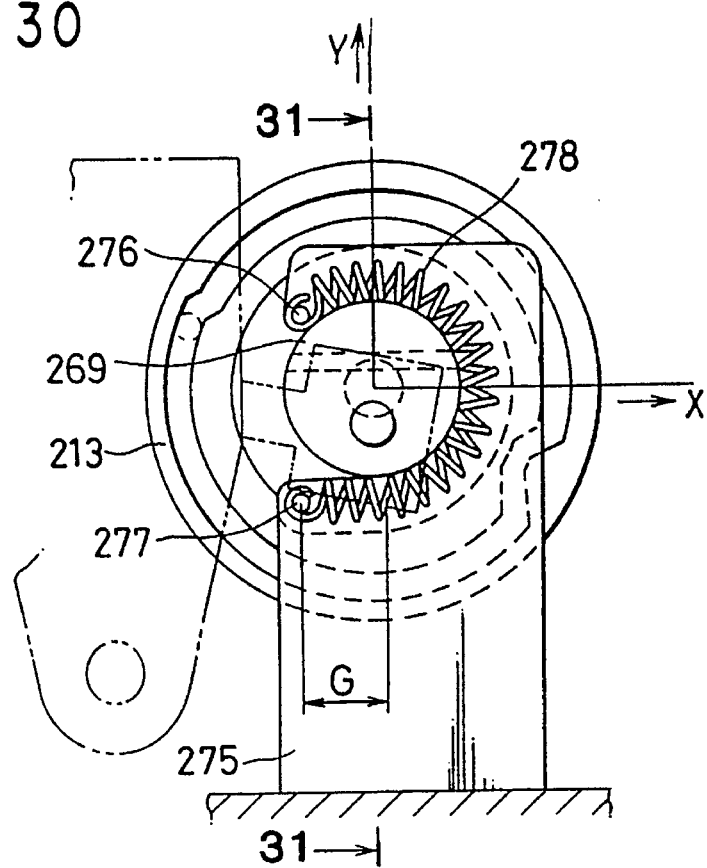
FIG. 30 is a side view of a one-way transfer member of a fifth embodiment.

FIG. 30 is an assembled view showing a fifth embodiment with respect to the one directional transfer means. A fixing or support plate 275 is provided adjacent a cam 213. Spring hooking or support pins 276 and 277 is provided on the fixing plate 275. The position of the spring hooking pins 276 and 277 on the fixing plate 275 will be explained. As shown in FIG. 30, the right and left direction is determined as an X coordinate axis, and the upper and lower direction is determined as a Y coordinate axis, with the center of piston drive shaft 269 as an origin. The right portion of the X coordinate axis is determined as the plus direction, and the upper portion is determined as the plus direction of the Y coordinate axis. When the outer diameter of a spring is Db and the outer diameter of the piston drive shaft is Dp, the fixing point of the spring hoking pin 276 would be, $X=-G$, $Y=((Db+Dp)^2/4-G^2)^{1/2}$, and the fixing position of the spring hooking pin 277 would be $X=-G$, $Y=-(Db+Dp)/2$. Here, G takes a plus value and the scope will be Db $<G<Dp/2$. The piston drive shaft 269 is provided on the same shaft as the cam 213 and extends through a hole in the fixing plate 275. One end of a control spring 278 is hooked on the spring hooking pin 276, and the spring is wrapped around the piston drive shaft 269 except for the length of G at the other end portion (an end portion of the control spring with length of G from the spring hooking pin 277). The other end of the control spring is hooked on the spring hooking pin 277.

Figure 31:
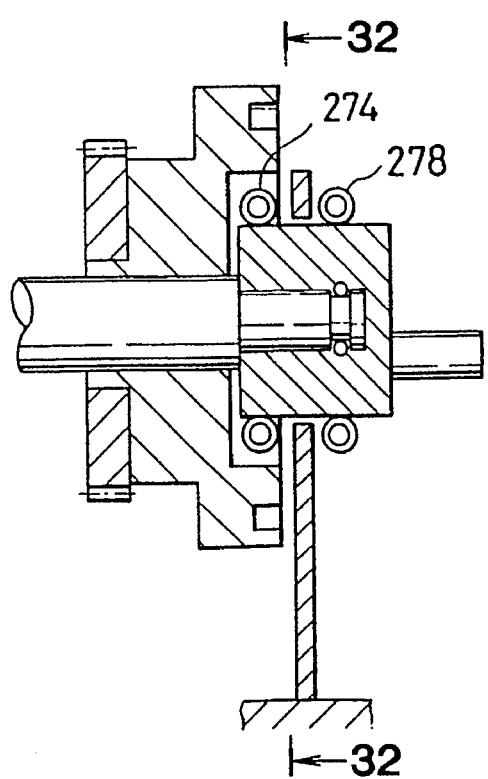
FIG. 31 is a sectional view of the fifth embodiment.

FIG. 31 shows a cross-sectional view taken along line 31—31 of FIG. 30. This is provided a concave recess in the side surface of cam 113. A drive spring 274 is provided in such recess so that it will not interfere with cap holder 7. The control spring 278 is provided axially adjacent to the drive spring 274.

Figure 32:
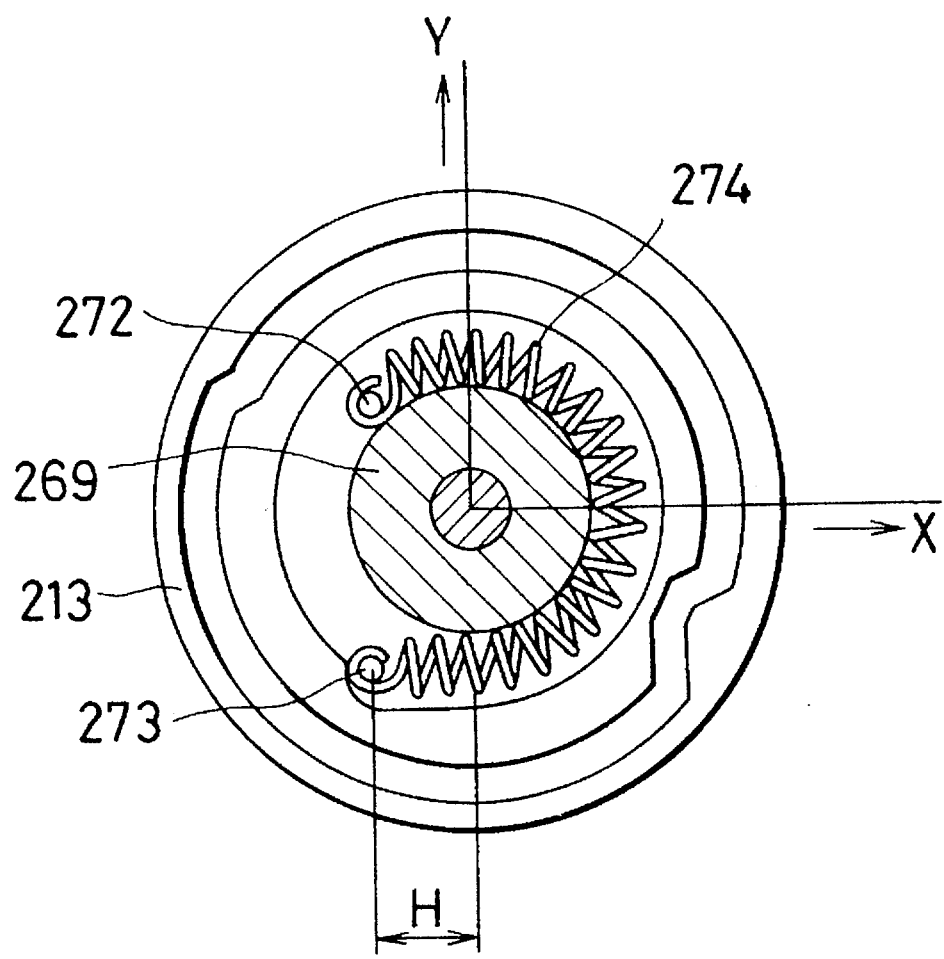
FIG. 32 is a sectional view of the fifth embodiment.

FIG. 32 is a cross-sectional view taken along a line 32—32 of FIG. 31. Spring hooking pin 272 and spring hooking pin 273 are fixed to the cam 213. The position of the spring hooking pin 272 and the spring hooking pin 273 on the cam 213 will be explained. As shown in FIG. 32, the right and left directions are determined as an X coordinate axis, and the upper and lower directions are determined as a Y coordinate axis, with the rotation center of the cam 213 as the origin. The right portion of the X coordinate axis is determined as a plus direction, and the upper portion is determined as a plus direction of the Y coordinate axis. When the outer diameter of the spring is Db and the outer diameter of the piston drive shaft is Dp, the fixing position of the spring hooking pin 272 would be X=–H, Y=((Db+Dp)²/4=H2)½, and the fixing position of the spring hooking pin 273 would be X=–H, Y=–(Db+Dp)/2. Here, H takes a plus value and the scope will be Db<H<Dp/2. The piston drive shaft 269 is provided on the said shaft as the cam 213. One end of drive spring 274 is hooked on the spring hooking pin 272, and spring 274 is wrapped around the piston drive shaft 269 except for the length of H at the other end portion (an end portion of the drive spring 274 with length of H from the spring hooking pin 273). The other end of the drive spring is hooked on the spring hooking pin 273.

Next, the operation of the one directional transfer means thus constructed according to this embodiment will be explained. When the cam 213 rotates counterclockwise, a frictional force is generated between the drive spring 274 and the piston drive shaft 269 due to the tension of the drive spring 274. The rotation force of the cam 213 then is transmitted to the piston drive shaft 269, and the piston drive shaft starts rotating counterclockwise. The length G of the control spring 278 then stretches in part. The frictional force caused by the tension of the control spring 278 is lost. The piston drive shaft 269 and the control spring 278 are without relative friction. When cam 213 and piston drive shaft 269 rotate up to a position of 150 degrees counterclockwise, the direction of rotation of the cam 213 is reversed, and cam 213 begins to rotate clockwise. By the frictional force due to the tension of the control spring 278, the piston drive shaft 269 receives a braking force. As a result, the H part of the drive spring 274 will be stretched in part. The frictional force caused by the tension of the control spring 278 will be lost. Accordingly, the cam 213 rotates clockwise while the piston drive shaft 269 remains stopped. The mechanism of this embodiment is very reasonable because it is constructed of two tension coil springs, and no mechanical parts, such as cogs, torsion springs, or ratchet shafts, and spring plates are used.

A sixth embodiment according to the present invention now will be explained referring to the drawings. FIG. 1 perspectively shows the appearance of the ink jet printer having a maintenance station that can constitute this embodiment. On a surface of ink jet head 1 opposing piece of paper 4 is fixed a nozzle plate having a plurality of nozzle holes. The ink jet head is mounted on carriage 2 which is movable in right and left directions on a guide rod 3. The position of the ink jet head is precisely determined by a motor. The position of the paper 4 is also determined precisely in upper and lower directions. Characters and figures are printed by jetting ink from the nozzle holes while controlling the relative positions of the paper 4 and ink jet head 1 with respect to each other. Maintenance station 5 is provided outside the printing area and includes a cap. The position of carriage 2 when the nozzle holes of the ink jet head 1 are located in front of cap 6 is home position 37. At the right side of the home position 37 is a wiper 39 for wiping the nozzle plate each time the ink jet head 1 moves from the home position 37 to the printing position, and from the printing position to the home position 37.

Figure 33:
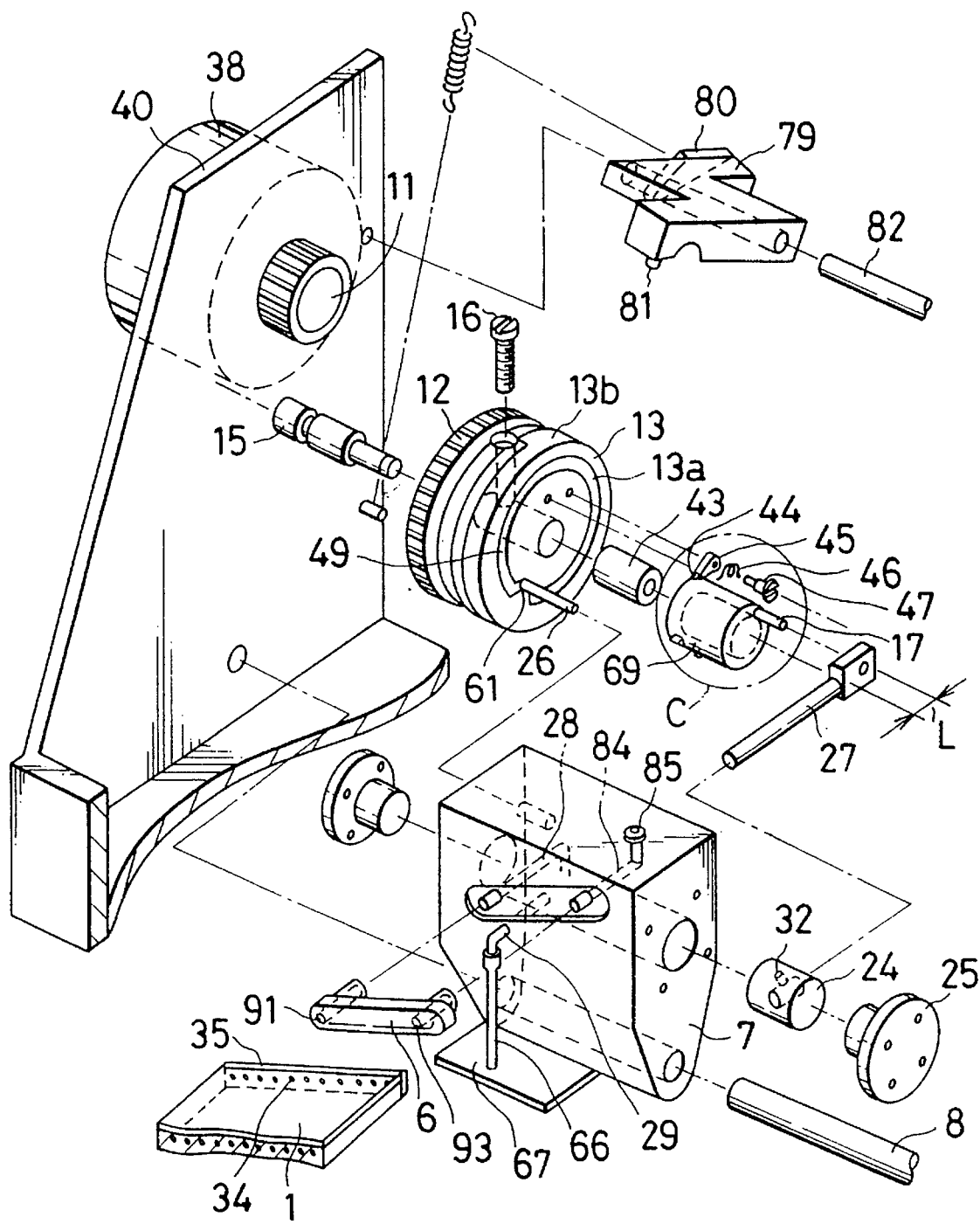
FIG. 33 is a perspective view of a maintenance station of a sixth embodiment.

FIG. 33 is a perspective view showing the maintenance station 5 according to this embodiment of the present invention. Cap holder 7 is fixed to guide shaft 8 and has cap 6. Motor 38 and cam support shaft 15 are fixed to a fixing or support board 40 of the maintenance station 5. Cam 3 having gear wheel 12 is rotatably mounted to cam support shaft 15. An end portion of thrust pin 16 screwed to cam 13 is set into a groove of cam support shaft 15 to prevent cam 13 from moving axially of the cam support shaft 15. Small gear wheel 11 is engaged with gear wheel 12 which is combined with cam 13. Rotation of the cam 13 is controlled by rotating, or reversing, or stopping motor 38. Cam follower 26 is fixed to the side surface of cap holder 7 and has an end extending into a groove in the side surface of the cam. As the cam follower passes through minimum radial portion 61 of the first cam surface or member 13a and maximum radial portion 49 thereof, with rotation of the cam 13, the cap holder 7 rotates about the guide shaft 8 as a center, and cap 6 moves forward and backward with respect to the ink jet head 1.

There is further provided a lever 79 which operates through a cam follower 80, which is in contact with a second cam surface or member 13b which is a cam plate formed on an outer surface of the cam 13. At the end of lever 79 is provided a rubber washer 81. According to rotation of the lever 79 about a lever shaft 82 as a center, the rubber washer 81 opens or closes an air inlet 85. Similarly to the first cam 13a, the second cam 13b includes two radial portions, namely a minimum radial portion and a maximum radial portion.

Nozzle plate 35 having nozzle holes 34 is fixed to a surface of the ink jet head 1 opposing cap 6. The cam 13 and one directional clutch 43 are independently inserted on cam support shaft 15, in such order. The cam 13 is rotatable in opposite directions, however one directional clutch 43 only rotates counterclockwise. The one directional clutch 43 engages the piston drive shaft 69 on which is fixed eccentric shaft 17, offset by an amount L with respect to the rotational center of the piston drive shaft 69. On the piston drive shaft 69 are provided four cogs 44 spaced at intervals of 90° from one another. Each cog is nearly a shape of a right-angled triangle. A right angle surface engages with ratchet 45 that rides over a non-right angle surface. Therefore, if a cog 44 is pushed from the right angle surface thereof by the ratchet, the piston drive shaft rotates. However, when the ratchet is moved from the non-right angle surface side, the ratchet passes over the cog 44, and therefore the piston drive shaft does not rotate.

Ratchet 45 and torsion spring 46 are mounted on ratchet shaft 47 fixed to a side surface of cam 13. The ratchet 45 always receives a force in the counterclockwise direction, relative to cam 13, from torsion spring 46. However, support of the piston drive shaft 69 prevents rotation of the ratchet. The ratchet 45 engages with cogs 44 only when the cam 13 rotates counterclockwise. In such a case, the rotation of the cam 13 is transmitted to the piston drive shaft 69 through the ratchet 45 and a cog 44. When the cam 13 rotates clockwise, engagement between the ratchet 45 and the cog 44 is released, and therefore the piston drive shaft 69 does not rotate. Further, even if an external force is applied to the piston drive shaft 69 in an attempt to rotate it clockwise, the one directional clutch 43 does not allow clockwise rotation of the piston drive shaft 69. Thus, the piston drive shaft 69 does not rotate clockwise. Because of this, if the cam 13 is rotated clockwise, the end of the ratchet 45 passes over the next cog 44 and the ratchet moves to the rear side of such cog. When the cam 13 rotates counter-clockwise again, the ratchet 45 engages such cog 44 and rotates the piston drive shaft 69 counterclockwise. Accordingly, by control of the cam 13 the piston drive shaft 69 can be rotated intermittently.

Figure 43:
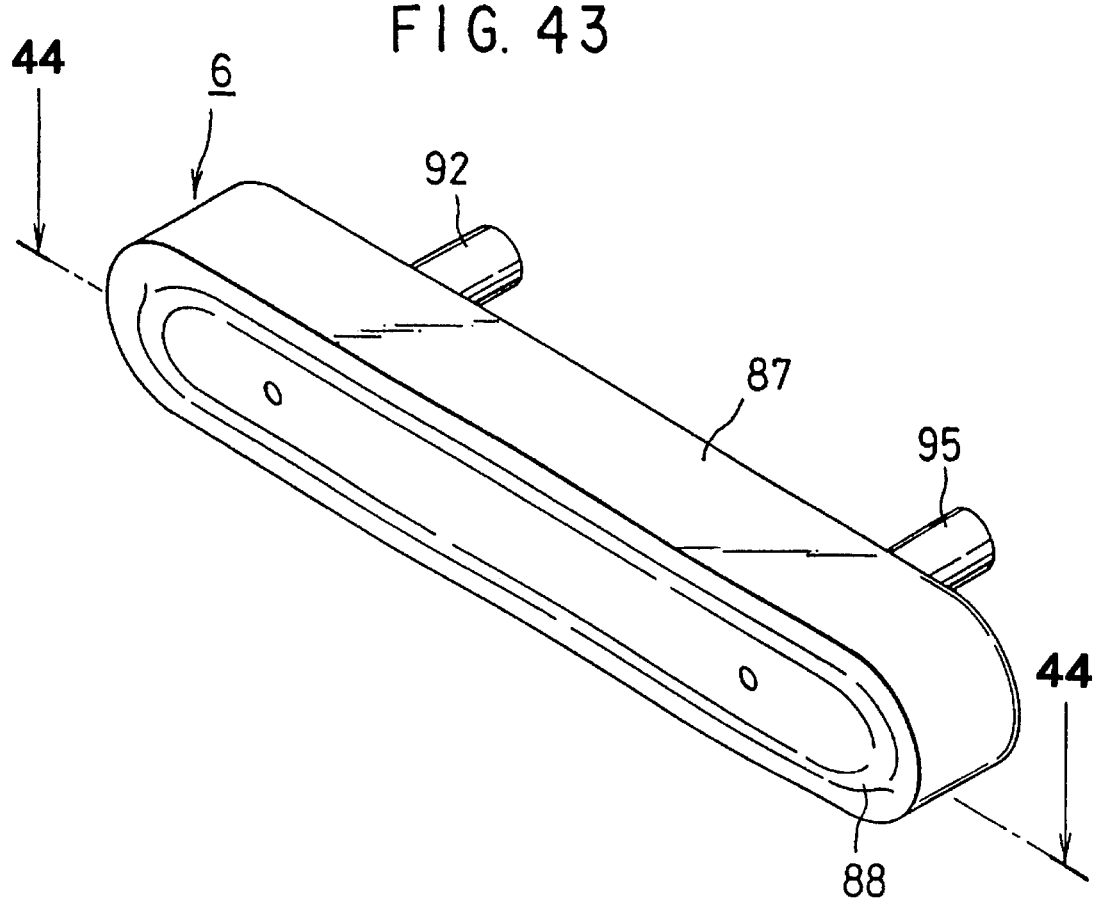
FIG. 43 is a perspective view of the cap of the present invention.

FIG. 43 is a perspective view showing the appearance of the cap 6 used at the maintenance station according to the present invention. A body 87 is large enough to deform when it is pushed toward the ink jet head. A sealing member or portion 88 is provided in the body 87 so that it surrounds the nozzle holes 34 when the cap 6 comes into close contact with the ink jet head. The sealing portion is tapered so that when an end portion thereof comes into contact with the ink jet head 1, it may easily deform so that the cap 6 may closely contact the ink jet head 1. Inside of the sealing portion is formed in a manner such that the length, width, and depth are of minimum values in order that the cap 6 will not contact the nozzle holes 34 when the sealing portion 88 contacts the ink jet head 1. At a rear surface of body 87 are provided pillars 92 and 95.

Figure 44:
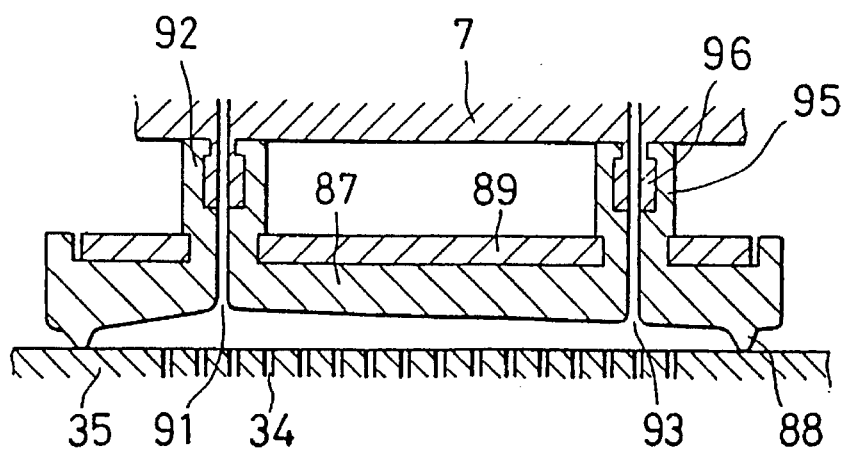
FIG. 44 is a sectional view of the cap.

FIG. 44 is a cross-sectional view taken along a line 44—44 of FIG. 43. The sealing portion 88 is provided at a forward side of body 87. The pillar 92 is of convex shape and is provided at a side opposite the surface opposed to the nozzle plate 35. A suction hole 91 extends through the pillar 92 and is connected to the suction port 28. Pillar 95 also is of convex shape. An air hole 93 extends through the pillar 95 and is connected to air inlet 85 by air through hole or passage 84 as shown in FIG. 33. The cap 6 is fixed to the cap holder 7 by protrusions 96 of holder 7 fitting into pillars 92 and 95. The pressure with which the cap 6 contacts the ink jet head 1, is transmitted from the cap holder 7 through pillars 92, and 95 and to the body 87. The body then pushes the sealing portion 88 toward the ink jet head 1. In order to prevent deformation of the body 87 due to the counter force from the sealing portion 88, a rigid body 89 is provided at a rear surface of the body 87, rigid body 89 being set in the pillars 92 and 95.

The suction strength of the pump now will be described. Supposing the suction capacity of one cycle of a piston to be K. and the inner capacity of the cap 6 and the dead space capacity of the suction hole 91, the suction port 28 or the like to be M, vacuum pressure N toward the ink jet head 1 is N=M/(K+M), if it is supposed that the ink does not overflow from the ink jet head 1 onto the cap 6 during activation of the piston. In order to obtain the maximum vacuum pressure in a fixed suction capacity, it is necessary to make M to be a minimum. According to the structure of the ink jet head 1, the sealing portion 88 has an extremely long and thin front shape. The sealing portion 88 needs to be soft so as to touch the ink jet head 1 closely. The vacuum pressure toward the sealing portion 88 is carried to the main body 87 so as to deform the main body 87. However, the hard body 89 provided on the back of the main body 87 prevents the main body 87 from being deformed. Accordingly, the cap is deformed when pressed against the ink jet head 1 and under vacuum pressure at suction, which enables positive close contact with the ink jet head 1 and obtaining the maximum vacuum pressure by making the inner capacity of the cap being a minimum.

The cap holder 7 has therein a cylindrical hollow opening or recess into which is rotatably mounted cylinder 24. Lids 25 suppress axial movement of the cylinder 24. One end of piston 27 is engaged to the eccentric shaft 17, and the other end is engaged into the cylindrical hollow opening extending through cylinder 24 transversely of the axis thereof. When the eccentric shaft 17 rotates, the cylinder 24 rotates simultaneously with the piston 27 which moves in and out within the opening of the cylinder 24. The rotation of the cylinder 24 is a reciprocating-rotating motion having a center position at the top dead center point or the bottom dead center point of the piston 27. Discharge port 29 connects with the opening of the cylinder 24 only during the compression stroke, and suction port 28 connects with hole 32 of cylinder 24 only during the suction stroke. The suction port 28 opens into the opening in holder 7 and the outer surface of the cap holder 7. Port 28 is connected with the connecting hole 32 by rotation of the cylinder 24. The opening of port 28 outside the cap holder 7 enables suction of ink by the cap 6. The discharge port 29 also has openings in the hollow opening of holder 7 and the outer surface thereof. Port 29 is connected with pressure chamber 31 by rotation of cylinder 24 to tube 66.

One end of the connecting hole 32 communicates with the opening in the cylinder 24 and the other end opens on the cylindrical outer surface of the cylinder 24 and is connectable with the suction port 28 by rotation of cylinder 24. When the piston 27 passes the top dead center so as to begin into suction stroke and increase the vacuum level in the pressure chamber 31, which is defined by the hollow opening in the cap holder 7, the hollow opening in the cylinder 24 and the piston 27, and when the top of the piston 27 reaches the connecting hole 32, the piston 27 creates a suction acting inside the cap 6 through the connecting hole 32 and the suction port 28. As the suction stroke is completed and the compression stroke begins, the connection between the suction port 28 and the connecting hole 32 is interrupted. Ink passes from the discharge port 29 onto the ink absorbing element 67 through the tube 66.

Figure 34:
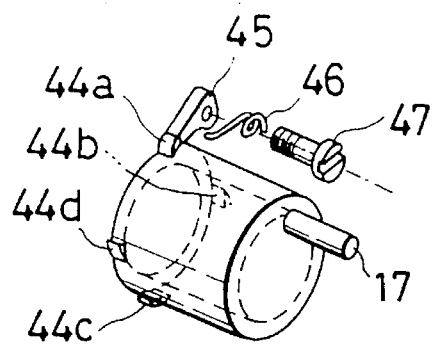
FIG. 34 is an enlarged perspective view of part C of FIG. 33.

FIG. 34 is an enlarged view of portion C shown in FIG. 33, showing the shapes of the cogs 44, ratchet 45, torsion spring 46 and ratchet shaft 47. The cogs 44 shown in FIG. 33 include first cog 44a, second cog 44b, third cog 44c and fourth cog 44d. The first cog 44a and the eccentric shaft 17 are located in the same cross section including a center shaft or axis. Cogs 44a, 44b, 44c and 44d are arranged to have intervals of 90° therebetween. The ratchet 45 is rotatably mounted on ratchet shaft 27 on the side of the cam. One end of torsion spring 46 is fixed to the cam 13 and the other end is fixed to ratchet 45. Torsion spring 46, imparts to ratchet 45 a counter-clockwise moment about the ratchet shaft as a center.

Operation of the maintenance station 5 of this embodiment will be described with reference to FIGS. 1 and 33–42. In FIG. 41, cam follower 26 is at minimum radial portion 61 of the first can 13a. Carriage 2 moves to the home position 37 and motor 38 is driven to rotate cam 13 and the eccentric shaft 17. As soon as the motor 28 starts, the cam follower 26 moves to the maximum radial portion 49 of the first cam 13a so that the cap 6 closely contacts the ink jet head 1. Next, the cam follower 80 is operated following the second cam 13b, the lever 79 is pivoted, and the rubber washer 81 closes the air intake 85. The ratchet 45 engages with the first cog 44a, and the cam 13 drives the eccentric shaft 17.

Figure 35:
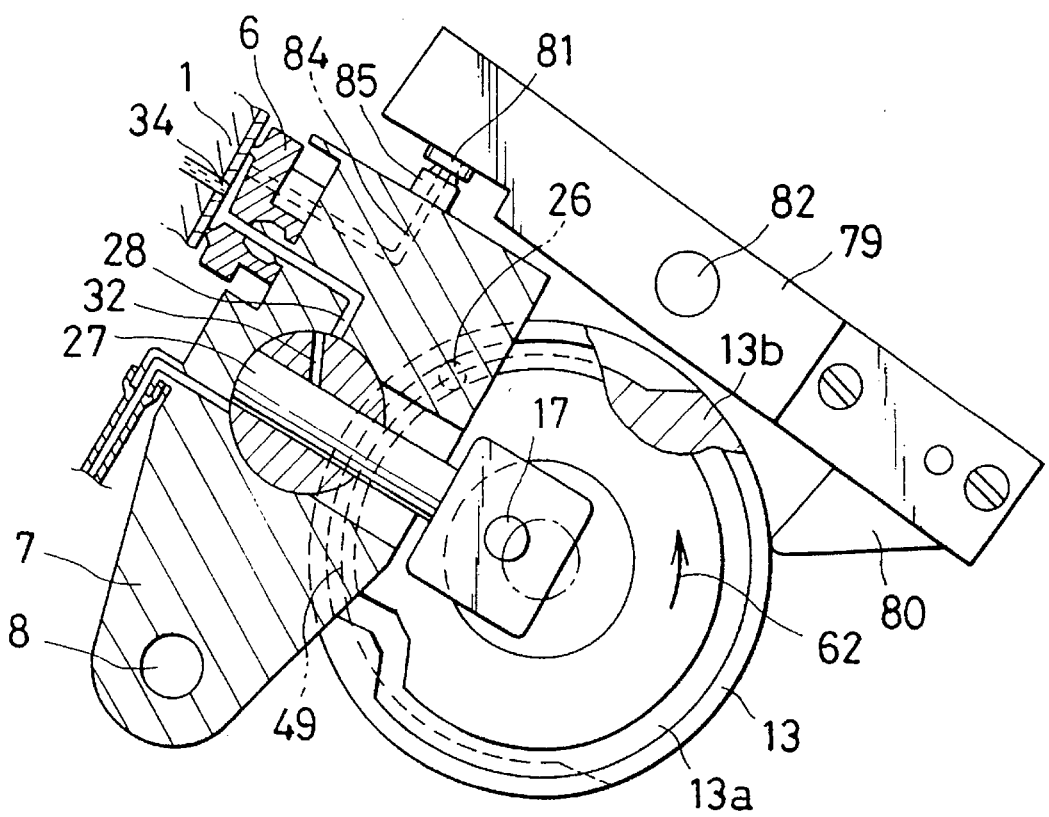
FIG. 35 is a sectional view showing movement of the sixth embodiment.

FIG. 35 is a sectional view of the cap holder 7 with the cam 13 rotated in counterclockwise direction 90° from the original position. The cam follower 26 is in maximum radial portion 49 of the first cam 13a. The cap 6 closely contacts the ink jet head 1. The lever 79 is at the maximum radial portion of the second cam 13b and rubber washer 81 closes the air intake 85. The inside of the cap 6 is in an air shut-off condition. When the ink jet printer is stopped in this condition, a change of viscosity of ink inside the ink jet head 1 due to evaporation can be prevented. In a usual suction operation, the cam 13 further rotates in the direction of arrow 62. The ratchet 45 engages with the first cog 44a.

Figure 36:
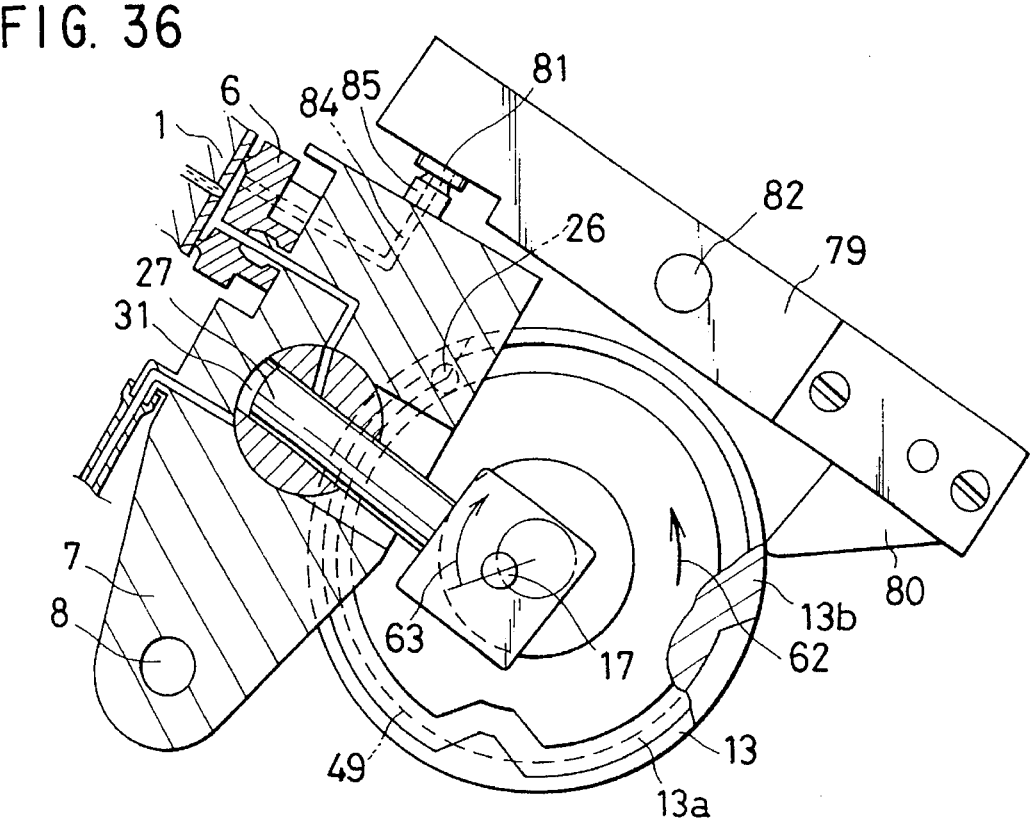
FIG. 36 is a similar sectional view showing further movement of the sixth embodiment.

FIG. 36 is a sectional view showing the cap holder 7 when the cam rotates 150° from the original position in counterclockwise direction. The cam follower 26 is in the maximum radial portion 49 of the fist cam 13a, and the cap 6 closely contacts the ink jet head 1. The lever 79 is positioned at the maximum radial portion of the second cam 3b, and rubber washer 81 closes the air intake 85. The piston 27 passes the top dead center point and begins the suction stroke, and the pressure chamber 31 is created. When the motor 38 is driven reversely by a control apparatus which is not shown, the cam moves reversely in the direction of arrow 63. The eccentric shaft 17 does not so move due to operation of the one-way clutch 43. When the cam 13 rotates 100°, the ratchet 45 moves over the second cog 44b. At such time, since the cam follower 26 is at the maximum radial portion 49 of the first cam 13a, the cap 6 stays close to the ink jet head 1. Then, when the motor 38 again is rotated forwardly by the control apparatus which is not shown, the cam 13 starts rotating in the direction of the arrow 62 and the ratchet 45 engages with the second cog 44b so that the eccentric shaft 17 rotates.

Figure 37:
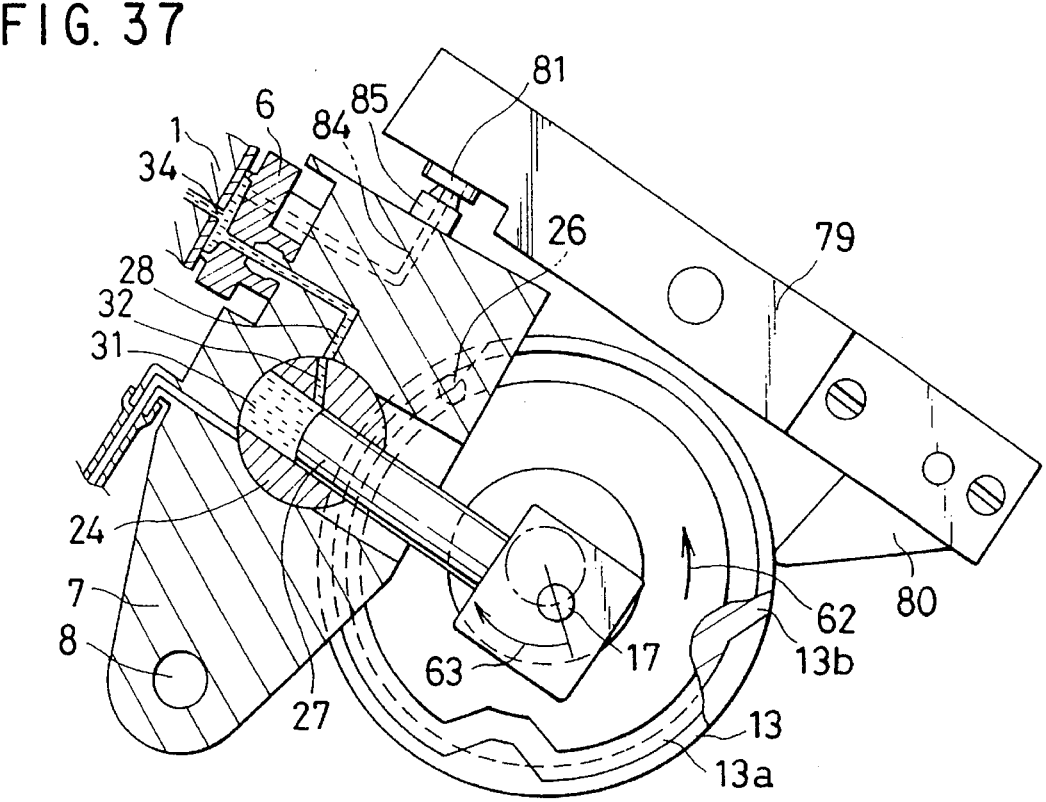
FIG. 37 is a similar sectional view showing further movement of the sixth embodiment.

FIG. 37 is a sectional view showing the cap holder 7 when the can 13 rotates 100° reversely in the clockwise direction from the state shown in FIG. 36, and then further rotates forward 100° in the counterclockwise direction. Since the cam follower 26 is at the maximum radial portion 49 of the first cam 13a, the cap 6 closely contacts the ink jet head 1. The lever 79 is positioned at the maximum radial portion of the second cam 13b, and the rubber washer 81 closes the air intake 85. Since passage from the nozzle holes 34 to the pressure chamber 31 is established via the suction port 28 and the connecting hole 32 with the tip (upper face) of the piston 27 passes the connecting hole 32, the piston withdraws ink in the ink jet head 1 into chamber 31 through the connecting hole 32 and the suction port 28. In order to break the meniscus of ink in the nozzle holes 34 during such suction, the pressure chamber 31 is connected with the cap 6 after the pressure in the chamber is increased sufficiently. In this way, discharge of the ink drops is recovered by discharging air bubbles in the ink jet head 1 simultaneously with withdrawing of old ink from nozzle holes 34 which have not been used for a long time. Next, the cam 13 rotates reversely 100° in direction 63. The ratchet 45 passes over the third cog 44c. The cam 13 rotates in the direction of arrow 62 and the ratchet 45 engages with the third cog 44c.

Figure 38:
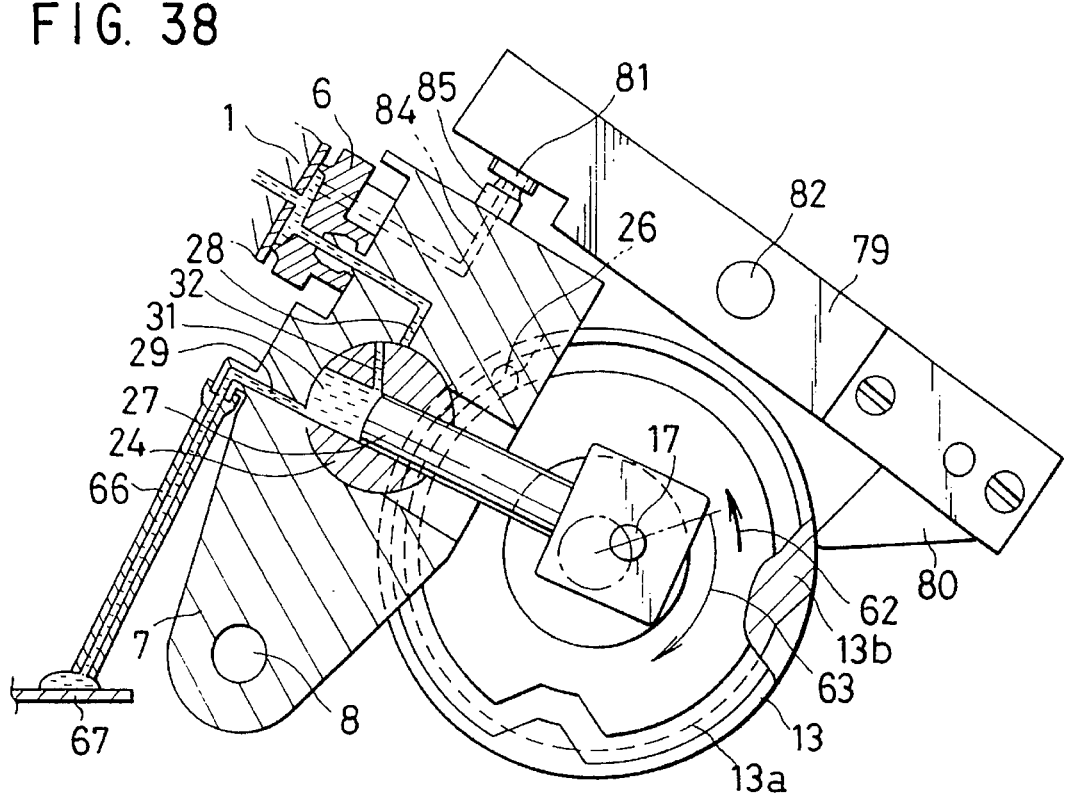
FIG. 38 is a similar sectional view showing further movement of the sixth embodiment.

FIG. 38 is a sectional view showing the cap holder 7 when the cam 13 rotates 100° reversely in the clockwise direction from the state shown in FIG. 37, and then further rotates forward 100° in the counterclockwise direction. Since the cam follower 26 is at the maximum radial portion 49 of the first cam 13a, the cap 6 closely contacts the ink jet head 1. The lever 79 is positioned at the maximum radial portion of the second cam 13b, and the rubber washer closes the air intake 85. The piston 27 passes the bottom dead center point and starts the compression stroke. Discharge port 29 is connected to pressure chamber 31 and ink is discharged onto the ink absorbing element 67 through the tube 66. Next, the cam 13 rotates reversely 100° in the direction of arrow 63. The ratchet 45 moves over the fourth cog 44d. The cam 13 rotates in the direction of the arrow 62 and the ratchet 45 engages with the fourth cog 44d.

Figure 39:
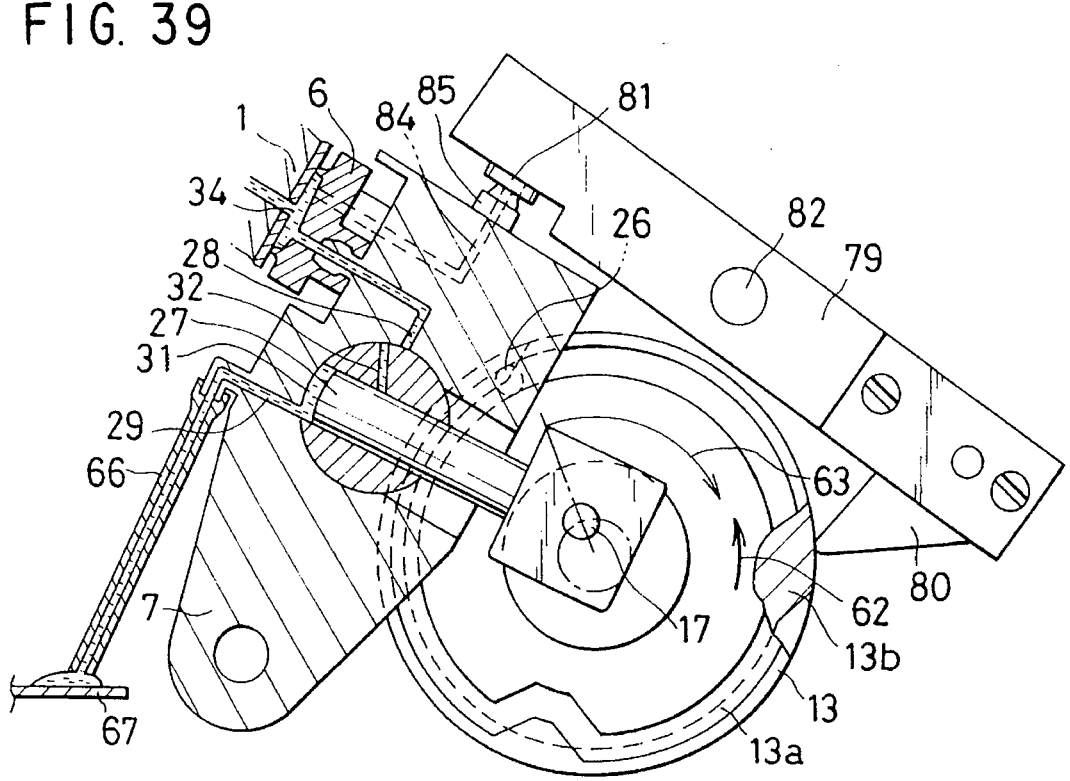
FIG. 39 is a similar sectional view showing further movement of the sixth embodiment.

FIG. 39 is a sectional view showing the cap holder 7 when the cam 13 rotates 100° reversely in the clockwise direction from the state shown in FIG. 38 and then further rotates forward 100°0 in the counterclockwise direction. The ink in the cylinder 24 is discharged to the ink absorbing element 57 through the discharge port 29 and the tube 66. Since the cam follower 26 is at the maximum radial portion 49 of the first cam 13a, the cap closely contacts the ink jet head 1. The inside of the cap 6, the suction port 28 and the connecting hole 32 are filled with ink. Next, the cam 13 rotates reversely 100° in the direction of arrow 63. The ratchet 45 passes over the first cog 44a. The cam 13 rotates in the direction of the arrow 62 and the ratchet 45 engages with the first cog 44a. When the eccentric shaft 17 rotates and the piston 27 passes the top dead center point, the connection between the discharge port 29 and the pressure chamber 31 is interrupted, and the piston 27 again generates the pressure chamber 31. The suction port 28 is connected with the connecting hole 32.

Figure 40:
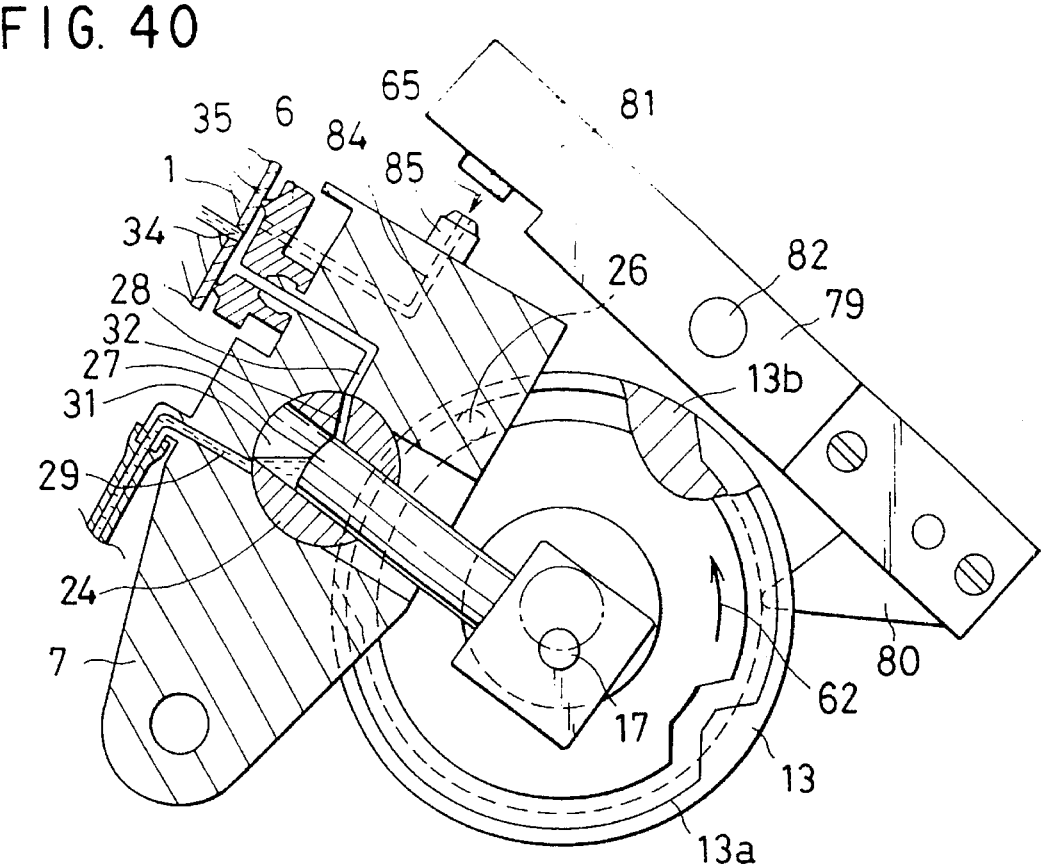
FIG. 40 is a similar sectional view showing further movement of the sixth embodiment.
Figure 41:
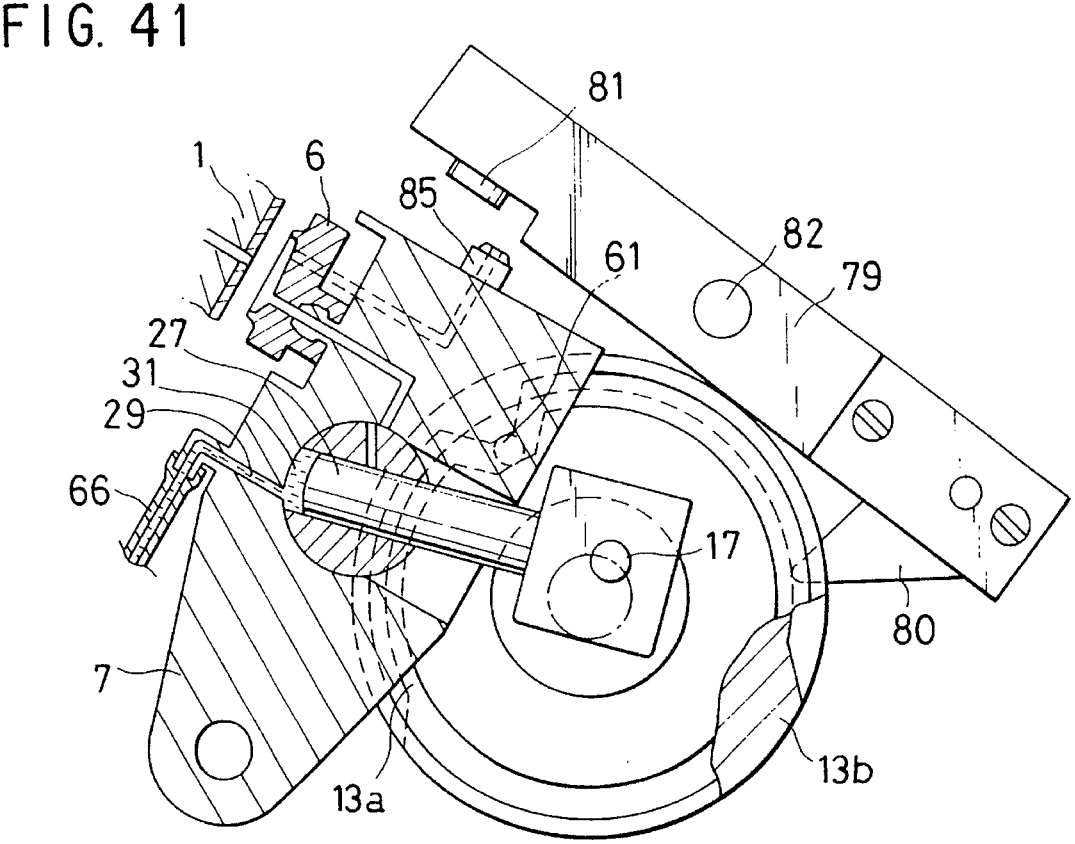
FIG. 41 is a similar sectional view showing further movement of the sixth embodiment.

FIG. 40 is a sectional view showing the cap holder 7 when the cam 13 rotates 100° reversely in the clockwise direction from the state shown in FIG. 39, and then further rotates forward 150° in the counterclockwise direction and 200° from the original position. At a position 180° from the original position of the cam, the radius of the second cam 13b changes and the lever 79 is positioned at the minimum radial portion of the second cam 13b. Thus, the rubber washer 81 moves away from the air intake 85. When the cam rotates further 50° and the piston 27 passes the connecting hole 32, a passage from the air connecting hole 84 to the pressure chamber 31 is established via the suction port 28 and the connecting hole 32. The air is drawn in through air intake 85 as shown by arrow 65. Ink on the surface of the nozzle hole 34 and in the cap 6 is also withdrawn. Simultaneously, ink in the suction port 28 and connecting hole 32 is also suctioned. It is necessary to wipe the surface of the nozzle in order to remove ink or paper powder adhered to the nozzle plate 35 and improve the printing quality by jetting discharged ink drops in a correct direction. However, when wiping the nozzle plate 35 to which ink is adhered, the ink is accumulated toward the nozzle hole 34, which causes ink stagnation containing air bubbles. The ink in the ink jet head 1 has a lower pressure, the ink containing air bubbles is drawn into the ink jet head 1. In this way, ink drops are not discharged from the nozzle hole 34 which suctioned ink containing air bubbles. A mechanism for moving the wiper 39 is not necessary. After taking in air in the direction of arrow 65, and suctioning ink from the ink jet head 1, the discharge direction is not disturbed due to remaining ink around the nozzle 34 by removing ink on the surface. Air bubbles do not move into the ink jet head 1 even after wiping. Furthermore, since ink which fills the cap 6 and the suction port 28 is removed, pushing of air bubbles into the ink jet head 1 due to capillary pressure of the ink in the cap 6 or the suction port 28, which causes problems in discharging ink drops, can be prevented. As the cam and eccentric shaft 17 further rotate, the piston 27 passes the bottom dead center point, and the discharge port 29 is connected with the pressure chamber 31. The piston 27 moves into the compression stroke, and ink and air are discharged from the discharge port 29.

FIG. 41 is a sectional view of the cap holder at the original position of the cam. The cam follower 26 is at the minimum radial portion 61 of the first cam 13a, and the cap 6 is spaced from the ink jet head 1. The lever 79 is positioned at the minimum radial portion of the second cam 13b, and the rubber washer 81 is spaced from the air intake 85. The eccentric shaft 17 is in the middle of the operation distance of the piston 27. Accordingly, even if the cap holder 7 moves backward, it does not interfere with the tip of the piston 27. The ink jet head 1 moves between the home position 37 and the printing position, and the wiper 39 wipes the surface of the nozzle holes 34. The ink jet head 1 returns to its home position 37 so that operation of the maintenance station starts anew.

Figure 42:
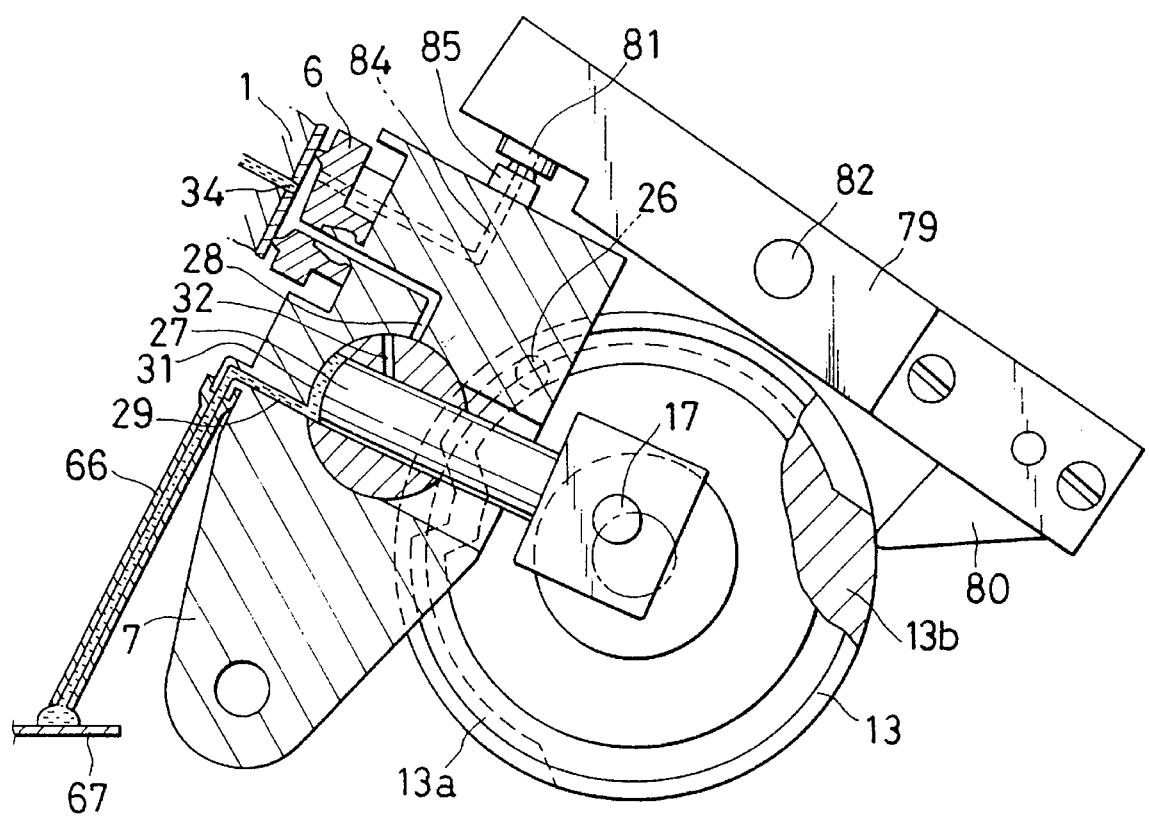
FIG. 42 is a similar sectional view showing further movement of the sixth embodiment.

FIG. 42 is a sectional view of the cap holder 7 when the cam 13 rotates 45° from the original position of the cam in the counterclockwise direction. The cam follower 26 is at the maximum radial portion 49 of the first cam 13a, and the cap 6 closely contacts the ink jet head 1. During capping, after the cap 6 touches the ink jet head 1, the cap is further pressed by 0.3 millimeter toward the head so that the inner capacity of the cap 6 decreases. However, since the lever 79 is positioned at the minimum radial portion of the second cam and the rubber washer is spaced from the air intake 85, the pressure in the cap 6 does not increase and air bubbles are not pushed into the ink jet head 1. After capping, the lever 79 moves to the maximum radial portion of the second cam 13b, and the rubber washer closes the air intake 85. According to the maintenance station which operates in this way, since the pump can be operated a number of times during one open/close operation of the cap, it is possible to realize a suction method suitable for filling the ink jet head 1 with ink after exchanging a used ink cartridge with a new ink cartridge.

In addition, according to the maintenance station of the present embodiment, since it is possible to operate the pump a number of times during one open/close operation of the cap, suction suitable for filling the ink jet head with ink is possible. For example, after the cam rotates forward 150° in the counterclockwise direction from the original position and rotates reversely 100° so as to be at 50° from the original position, by rotating between the positions of 50° and 150° so as to rotate the eccentric shaft forwardly a plurality of times, the cap 6 is connected with the ink jet head 1 and the air intake is closed by the rubber washer 81 of the lever 79. Under conditions that air is shut out from the inside of the cap, the position is driven to repeat the suction/compression operations so as to suction air in the ink jet head efficiently. Accordingly, it is possible to fill the ink jet head 1 with ink. In this way, it is possible to obtain an ink jet printer having a maintenance station which positively activates the head.

As described above, according to the present embodiment, besides the effect which was described in the third embodiment, by providing the suction port and the opening on the cap side of the air connecting hole at positions spaced from each other and opening the opening on the cap side of the air connecting hole when nozzle suctioning of the ink jet head, the air is drawn into the space formed between the nozzle hole of the ink jet head and the cap which caps the nozzle. Furthermore, ink on the surface of the nozzle and in the cap is suctioned, and ink in the suction port and the connecting hole also is suctioned up at the same time. Since, by removing ink on the surface of the nozzle after suctioning the discharging direction is not disturbed due to tension of ink remaining around the nozzle and air bubbles do not come into the ink jet head even after wiping, a mechanism for moving the wiper is not necessary. Since, under the condition that air is shut out from the inside of the cap, the piston is driven to repeat the suction/compression operations so as to suction air in the ink jet head efficiently, it is possible to realize a suction method suitable for filling the ink jet head with ink after exchanging a used ink cartridge with a new ink cartridge. In this way, it is possible to obtain an ink jet printer having a maintenance station which positively activates the head.

Figure 45:
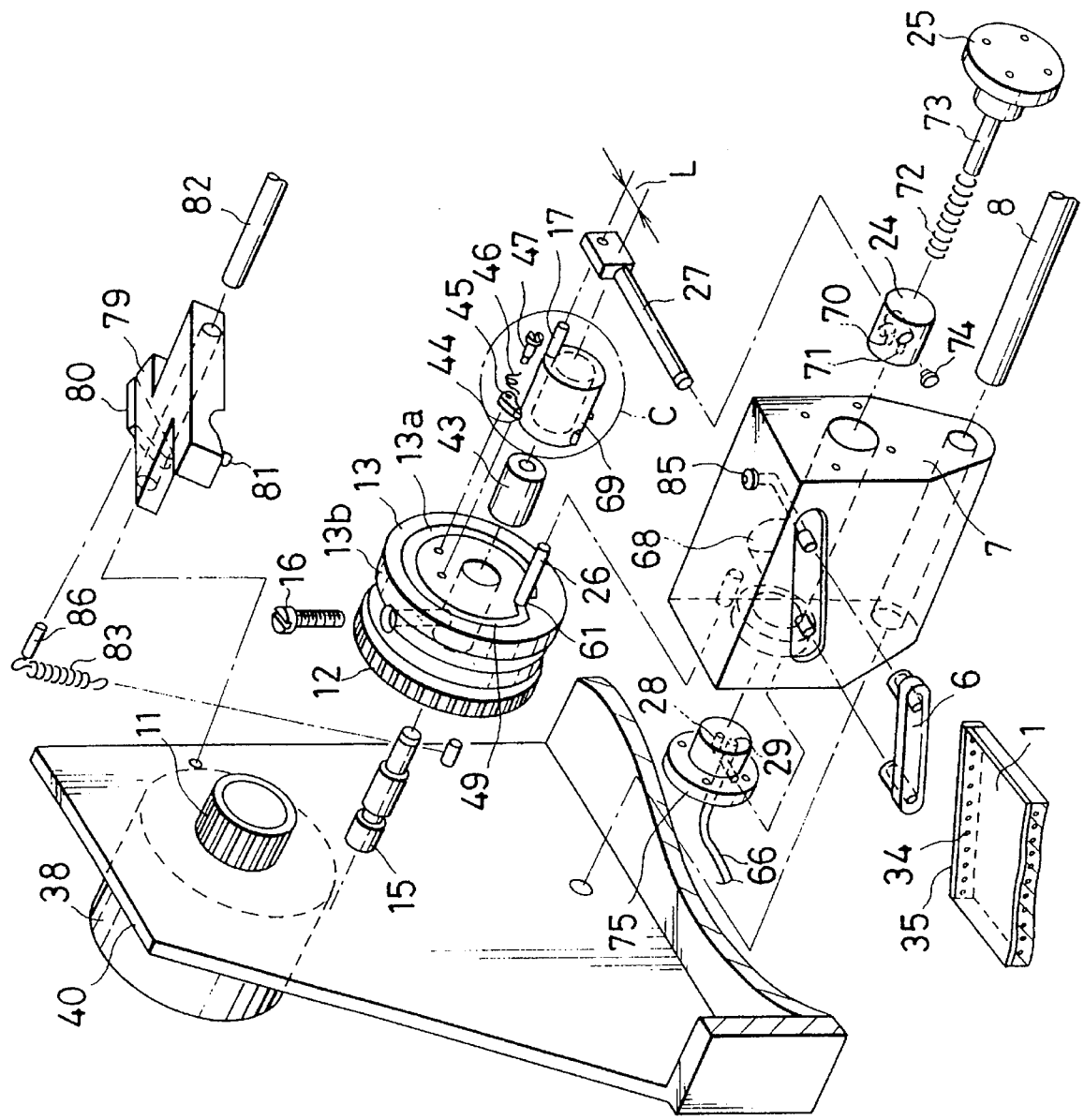
FIG. 45 is a perspective view of the maintenance station of a seventh embodiment of the present invention.

A seventh embodiment of the present invention will be described hereinbelow. FIG. 45 is a perspective view illustrating maintenance station 5 according to this embodiment. Cap holder 7 is mounted on guide shaft 8 and has a cap 6. Fixed on mounting plate 40 of maintenance station 5 are motor 38 and cam support shaft 15. Cam 13 with gear 12 attached thereto is secured on the cam support shaft 15 for pivotal movement, and a tip end of thrust pin 16 which is threaded on cam 13 extends into a groove in the cam support shaft 15 so as to prevent the cam 13 from moving in the axial direction relative thereto. Small gear 11 is fixed in position on the motor shaft and meshes with the gear 12 which is integrally formed with the cam 13. Rotation of cam 13 is controlled by operating motor 38 to turn, reverse or to stop. Cam follower 26 is fixed in position on a lateral surface of the cap holder 7, and the cap holder 7 is caused to pivot around the guide shaft 8. Cap 6 advances and retracts toward and away from the ink jet head 1 when the tip end of follower 26 enters a groove defined in the end surface of the cam 13 and when cam 13 rotates to allow the cam follower to pass through a minimum radius portion 61 of first cam 13a and a maximum radius portion 49 thereof. Lever 79 has cam follower 80 which comes into contact with second cam 13b defined in the lateral surface of the cam 13 as a plate cam. Lever 79 is provided at its tip end with rubber seat 81. Tension coil spring 83 has one end cradled on a spring hook 86 defined in the lever 79. The opposite end of the tension coil spring 83 is cradled on the mounting plate 40. Thus, a clockwise moment is imposed upon the lever 79. As the lever 79 pivots about lever shaft 82, rubber seat 81 may open or close the atmospheric air suction port 85. Second cam 13b is formed in two diameters, i.e. a minimum radius portion and a maximum radius portion.

Nozzle plate 35 having nozzle holes 34 therein is fixed in position on a surface of the ink jet head 1 opposing cap 6. Cam 13 and one-way clutch 43 are inserted on cam support shaft 15 in such described order. Although cam 13 may rotate in opposite directions relative to the cam support shaft 15, the one-way clutch 43 will not rotate other than in the counterclockwise direction relative to the cam support shaft 15. The one-way clutch 43 further comprises piston driving shaft 69 which is secured in position. Eccentric shaft 17 is attached on the piston drive shaft 69 and is offset by an eccentricity L relative to the rotational center of piston drive shaft 69. Four cogs or pawls 44 are arranged on the piston drive shaft 69 at angular spacings of 90°. Each cog or pawl 44 is formed substantially in a right triangle shape which may mesh at its right angle side with ratchet 45 but cannot mesh at its non-right angled portion with the ratchet. Thus, piston drive shaft 69 may be rotated by the right-angled side of cog 44 by ratchet 45, but piston drive shaft 69 will not be rotated, even when the ratchet is depressed, from the non-right angled portion since the ratchet overrides the cog 44. Ratchet shaft 47 is mounted on the lateral surface of the cam 13, with ratchet 45 and torsion spring 46 mounted on ratchet shaft 47. A counterclockwise moment is constantly imposed on the ratchet 45 relative to the cam 13 by torsion spring 46. The ratchet 45 meshes with a pawl 44 only when the cam 13 is caused to rotate in the counterclockwise direction, and the rotary movement of the cam 13 is transmitted to the piston drive shaft 69 via the ratchet 45 and the pawl 44. When the cam 13 rotates in the clockwise direction, the piston drive shaft 69 cannot rotate because the ratchet 45 is released from engagement with the pawl 44. Even when an external rotary force is imposed on the piston drive shaft 69 to attempt clockwise rotation, the piston drive shaft 69 will not rotate in the clockwise direction due to one-way clutch 43. Thus, when the cam 13 is caused to turn in the clockwise direction, the tip end of the ratchet 45 will override the subsequent pawl 44. Such tip end of the ratchet 45 moves to a rear surface of the pawl 44 of the cam 13 under the effect of the torsion spring 46. When the cam 13 is caused to rotate again in the counterclockwise direction, the ratchet 45 meshes with the pawl 44 resulting in rotation of the piston drive shaft 69 in the counterclockwise direction. Consequently, it is possible for an operator to feed the piston drive shaft 69 intermittently under controlled operation through cam 13.

Figure 46:
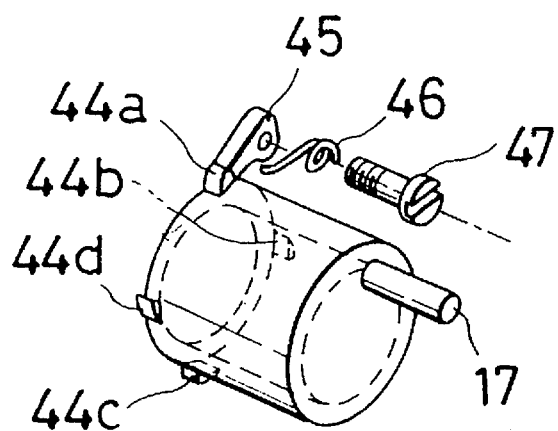
FIG. 46 is an enlarged perspective view of part C of FIG. 45.

FIG. 46 is an enlarged view of portion C shown in FIG. 45 and corresponds to FIGS. 18 and 34.

The cap holder 7 has therein a hollow cylindrical opening or chamber into which fits cylinder 24 of substantially the same diameter as such hollow chamber, for pivotal or rotational movement relative to holder 7. Switch plate 75 is capped over one of two opposite end openings of such chamber, i.e. at the side of the cam. An enclosure 25 is capped over the opposite opening. The enclosure 25 includes a spring guide 73 at a side inserted into the opening and serves to press cylinder 24 against the switch plate 75 via a compression spring 72. One end of piston 27 is freely slidably inserted in the through-hole in the cylinder 24 passing through piston bore 68 of the cap holder 7. Eccentric shaft 17 provided on piston drive shaft 69 is inserted into the opposite end of piston 27. When the piston drive shaft 69 is rotated, the eccentric shaft 17 imparts to the piston a movement whereby into and from the cylinder 24, while the rotary position of the cylinder 24 varies with the advance of the rotary angle of the eccentric shaft 17.

Movement of piston 27 from the top dead center point to the bottom dead center point is a suction stroke during which piston 27 is withdrawn from cylinder 24, whereas movement from the bottom dead center point to the top dead center point is an exhaust or compression stroke during which the piston 27 is inserted into the cylinder 24. Connecting ports 70 and 71 are formed in cylinder 24 respectively in positions in front of the bottom dead center point of the piston 27 and at the top dead center point of the piston 27. The switch plate 75 is located at a position where it opposes openings of ports 70 and 71 in the lateral end surface of cylinder 24. Switch plate 75 is provided with suction port 28 and exhaust port 29 at locations such that they may be connected respectively with connecting ports 70 and 71 during the suction stroke and the exhaust stroke. The opposite end of the suction port 28 communicates with the interior of the cap 6. The exhaust port 29 is connected with tube 66 which leads waste ink to the absorptive pad.

Figure 47:
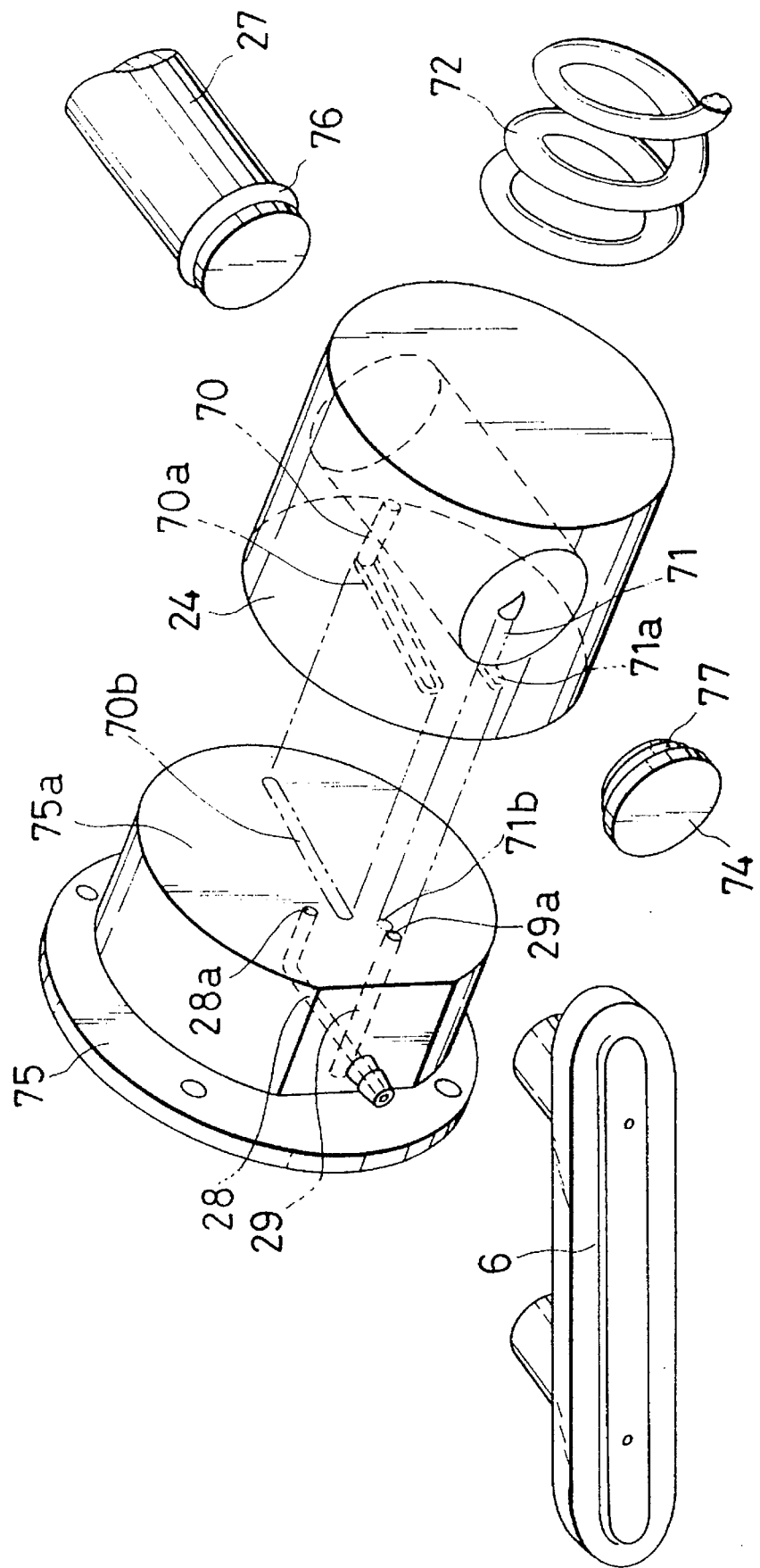
FIG. 47 is an enlarged exploded perspective view showing relationships between a transfer plate and cylinder according to the seventh embodiment.

FIG. 47 is a perspective view illustrating a relationship between the cylinder 24 and the switch plate 75. The cylinder 24 abuts with switch surface 75 a of the switch plate 75 under resilient force of the compression spring 72. Connecting ports 70 and 71 are oriented to extend from the through-hole in the cylinder toward the switch surface 75a. Thus, port 70 may be connected with the suction port 28 on the exhaust stroke of the piston 27, and the port 71 may connect pressure chamber 31 with the exhaust port 29 on the exhaust stroke of the piston 27. The switch surface 75 a and the cylinder 24 may slide relative to each other so that a port may be connected alternatively with the pressure chamber 31. When the cylinder 24 pivots, air may flow into the pressure chamber 31 to thereby reduce a rate of suction in the pressure chamber 31, if a clearance is formed between the switch plate 75 and the cylinder 24. An inflow of air may be avoided by forcing the cylinder 24 to abut with the switch surface 75 a under resilient force of the compression spring 72. The piston 27 is freely slidably inserted into the through-hole in the cylinder 24. The cylinder 24 is freely pivotably received in the through-hole in the cap holder 7. Clearances of about 0.01 millimeter are defined between the cylinder 24 and the piston 27 and between the cap holder 7 and the cylinder 24 through which air may flow into the pressure chamber 31. A seal 76 made from resilient material is applied over the outer diameter of the piston 27, which is then inserted into through-hole in the cylinder 24. The inner diameter of the cylinder 24 and the outer diameter of the piston 27 are such that they may compress the seal 76 slightly. The seal 76 which has been compressed serves to close the clearance to prevent air from flowing along the outer diameter of the piston 27. A seal 77 is applied over a disk 74 which is then inserted into an opposite end of the through-hole in the cylinder 24. The inner diameter of the through-hole in cylinder 24 and the outer diameter of the disk 74 compress the seal 77. Seal 77 which has been compressed serves to close the clearance to prevent air from flowing from the outer diameter of the cylinder 24 into the pressure chamber 31.

To facilitate understanding of relationships in which openings 70a, 71a of connecting ports 70 and 71 may be connected with and disconnected from openings 28a, 29a in surface 75 a of suction and exhaust ports 28, 29, FIG. 47 illustrates projection 70b of opening 70a of ports 70 and projection 71b of opening 71a of port 71. Such projections are on the switch surface 75a.

Figure 54A:
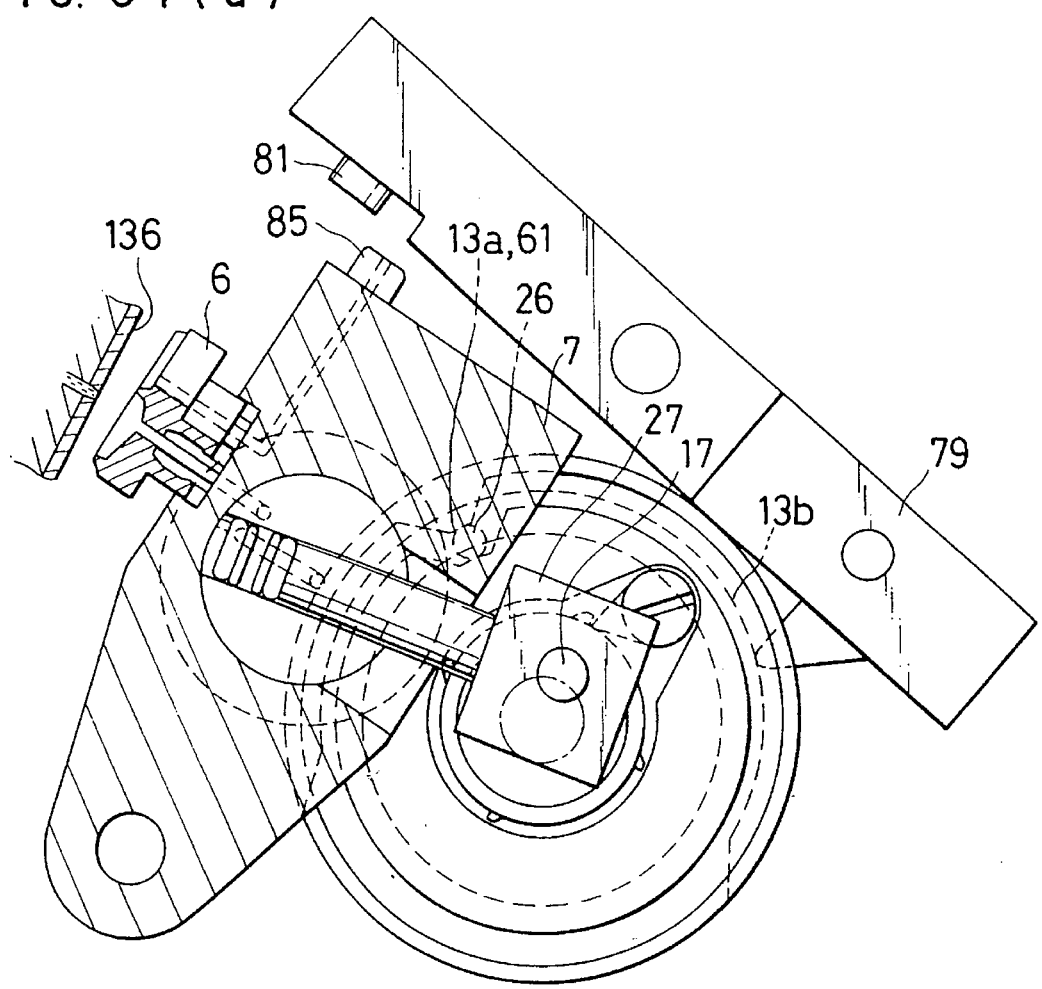
FIGS. 54(a) and 54(b) are similar views, but with the cap holder shown in a stopped state at the starting point of the cam.

The manner of operation of this embodiment of the maintenance station 5 now will be described. As shown in FIG. 54(a), cam follower 26 is initially at the minimum radius portion 61 of the first cam 13a, and the piston 27 is in the compression stroke. The carriage 2 travels to its home position 37. Motor 38 is driven to rotate the cam 13 and the eccentric shaft 7 in the counterclockwise direction. Immediately after the motor 38 is actuated, the cam follower 26 shifts to the maximum radius portion 49 of the first cam 13a, thereby moving the cap 6 into close contact with the ink jet head 1. The cam follower 80 operates following the second cam 13b, and lever 79 is actuated to allow the rubber seat 81 close the atmospheric suction port 85. As cam 13 rotates, ratchet 45 in engagement with first pawl 44a rotates shaft 69 and eccentric shaft 17. The piston 27 further advances, and retracts after completion of the compression stroke to begin the compression stroke. The cylinder 24 rotates in the clockwise direction under actuation of the piston 27 during this period.

Figure 48A:
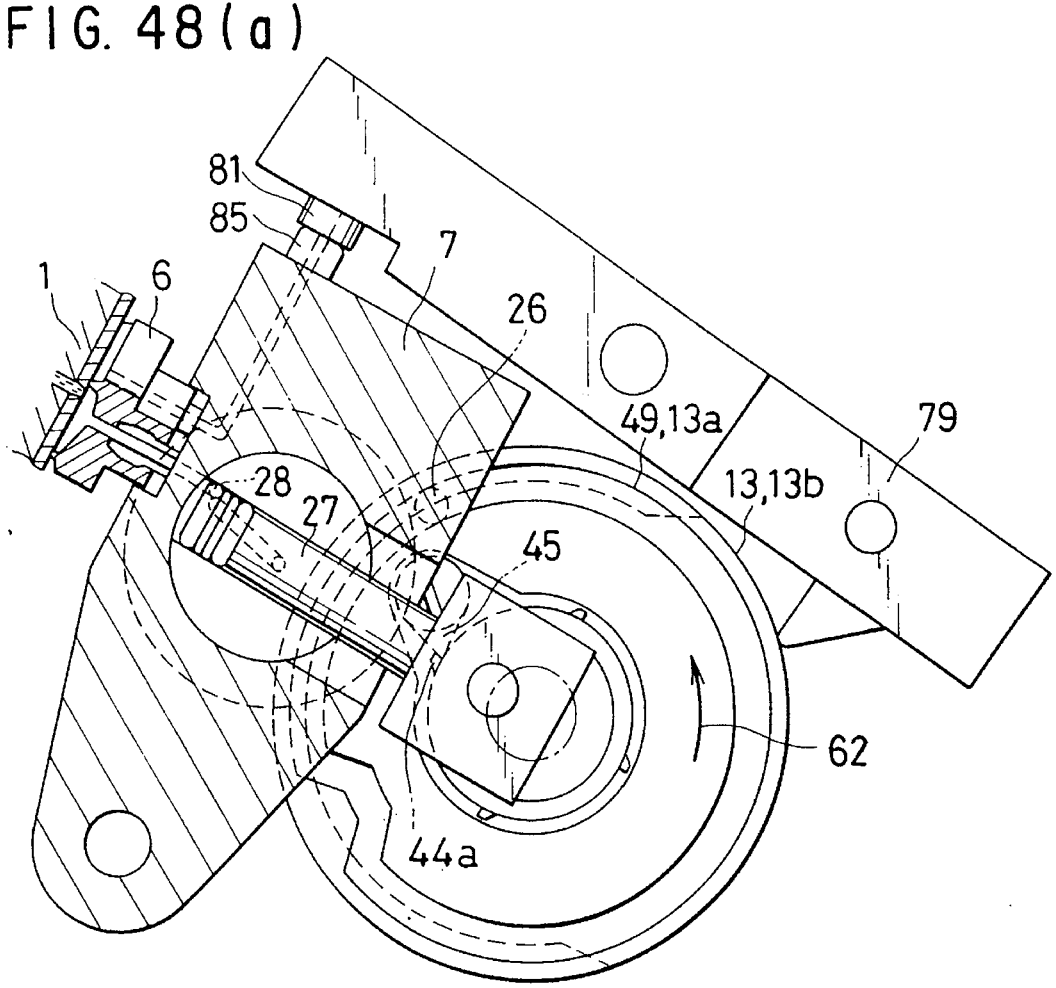
FIGS. 48(a) and 48(b) respectively are a sectional view showing a cap holder according to the seventh embodiment and a projection of communicating ports thereof.

FIG. 48(a) is a cross-sectional view showing the cap holder 7 when the cam 13 rotates through 90° in the counterclockwise direction from the origin of the cam. The cam follower 26 is at the maximum radius portion 49 of the first cam 13, and the cap 6 is in close contact with the ink jet head 1. The layer 79 is at the maximum radius portion of the second cam 13b, and thus the rubber seat 81 closes the atmospheric suction port 85. The piston 27 is at its top dead center point completing the compression stroke. Since suction port 28 is disconnected as described later, the interior of the cap 6 is in communication with the atmosphere. The ink jet printer stops operating under this situation, when its intended application is terminated, and consequently alteration of viscosity of ink, which would otherwise occur due to evaporation of ink components inside the ink jet head 1, can be prevented. Under a usual suction movement, the cam 13 is caused to turn further in the direction of arrow 62, which represents the rotation of the cam. The ratchet 45 is in meshing engagement with the first pawl 44a.

Figure 48B:
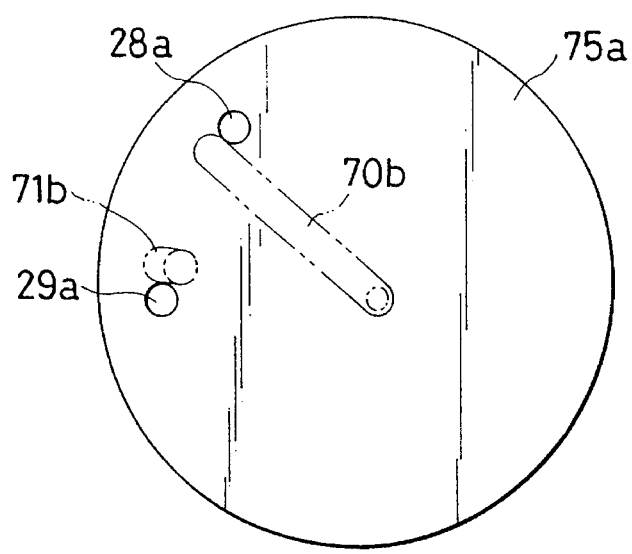

FIG. 48(b) shows switch surface 75 a with cam 13 rotated through 90° from the origin of the cam in the counterclockwise direction. Switch surface 75 a is shown with the suction port opening 28a and the exhaust port opening 29a. The suction port opening 28a and the projection 70b of the opening 70a of connection port 70 are disconnected, and the exhaust port opening 29a and the projection 71b of opening 71a of connection port 71 also are disconnected.

Figure 49A:
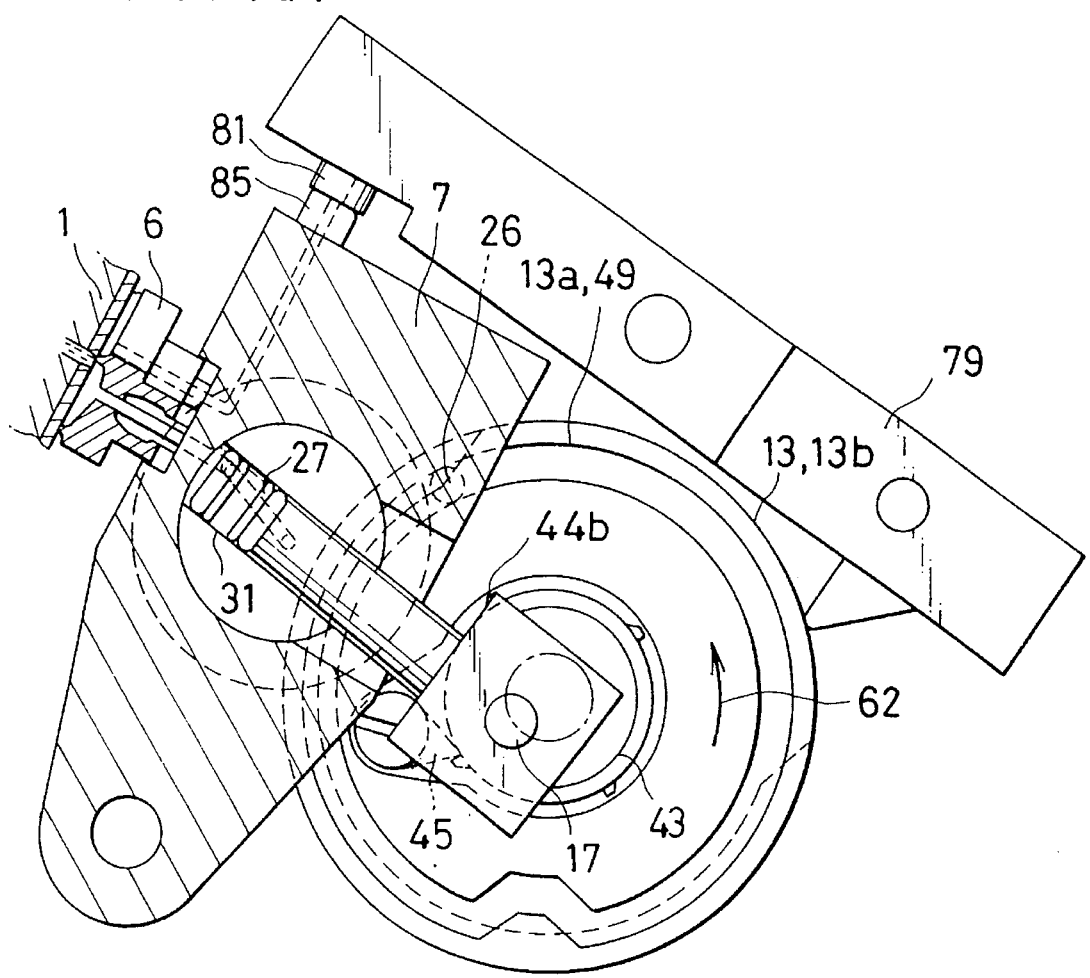
FIGS. 49(a) and 49(b) are similar views, but with the cap holder just before a first reverse rotation of the cam.

FIG. 49(a) is a cross-sectional view showing the cap holder 7 when the cam 13 has rotated through 150° from the origin in the counterclockwise direction. The cam follower 26 is at the maximum radius portion 49 of the first cam 13a, and the cap 6 is in close contact with the ink jet head 1. The lever 79 is at the maximum radius portion of the second cam 13b, and the rubber seat 81 closes the atmospheric air suction port 85. The piston 27 has passed through the top dead center point and entered into the suction stroke so that pressure chamber 31 is formed. When the motor 38 is rotated in the reverse direction by the control system (not shown), the cam 13 may rotate in the reverse direction. However, the one-way clutch 43 is operative to prevent shaft 69 from rotating, and thus the eccentric shaft 17 remains stationary. When the cam 13 reversely rotates through 100° in the clockwise direction, the ratchet 45 will override the second pawl 44b. During this operation, the cam follower 26 is at the maximum radius portion 49 of the first cam 13a, and thus it is possible for the cap 6 to maintain inclose contact with the ink jet head 1. When the motor 38 is caused to rotate in the normal direction by means of the control system (not shown), the cam 13 begins rotating in the direction of arrow 62, and ratchet 45 meshes with the second pawl 44b. Thereby, eccentric shaft 17 is rotated in the counterclockwise direction.

Figure 49B:
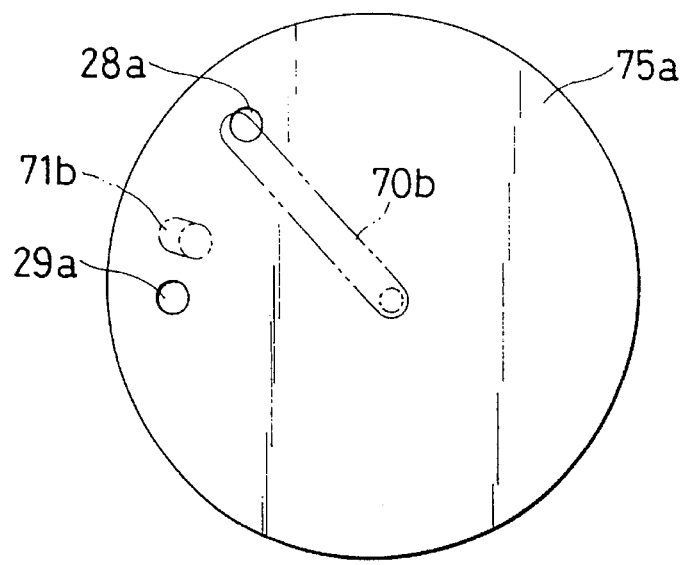

FIG. 49(b) shows the switch surface 75 a when the cam 13 rotates through 150° in the counterclockwise direction to a condition shown in FIG. 49(a). The suction port opening 28a is connected with the projection 70b of opening 70a connecting port 70. The exhaust port opening 29a remains disconnected from the projection 71b of the opening 71a of the connecting port 71.

Figure 50A:
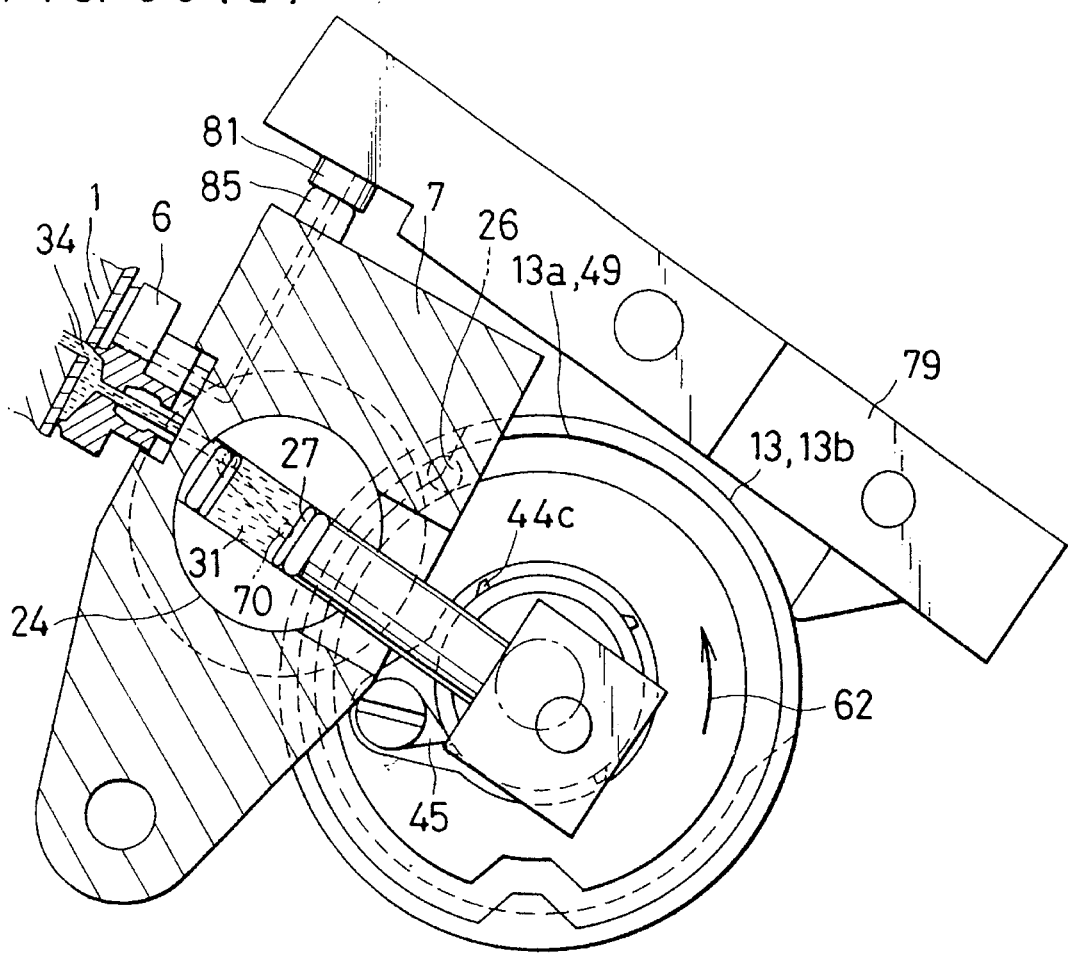

FIG. 50(a) is a cross-sectional view showing the cap holder 7 after the cam 13 has rotated through 150° from the original point in the counterclockwise direction, then rotated once through 100° in the clockwise direction and then rotated through 100° in the counterclockwise direction. Since the cam follower 26 is at the maximum radius portion 49 of the first cam 13a, the cap 6 is in close contact with the ink jet head 1. The lever 79 is at the maximum radius portion of the second cam 13b, and thus the rubber seat 81 closes the atmospheric air suction port 85. The connection port 70 has already been connected with the suction port 28, and when the tip end of the piston 27 passes through the connecting port 70, ink inside the ink jet head 1 is withdrawn into chamber 31 in the cylinder 24 via the connection port 70 and the suction port 28. In order to withdraw the ink by breaking the ink meniscus of the nozzle holes 34, the pressure chamber 31 is connected with the cap 6 after a sufficient vacuum pressure has been created inside pressure chamber 31. In this way, while old ink is withdrawn through the nozzle holes 34 which have not been used for long periods of time, air bubbles contained inside the ink jet head 1 are simultaneously discharged, thereby to recover the function of delivering ink liquids. Then, the cam 13 is reversed through 100° in the clockwise direction. The ratchet 45 will override the third pawl 44c. The cam 13 is rotated in the direction of arrow 62 which represents the rotation of the cam, and the ratchet 45 meshes with the third pawl 44c. The eccentric shaft 17 thus rotates in the normal direction, and the piston 27 enters the suction stroke following the compression stroke. During this operation, the cylinder 24 may rotate in the counterclockwise direction.

Figure 50B:
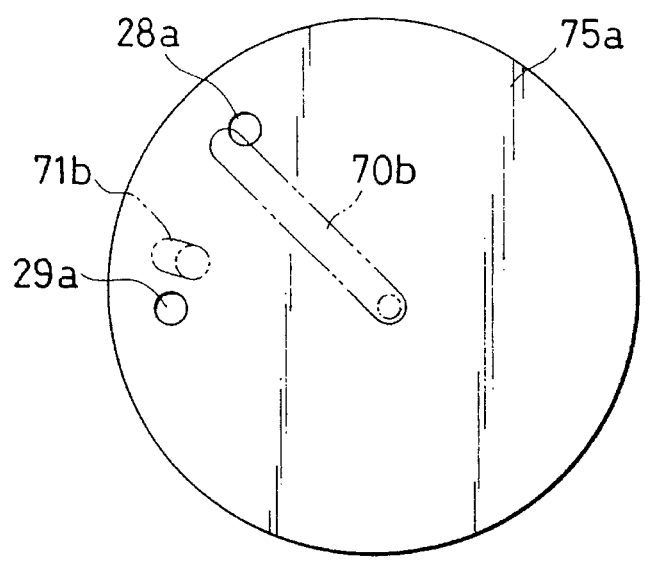

FIG. 50(b) is a cross-sectional view showing the switch surface 75a, after the cam 13 has rotated through 150° from the origin in the counterclockwise direction, then rotated through 100° once in the clockwise direction and through 100° in the counterclockwise direction. The suction port opening 28a is connected with the projection 70b of the opening 70a of the connecting port 70. The exhaust port opening 29a is disconnected from the projection 71b of the opening 71a of the connection port 71.

Figure 51A:
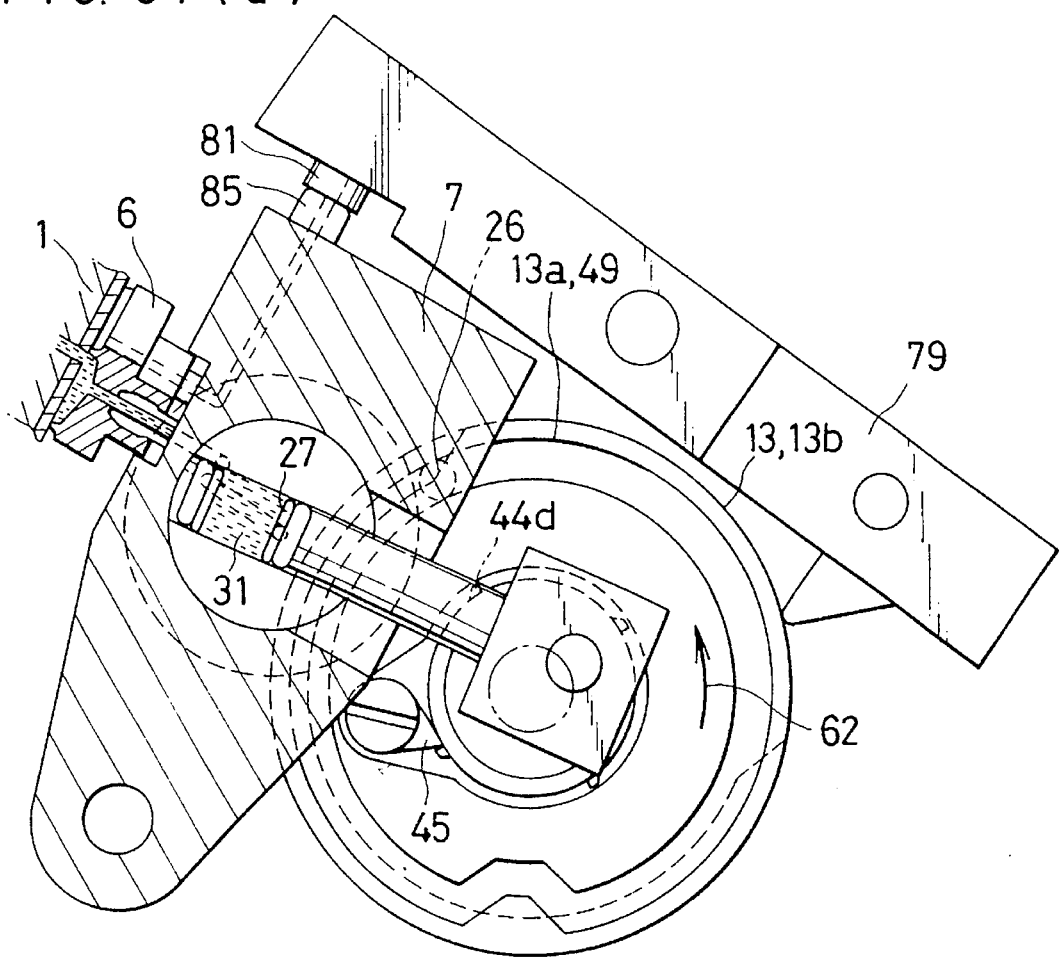
FIGS. 51(a) and 51(b) are similar views, but with the cap holder just before a third reverse rotation of the cam.

FIG. 51(a) is a cross-sectional view showing the cap holder 7 after the cam 13 has rotated through 150° from the original point in the counterclockwise direction, then rotated twice through 100° in the clockwise direction and rotated through 100° in the counterclockwise direction. Since the cam follower 26 is at the maximum radius portion 49 of the first cam 13a, and the cap 6 is in close contact with the ink jet head 1. The lever 79 is at the maximum radius portion of the second cam 13b, and thus the rubber seat 81 closes the atmospheric air suction port 85. The piston 27 has passed through the bottom dead center point and is on the compression stroke, and the exhaust port 29 is in communication with the pressure chamber 31, thereby allowing ink to be discharged to an ink absorbent (not shown) through the tube 66. Then, the cam 13 rotates through 100° in the clockwise direction. The ratchet 45 will override the fourth pawl 44d. The cam 13 rotates in the direction of arrow 62 and the ratchet 45 will mesh with the fourth pawl 44d.

Figure 51B:
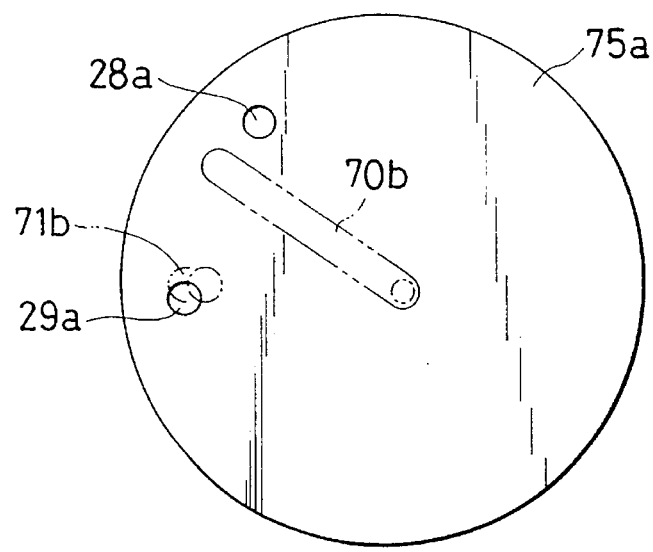

FIG. 51(b) is a view showing the switch surface 75a after the cam 13 has rotated through 150° from the original point in the counterclockwise direction, then rotated twice through 100° in the clockwise direction and rotated through 100° in the counterclockwise direction. The suction port opening 28a is disconnected from the projection 70b of the opening 70a of the connecting port 70. The exhaust port opening 29a is connected with the projection 71b of the opening 71a of the connecting port 71.

Figure 52A:
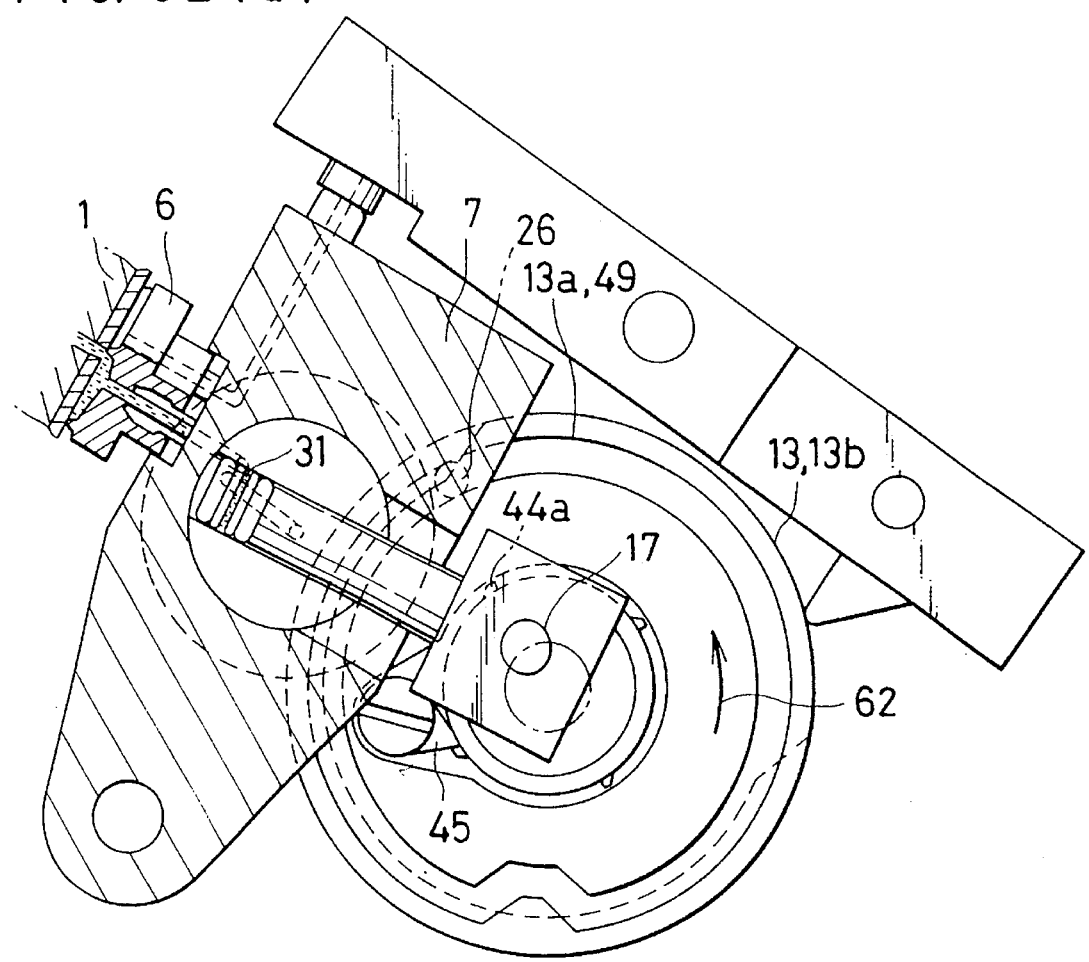
FIGS. 52(a) and 52(b) are similar views, but with the cap holder just before a fourth reverse rotation of the cam.

FIG. 52(a) is a cross-sectional view showing the cap holder 7 after the cam 1 has rotated through 150° from the original point in the counterclockwise direction, then rotated three times through 100° in the clockwise direction and rotated through 100° in the counterclockwise direction. Ink inside the pressure chamber 31 is discharged to the ink absorbent (not shown) by flowing through the exhaust port 29 and the tube 66. Since the cam follower 26 is at the maximum radius portion 49 of the first cam 13a, the cap 6 is in close contact with the ink jet head 1. The cap 6, the suction port 28 and the connecting port 70 are internally filled with ink. Then the cam 13 rotates through 100° in the clockwise direction. The ratchet 45 will override the first pawl 44a. The cam 13 rotates in the counterclockwise direction, and the ratchet 45 will mesh with the first pawl 44a. The eccentric shaft 17 rotates in conjunction with the cam 13, and when the piston 27 has passed through the top dead center point while discharging ink from the pressure chamber 31, the exhaust port 29 is disconnected from the pressure chamber 31 to create a vacuum pressure inside the pressure chamber 31. The suction port 28 may be connected with the connecting port 70.

Figure 52B:
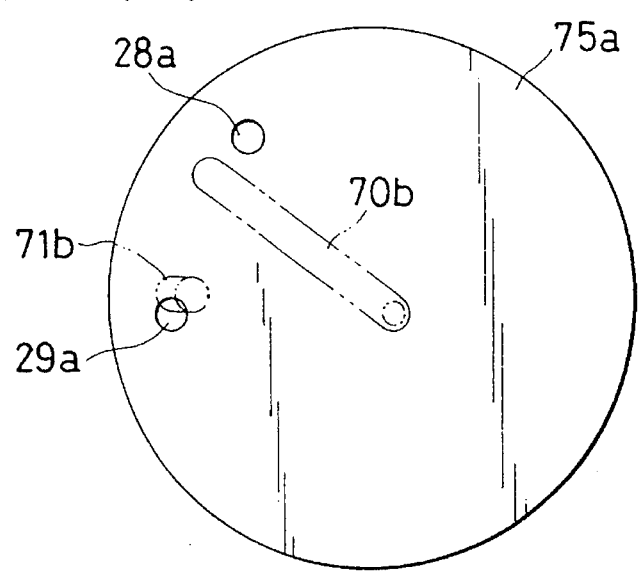

FIG. 52(b) is a view showing the switch surface 75a after the cam 13 has rotated through 150° from the original point in the counterclockwise direction, then rotated three times through 100° in the clockwise direction and rotated through 100° in the counterclockwise direction. The suction port opening 28a is disconnected from the projection 70b of the opening 70a of the connecting port 70. The exhaust port opening 29a is connected with the projection 71b of the opening 71a of the connecting port 71.

Figure 53A:
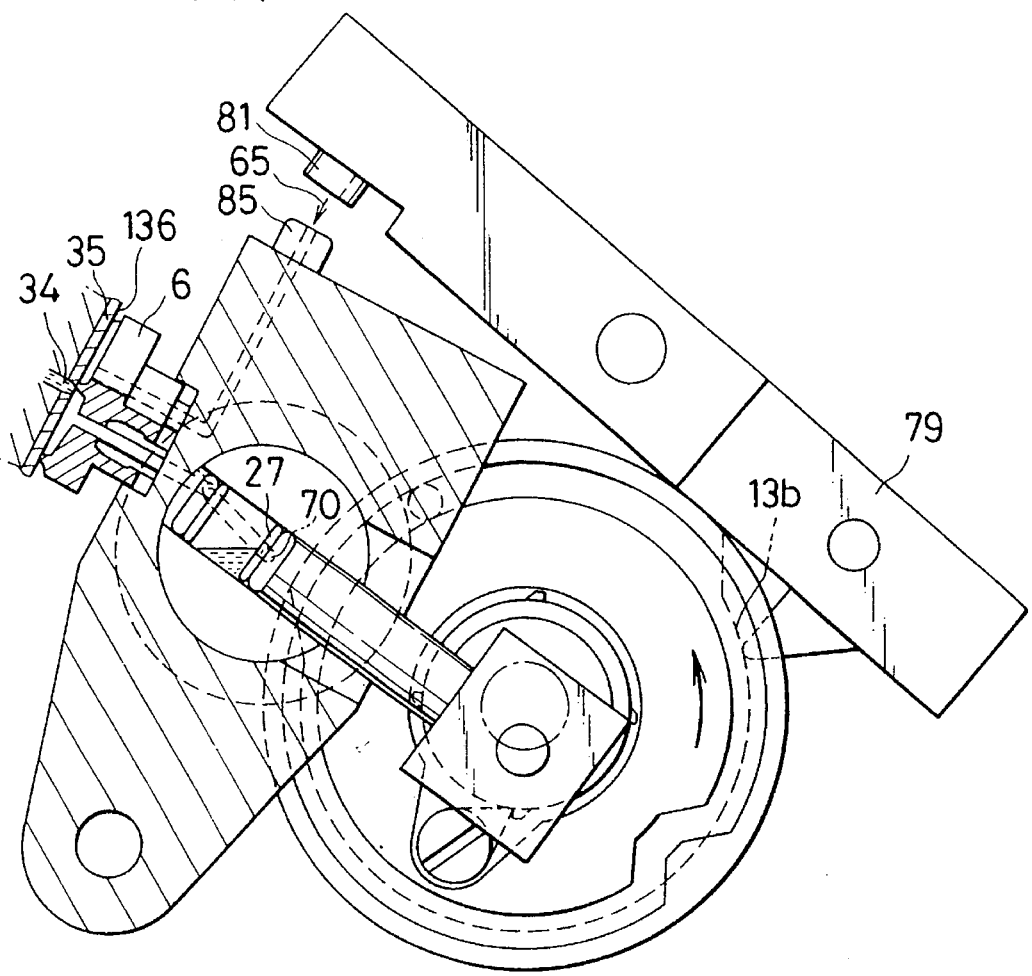
FIGS. 53(a) and 53(b) are similar views, but with the cap holder shown in a suction state.

FIG. 53(a) is a cross-sectional view showing the cap holder 7 after the cam 13 has further continued rotating from the state shown in FIG. 52(a) in a normal direction by rotating through 200° from the original point in the counterclockwise direction. The radius of the cam is altered at a position where the cam has rotated through 180° from its origin, and the lever 79 is at the minimum radius portion of the second cam 13b so that the rubber seat 81 moves away from the atmospheric air suction port 85. Upon further rotation of the cam through 50°, the piston 27 passes through the connecting port 70 to withdraw air through atmospheric air suction port 85 as shown by arrow 65. Thus, ink is withdrawn from the suction port 28 and the connecting port 70, in conjunction with ink from nozzle surface 136 and the interior of the cap 6. Wiping of nozzle surface 136 is needed to remove therefrom ink and waste paper which might deposit on nozzle plate 35, thereby to ensure that the ink will fly in the correct direction to improve printing quality. However, when the nozzle 35 upon which ink has become stuck is wiped, then the ink may be scraped toward the nozzle holes 34 to thereby form an ink reservoir in which air bubbles are contained. Because the ink inside the ink jet head 1 is at a negative pressure, such ink in which air bubbles are contained is withdrawn into the interior. Accordingly, ink drops may not be delivered through nozzle holes 34 through which such air bubble containing ink has been suctioned.

After the ink is suctioned through the ink jet head 1, the delivery direction of the ink may not be disturbed due to the ink which remains adjacent to the nozzle holes 34, and air bubbles may not be entrapped in the ink jet head 1 even if the ink wiping action is effectuated. Therefore, it will not be necessary to provide a mechanism for shifting the wiper 39. Besides, since the ink may be removed from the cap 6 and the suction port 28 in which the ink has been filled, it is possible to force the ink into the interior of the ink jet head 1 and thereby prevent ink drops from being delivered therefrom utilizing a capillary action pressure of the ink inside the cap 6 and the suction port 28 upon a subsequent capping operating.

Figure 53B:
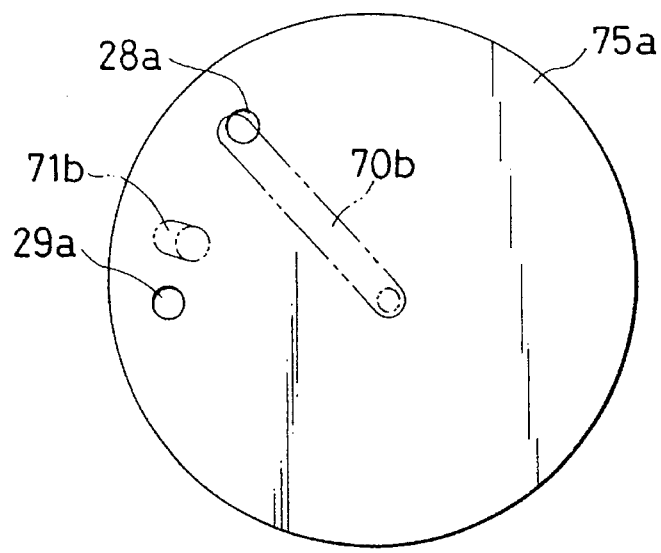

FIG. 53(b) is a view showing the switch surface 75a with the situation as shown in FIG. 53(a). The suction port opening 28a is connected with the projection 70b of the opening 70a of the connecting port 70. The exhaust port opening 29a is disconnected from the projection 71b of the opening 71a of the connecting port 71.

Upon the cam 13 being further rotated, the cam 13 will have rotated through a full turn from its original position and returned to its origin. During such time, the eccentric shaft 17 will have rotated twice from its original position and returned thereto.

FIG. 54(a) is a cross-sectional view showing the cap holder 7 at the origin of the cam. The cam follower 26 is at the minimum radius portion 61 of the first cam 13a, and the cap 6 has moved away from the nozzle surface 136. The lever 79 is at the minimum radius portion of the second cam 13b, and the rubber seat 81 has moved away from the atmospheric air suction port 85. The eccentric shaft 17 is intermediate in an operable range of the piston 27 and will not interfere with the tip end of the piston 27, even when the cap holder 7 is retracted. The cap holder 7 will move away from the nozzle surface 136 to its extreme retracted position when the cam rotates approximately through 20°, but the pressure chamber 31 may be simultaneously and suddenly compressed. Since the connecting port 71 is connected with the exhaust port 29, the ink may be discharged from the pressure chamber 31 through the tube 66. The ink jet head 1 may reciprocate between the home position 37 and the printing position to wipe the nozzle surface 136 by means of the wiper 39. The ink jet head 1 can terminate its reciprocating movement, and thus the ink jet head 1 can continue or terminate its printing action. In the case of the ink jet printer being stopped, the head will return again to its home position 37 to thereby actuate the maintenance station 5.

Figure 54B:
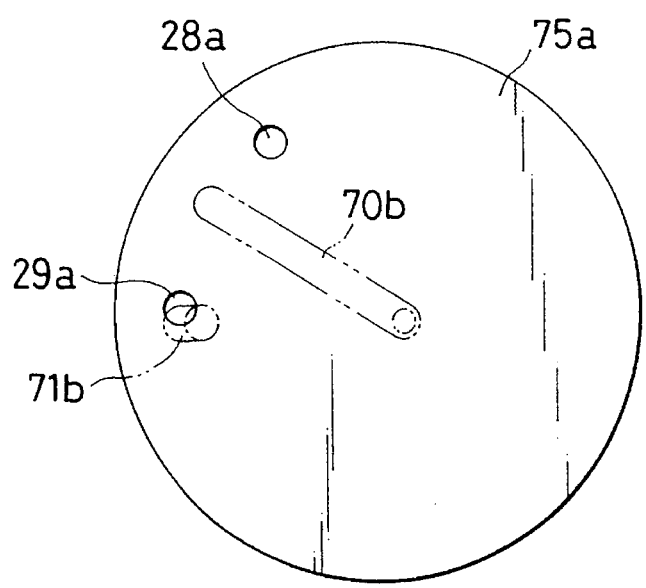

FIG. 54(b) is a view showing the switch surface 75 a at the origin of the cam. The suction port opening 28a is disconnected from the projection 70b of the opening 70a of the connecting port 70. The exhaust port opening 29a is connected with the projection 71b of the opening 71a of the connecting port 71.

Figure 55:
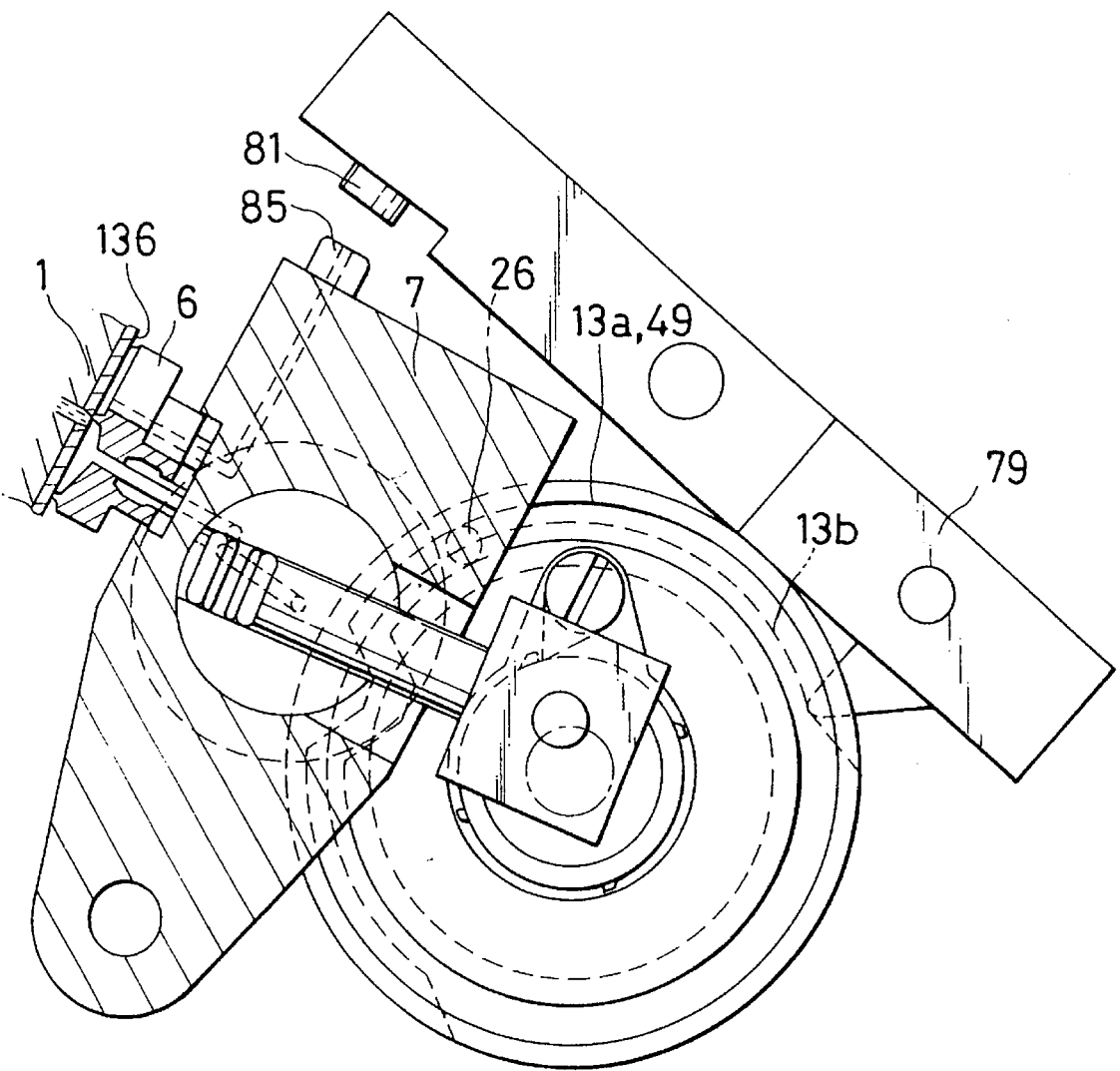
FIG. 55 is a sectional view of the cap holder with an inner part of the cap open to the atmosphere.
Figure 56:
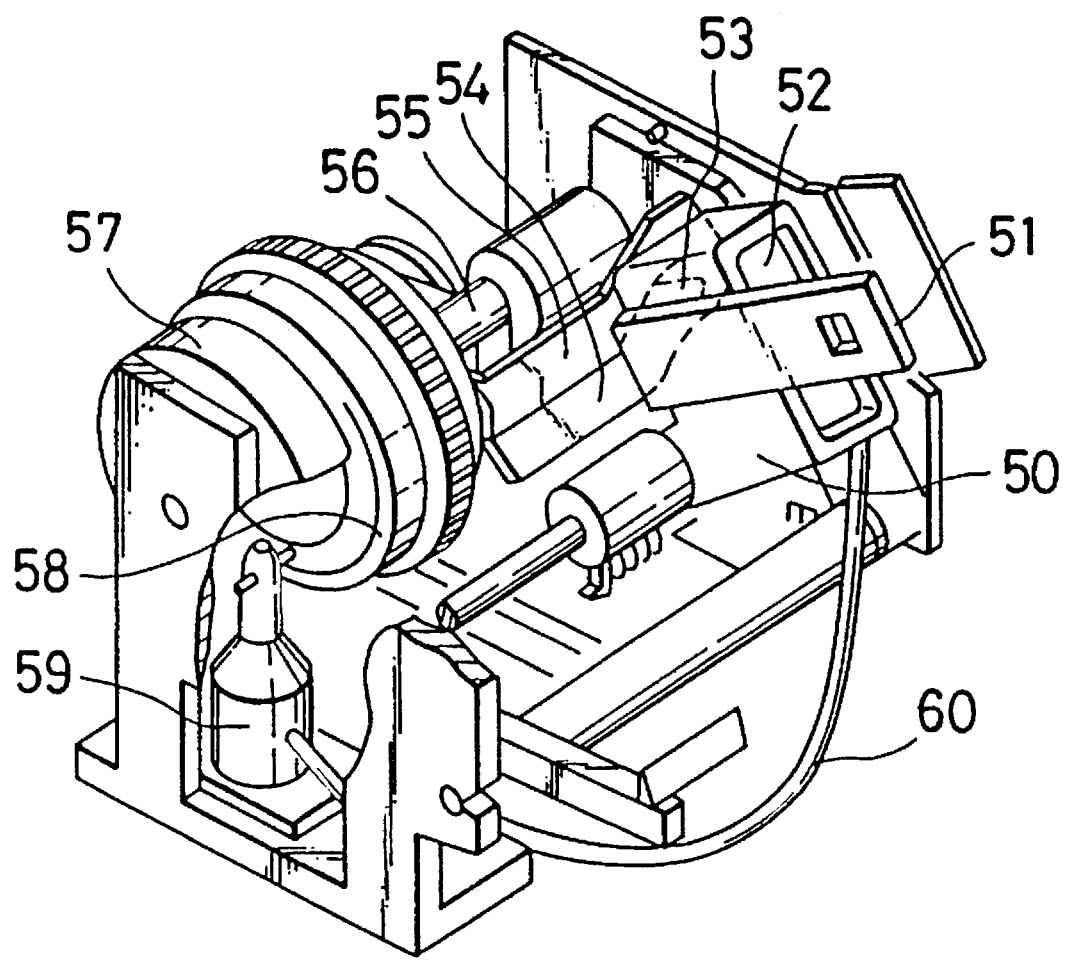
FIG. 56 is a perspective view of a conventional maintenance station.

FIG. 55 is a cross-sectional view showing the cap holder 7 after the cam 13 has rotated through 45° from the origin of the cam in the counterclockwise direction. The cam follower 26 is at the maximum radius portion 49 of the first cam 13a, and the cap 6 is in close contact with the nozzle surface 136 of the ink jet head 1. After the cap 6 comes into close contact with the nozzle surface 136 during a capping sequence, then the cap is depressed further approximately 0.5 mm, and the internal capacity of the cap 6 is reduced. However, the lever 79 is at the minimum radius portion of the second cam 13b, and the rubber seat 81 is separated from the atmospheric air suction port 85. Therefore, the internal pressure of the cap 6 will not be increased, thereby preventing air bubbles from being entrapped into the ink jet head 1. After the capping procedure, the lever 79 may move to the maximum radius portion of the second cam 13b to cause the rubber seat 81 to close the atmospheric suction port 85.

Because the maintenance station of the present embodiment is designed to actuate the pump multiple times every time when the cap 6 opens and closes, when a used ink cartridge is replaced with a new one, then a suction procedure which may be suitable to fill the ink jet head 1 with the ink can be realized. For instance, after the cam is rotated through 150° in a normal counterclockwise direction from the origin, then is reversed through 100° to return to position the 50° spaced from the origin, such may be followed by a reciprocating movement between 50° and 100° to thereby rotate the eccentric shaft 17 plural times in the normal direction. Thus, the cap 6 is connected with the ink jet 1, and the atmospheric suction port 85 is closed with the rubber seat 81 of the lever 79. The piston 27 is driven to repeat its suction and compression movements while the interior of the cap 6 is disconnected from atmospheric air, so that air may be efficiently sucked out of the ink jet head so as to allow the ink jet head to be filled with the ink.

Describing this operation with reference to the drawings, as the cam 13 is caused to rotate through 150° from the origin in the clockwise direction, the maintenance station may be put in such a mode as shown in FIG. 49(a) as above-described. Then, the cam 13 is caused to reverse through 100° in the clockwise direction and then is rotated through 100° in a normal direction. The situation as shown in FIG. 50(a) can be provided, as above-described. By repeating similar procedures subsequently, the cam may realize a situation as shown in FIG. 52(a) passing through the mode as shown in FIG. 51(a). The situation as shown in FIG. 49(a) may be recovered by driving the cam 13 to rotate and reverse. During this operation, the eccentric shaft 17 is caused to rotate through one-full turn, and the piston 27 is driven to complete suction and compression strokes of the pump. By repeating rotation and reverse rotation of the cam 13 in a similar fashion, the cap 6 may be connected with the ink jet head 1 to allow the atmospheric air suction port 85 to be closed by the rubber seat 81 of the lever 79. Thus, the eccentric shaft 17 may be rotated plural times to repeat suction and compression of the pump while the interior of the cap 6 is disconnected from atmospheric air.

As above-described, the present embodiment has advantages similar to those to be provided in the sixth embodiment, and furthermore the abutment of the cylinder 24 against the surface of the switch plate 75 may eliminate the clearance to be created between the suction port out let 28a, the opening 29a in the exhaust port and the cylinder 24.

Moreover, by attaching the seal 76 to the piston 27, the pump air tightness can be increased to thereby improve suction efficiency.

In accordance with the present invention, the pump is incorporated into the cap holder utilizing a construction that has never been employed in the prior art. Thus, a simple and compact construction can be provided, in comparison with the conventional arrangement of the prior art ink jet printer in which the cap for the maintenance station, the cap holder, the atmospheric air release valve, the suction pump and the cam are independently provided in order to ensure a constant level of printing quality. The cap can be communicated with the cylinder after an adequate level of vacuum pressure has been established in the cylinder, and therefore is made available to withdraw ink inside the nozzle with an increased suction greater than the pressure of capillary action thereof. Thus, the ink can be withdrawn more forcibly by breading the meniscus thereof. In this manner, old ink can be withdrawn from the ink jet head, even if the head has not been used for a long period of time, and a recovery action can be taken in a reliable manner. In comparison with the convention approach, the length and the capacity of the suction path can be reduced to thereby increase the vacuum pressure for withdrawal, resulting in a very powerful suction. Since the ink which remains on the nozzle surface after the ink has been suctioned from the ink jet head can be removed effectively without manual intervention, it is possible to clean up the nozzle surface and prevent difficulties which would otherwise occur due to a wiping action. Because the pump can be operated in plural times every time when the cap is opened or closed, it therefore is possible to withdraw the ink in a suitable manner that may allow the ink jet head to be filled with ink after replacement of an ink cartridge.

I claim:

1. In an ank jet printer including a paper delivery mechanism, an ink jet head mounted on a carriage and movable thereby along recording paper at said paper delivery mechanism to jet ink through at least one nozzle hole to perform printing and movable to a stop home position, and a maintenance station at said home position to perform a maintenance recovery operation on said ink jet head, the improvement wherein said maintenance station comprises:

a cap to achieve capping of said at least one nozzle hole when said ink jet head is in said home position;

a pump including a casing having therein a cylindrical guide opening, a cylinder comprising a cylindrical member mounted in said cylindrical guide opening, said cylindrical member having therethrough a cylindrical passage, and a piston slidable in opposite directions in said cylindrical passage for suction and compression strokes;

separate suction and discharge holes in said pump;

a power source; and a piston drive operably connected to said power source and to said piston to move said piston in said opposite directions in said cylindrical passage, to connect a pressure chamber in said pump via said suction hole to said cap during said suction stroke, and to connect said pressure chamber via said discharge hole to the exterior during said compression stroke.

2. The improvement claimed in claim 1, wherein said power source comprises a member rotatable about a longitudinal axis, and said piston drive comprises an eccentric member positioned eccentrically of said axis and rotatable in an orbit thereabout.

3. The improvement claimed in claim 2, wherein a first end of said piston extends into said cylindrical passage in said cylindrical member, and a second end of said piston is connected to said eccentric member and is rotatable in said orbit therewith, as a result of which said first end of said piston moves in said opposite directions in said cylindrical passage in said cylindrical member and said cylindrical member reciprocally rotates in opposite directions within said cylindrical guide opening in said casing.

4. The improvement claimed in claim 3, wherein said suction and discharge holes extend outwardly through said casing from said cylindrical guide opening therein at positions spaced circumferentially of said cylindrical guide opening.

5. The improvement claimed in claim 1, wherein said cylindrical passage extends transverse to said cylindrical guide opening.

6. The improvement claimed in claim 1, further comprising a cap holder mounted for movement toward and away from said ink jet head, said cap holder supporting said cap at a position to cap said at least one nozzle hole when said cap holder is moved toward said ink jet head and to release capping when said cap holder is moved away from said ink jet head.

7. The improvement claimed in claim 6, wherein said power source comprises a cam member rotatable about an axis and having a cam surface having plural portions spaced different distances from said axis.

8. The improvement claimed in claim 7, further comprising a cam follower on said cap holder and engaging said cam surface such that rotation of said cam member about said axis moves said cap holder toward and away from said ink jet head.

9. The improvement claimed in claim 6, wherein said cap holder has formed therein a cylindrical guide opening, said cylinder comprises a cylindrical member mounted in said cylindrical guide opening, said cylindrical member has therethrough a cylindrical passage, and said piston slides in said opposite directions within said cylindrical passage.

10. The improvement claimed in claim 9, wherein said power source comprises a member rotatable about a longitudinal axis, and said piston drive comprises an eccentric member positioned eccentrically of said axis and rotatable in an orbit thereabout.

11. The improvement claimed in claim 10, wherein a first end of said piston extends into said cylindrical passage in said cylindrical member, and a second end of said piston is connected to said eccentric member and is rotatable in said orbit therewith, as a result of which said first end of said piston moves in said opposite directions in said cylindrical passage in said cylindrical member and said cylindrical member reciprocally rotates in opposite directions within said cylindrical guide opening in said cap holder.

12. The improvement claimed in claim 11, wherein said suction and discharge holes extend outwardly through said cap holder from said cylindrical guide opening therein at positions spaced circumferentially of said cylindrical guide opening.

13. The improvement claimed in claim 12, wherein said pressure chamber is created within said cylindrical passage by movement of said piston in one said direction therein during said suction stroke, and further comprising a connecting hole extending through said cylindrical member from said cylindrical passage therein to an exterior cylindrical surface thereof, whereby movement of said cylindrical member in one direction in said cylindrical guide opening brings said connecting hole into communication with said suction hole and moves said pressure chamber out of communication with said discharge hole, and whereby movement of said cylindrical member in an opposite direction in said cylindrical guide opening moves said connecting hole out of communication with said suction hole and brings said pressure chamber into communication with said discharge hole.

14. The improvement claimed in claim 13, further comprising a connecting recess in said exterior cylindrical surface of said cylindrical member, and an atmosphere port extending through said cap holder from said cylindrical guide opening therein to the exterior, said cylindrical member being movable in said cylindrical guide opening to bring said suction hole into communication with said atmosphere port through said connecting recess.

15. The improvement claimed in claim 11, further comprising a switch plate closing one end of said cylindrical guide opening and maintaining said cylindrical member therein, and said suction and discharge holes extend outwardly through said switch plate from an inner surface thereof.

16. The improvement claimed in claim 15, wherein said pressure chamber is created within said cylindrical passage by movement of said piston in one said direction therein during said suction stroke, and further comprising a connecting hole extending through said cylindrical member from said cylindrical passage therein to an exterior surface thereof, whereby movement of said cylindrical member in one direction in said cylindrical guide opening brings said connecting hole into communication with said suction hole and moves said pressure chamber out of communication with said discharge hole, and whereby movement of said cylindrical member in an opposite direction in said cylindrical guide opening moves said connecting hole out of communication with said suction hole and brings said pressure chamber into communication with said discharge hole.

17. The improvement claimed in claim 16, wherein said inner surface of said switch plate and said exterior surface of said cylindrical member comprise abutting planar surfaces.

18. The improvement claimed in claim 16, further comprising another connecting hole extending through said cylindrical member from said cylindrical passage therein to said exterior surface thereof to be brought into communication with said discharge hole.

19. The improvement claimed in claim 6, further comprising a connecting hole extending through said cap holder from said cap to an air inlet leading to the exterior, and a closure closing said air inlet when said cap caps said at least one nozzle.

20. The improvement claimed in claim 19, wherein said power source comprises a cam member rotatable about an axis and having cam surfaces each having plural portions spaced different distances from said axis, and said closure is on a lever mounted pivotably on said cap holder, said lever having a cam follower engaging one of said cam surfaces such that rotation of said cam member about said axis pivots said lever to move said closure toward and away from said air inlet.

21. The improvement claimed in claim 1, wherein said power source comprises a cam member rotatable in opposite directions about an axis, and said piston drive comprises a drive member rotatable about said axis with said cam member in a first said direction, and a unidirectional drive transfer device transferring rotation of said cam member in said first direction to said drive member and preventing transfer to said drive member of rotation of said cam member in a second opposite said direction.

22. The improvement claimed in claim 21, wherein said piston drive further comprises an eccentric shaft on said drive member at a position eccentrically of said axis, said eccentric shaft rotatable with said drive member in said first direction in an orbit about said axis, said piston being connecting to said eccentric shaft.

23. The improvement claimed in claim 21, wherein said unidirectional drive transfer device comprises a one-way clutch mounted between said cam member and said drive member.

24. The improvement claimed in claim 23, wherein said unidirectional drive transfer device further comprises a plurality of cogs spaced about said drive member, and a ratchet mounted on said cam member and engageable with a said cog in said first direction of rotation of said cam member and operable to pass over said cogs upon rotation of said cam member in said second direction.

25. The improvement claimed in claim 23, wherein said unidirectional drive transfer device further comprises a drive spring having a length portion extending peripherally around said drive member and opposite ends fixed to said cam member, a fixedly positioned plate, and a control spring having a length portion extending peripherally around said drive member and opposite ends fixed to said plate.

26. The improvement claimed in claim 21, wherein said unidirectional drive transfer device comprises a plurality of cogs spaced about said drive member, and a ratchet mounted on said cam member and engageable with a said cog in said first direction of rotation of said cam member and operable to pass over said cogs upon rotation of said cam member in said second direction.

27. The improvement claimed in claim 26, wherein said unidirectional drive transfer device further comprises a plate spring fixedly mounted to engage a said cog upon rotation of said drive member in said second direction.

28. The improvement claimed in claim 21, wherein said unidirectional drive transfer device comprises a drive spring having a length portion extending peripherally around said drive member and opposite ends fixed to said cam member, a fixedly positioned plate, and a control spring having a length portion extending peripherally around said drive member and opposite ends fixed to said plate.

29. A maintenance station for use in an ink jet printer to perform a maintenance recovery operation on an ink jet head thereof, said maintenance station comprising:

a cap to achieve capping of at least one nozzle hole of the ink jet head;

a pump including a casing having therein a cylindrical guide opening, a cylinder comprising a cylindrical member mounted in said cylindrical guide opening, said cylindrical member having therethrough a cylindrical passage, and a piston movable in opposite directions in said cylindrical passage for suction and compression strokes;

separate suction and discharge holes in said pump;

a power source; and a piston drive operably connected to said power source and to said piston to move said piston in said opposite directions in said cylindrical passage, to connect a pressure chamber in said pump via said suction hole to said cap during said suction stroke, and to connect said pressure chamber via said discharge hole to the exterior during said compression stroke.

30. A maintenance station as claimed in claim 29, wherein said power source comprises a member rotatable about a longitudinal axis, and said piston drive comprises an eccentric member positioned eccentrically of said axis and rotatable in an orbit thereabout.

31. A maintenance station as claimed in claim 30, wherein a first end of said piston extends into said cylindrical passage in said cylindrical member, and a second end of said piston is connected to said eccentric member and is rotatable in said orbit therewith, as a result of which said first end of said piston moves in said opposite directions in said cylindrical passage in said cylindrical member and said cylindrical member reciprocally rotates in opposite directions within said cylindrical guide opening in said casing.

32. A maintenance station as claimed in claim 31, wherein said suction and discharge holes extend outwardly through said casing from said cylindrical guide opening therein at positions spaced circumferentially of said cylindrical guide opening.

33. A maintenance station as claimed in claim 29, wherein said cylindrical passage extends transverse to said cylindrical guide opening.

34. A maintenance station as claimed in claim 29, further comprising a cap holder mounted for movement toward and away from said ink jet head, said cap holder supporting said cap at a position to cap said at least one nozzle hole when said cap holder is moved toward said ink jet head and to release capping when said cap holder is moved away from said ink jet head.

35. The improvement claimed in claim 34, wherein said power source comprises a cam member rotatable about an axis and having a cam surface having plural portions spaced different distances from said axis.

36. A maintenance station as claimed in claim 35, further comprising a cam follower on said cap holder and engaging said cam surface such that rotation of said cam member about said axis moves said cap holder toward and away from said ink jet head.

37. A maintenance station as claimed in claim 34, wherein said cap holder has formed therein a cylindrical guide opening, said cylinder comprises a cylindrical member mounted in said cylindrical guide opening, said cylindrical member has therethrough a cylindrical passage, and said piston slides in said opposite directions within said cylindrical passage.

38. A maintenance station as claimed in claim 37, wherein said power source comprises a member rotatable about a longitudinal axis, and said piston drive comprises an eccentric member positioned eccentrically of said axis and rotatable in an orbit thereabout.

39. A maintenance station as claimed in claim 38, wherein a first end of said piston extends into said cylindrical passage in said cylindrical member, and a second end of said piston is connected to said eccentric member and is rotatable in said orbit therewith, as a result of which said first end of said piston moves in said opposite directions in said cylindrical passage in said cylindrical member and said cylindrical member reciprocally rotates in opposite directions within said cylindrical guide opening in said cap holder.

40. A maintenance station as claimed in claim 39, wherein said suction and discharge holes extend outwardly through said cap holder from said cylindrical guide opening therein at positions spaced circumferentially of said cylindrical guide opening.

41. A maintenance station as claimed in claim 40, wherein said pressure chamber is created within said cylindrical passage by movement of said piston in one said direction therein during said suction stroke, and further comprising a connecting hole extending through said cylindrical member from said cylindrical passage therein to an exterior cylindrical surface thereof, whereby movement of said cylindrical member in one direction in said cylindrical guide opening brings said connecting hole into communication with said suction hole and moves said pressure chamber out of communication with said discharge hole, and whereby movement of said cylindrical member in an opposite direction in said cylindrical guide opening moves said connecting hole out of communication with said suction hole and brings said pressure chamber into communication with said discharge hole.

42. A maintenance station as claimed in claim 41, further comprising a connecting recess in said exterior cylindrical surface of said cylindrical member, and an atmosphere port extending through said cap holder from said cylindrical guide opening therein to the exterior, said cylindrical member being movable in said cylindrical guide opening to bring said suction hole into communication with said atmosphere port through said connecting recess.

43. A maintenance station as claimed in claim 39, further comprising a switch plate closing one end of said cylindrical guide opening and maintaining said cylindrical member therein, and said suction and discharge holes extend outwardly through said switch plate from an inner surface thereof.

44. A maintenance station as claimed in claim 43, wherein said pressure chamber is created within said cylindrical passage by movement of said piston in one said direction therein during said suction stroke, and further comprising a connecting hole extending through said cylindrical member from said cylindrical passage therein to an exterior surface thereof, whereby movement of said cylindrical member in one direction in said cylindrical guide opening brings said connecting hole into communication with said suction hole and moves said pressure chamber out of communication with said discharge hole, and whereby movement of said cylindrical member in an opposite direction in said cylindrical guide opening moves said connecting hole out of communication with said suction hole and brings said pressure chamber into communication with said discharge hole.

45. A maintenance station as claimed in claim 44, wherein said inner surface of said switch plate and said exterior surface of said cylindrical member comprise abutting planar surfaces.

46. A maintenance station as claimed in claim 44, further comprising another connecting hole extending through said cylindrical member from said cylindrical passage therein to said exterior surface thereof to be brought into communication with said discharge hole.

47. A maintenance station as claimed in claim 34, further comprising a connecting hole extending through said cap holder from said cap to an air inlet leading to the exterior, and a closure closing said air inlet when said cap caps said at least one nozzle.

48. A maintenance station as claimed in claim 47, wherein said power source comprises a cam member rotatable about an axis and having cam surfaces each having plural portions spaced different distances from said axis, and said closure is on a lever mounted pivotably on said cap holder, said lever having a cam follower engaging one of said cam surfaces such that rotation of said cam member about said axis pivots said lever to move said closure toward and away from said air inlet.

49. A maintenance station as claimed in claim 29, wherein said power source comprises a cam member rotatable in opposite directions about an axis, and said piston drive comprises a drive member rotatable about said axis with said cam member in a first said direction, and a unidirectional drive transfer device transferring rotation of said cam member in said first direction to said drive member and preventing transfer to said drive member of rotation of said cam member in a second opposite said direction.

50. A maintenance station as claimed in claim 49, wherein said piston drive further comprises an eccentric shaft on said drive member at a position eccentrically of said axis, said eccentric shaft rotatable with said drive member in said first direction in an orbit about said axis, said piston being connecting to said eccentric shaft.

51. A maintenance station as claimed in claim 49, wherein said unidirectional drive transfer device comprises a one-way clutch mounted between said cam member and said drive member.

52. A maintenance station as claimed in claim 51, wherein said unidirectional drive transfer device further comprises a plurality of cogs spaced about said drive member, and a ratchet mounted on said cam member and engageable with a said cog in said first direction of rotation of said cam member and operable to pass over said cogs upon rotation of said cam member in said second direction.

53. A maintenance station as claimed in claim 49, wherein said unidirectional drive transfer device comprises a plurality of cogs spaced about said drive member, and a ratchet mounted on said cam member and engageable with a said cog in said first direction of rotation of said cam member and operable to pass over said cogs upon rotation of said cam member in said second direction.

54. A maintenance station as claimed in claim 53, wherein said unidirectional drive transfer device further comprises a plate spring fixedly mounted to engage a said cog upon rotation of said drive member in said second direction.

55. A maintenance station as claimed in claim 51, wherein said unidirectional drive transfer device further comprises a drive spring having a length portion extending peripherally around said drive member and opposite ends fixed to said cam member, a fixedly positioned plate, and a control spring having a length portion extending peripherally around said drive member and opposite ends fixed to said plate.

56. A maintenance station as claimed in claim 49, wherein said unidirectional drive transfer device comprises a drive spring having a length portion extending peripherally around said drive member and opposite ends fixed to said cam member, a fixedly positioned plate, and a control spring having a length portion extending peripherally around said drive member and opposite ends fixed to said plate.

57. A pump to be employed in a maintenance station of an ink jet printer, said pump comprising:

a casing having therein a cylindrical guide opening having a first axis, and suction and discharge ports leading from said cylindrical guide opening;

a cylindrical member mounted in said cylindrical guide opening and rotatable therein in opposite directions about said first axis, said cylindrical member having therethrough a cylindrical passage having a second axis;

a piston extending into said cylindrical passage and defining therein a pressure chamber; and said piston being movable in said cylindrical passage in opposite directions along said second axis, thereby performing suction and compression strokes, and said piston being pivotable in opposite directions transverse to said second axis and thereby reciprocally rotating said cylindrical member in said opposite directions about said first axis.

58. A pump as claimed in claim 57, wherein said pressure chamber is connected to said suction port during said suction stroke and to said discharge port during said compression stroke.

59. A pump as claimed in claim 57, wherein said suction and discharge ports extend outwardly through said casing from said cylindrical guide opening therein at positions spaced circumferentially of said cylindrical guide opening.

60. A pump as claimed in claim 57, further comprising a connecting hole extending through said cylindrical member from said cylindrical passage therein to an exterior cylindrical surface thereof, whereby movement of said cylindrical member in one direction in said cylindrical guide opening brings said connecting hole into communication with said suction port and moves said pressure chamber out of communication with said discharge port, and whereby movement of said cylindrical member in an opposite direction in said cylindrical guide opening moves said connecting hole out of communication with said suction port and brings said pressure chamber into communication with said discharge port.

61. A pump as claimed in claim 60, further comprising a connecting recess in said exterior cylindrical surface of said cylindrical member, and an atmosphere port extending through said casing from said cylindrical guide opening therein to the exterior, said cylindrical member being movable in said cylindrical guide opening to bring said suction port into communication with said atmosphere port through said connecting recess.

62. A pump as claimed in claim 57, further comprising a switch plate closing one end of said cylindrical guide opening and maintaining said cylindrical member therein, and said suction and discharge ports extending outwardly through said switch plate from an inner surface thereof.

63. A method of operating a maintenance station to perform a maintenance recovery operation on an ink jet head of an ink jet printer, said maintenance station including a cap to achieve capping of at least one nozzle hole of said ink jet head, a cap holder mounted for movement toward and away from said ink jet head, said cap holder supporting said cap at a position to cap said at least one nozzle hole when said cap holder is moved toward said ink jet head and to release capping when said cap holder is moved away from said ink jet head, a pump within said cap holder and including a cylindrical guide opening formed in said cap holder, a cylindrical member mounted in said cylindrical guide opening, said cylindrical member having therethrough a cylindrical passage defining a pressure chamber, and a piston slidable in opposite directions within said cylindrical passage for suction and compression strokes of said pump, separate suction and discharge holes in said pump, a power source, and a piston drive operably connected to said power source and to said piston to move said piston in said opposite directions in said cylindrical passage to connect said pressure chamber in said cylindrical passage via said suction hole to said cap during said suction stroke, and to connect said pressure chamber via said discharge hole to the exterior during said compression stroke, said method comprising:

moving said cap holder toward said ink jet head to a capping position with said cap capping said at least one nozzle hole;

conducting said suction stroke with said cad holder in said capping position, and thereby drawing residual ink from said ink jet head into said pressure chamber through said suction hole;

conducting said compression stroke with said cap holder in said capping position, and thereby discharging said residual ink from said pressure chamber through said discharge hole to the exterior;

moving said cap holder away from said ink jet head to an intermediate position with a gap between said cap and said ink jet head;

conducting said suction stroke with said cap holder at said intermediate position, and thereby drawing air from said gap and ink from the surface of said at lest one nozzle hole into said pressure chamber through said suction hole;

conducting said compression stroke with said cap holder in said intermediate position, and thereby discharging said air and ink from said pressure chamber through said discharge hole to the exterior; and moving said cap holder further away from said ink jet head to a withdrawn position whereat said cap is spaced further away from said ink jet head.

64. A method as claimed in claim 63, wherein said power source comprises a cam member rotatable about an axis and having a cam surface having plural portions spaced different distances from said axis, and said cap holder is moved toward and away from said ink jet head by engaging a cam follower on said cap holder with said cam surface such that rotation of said cam member about said axis moves said cap holder toward and away from said ink jet head.

65. A method as claimed in claim 64, wherein said piston drive comprises an eccentric member positioned eccentrically of said axis and rotatable in an orbit thereabout, a first end of said piston extends into said cylindrical passage in said cylindrical member, and a second end of said piston is connected to said eccentric member and is rotatable in said orbit therewith, as a result of which said first end of said piston moves in said opposite directions in said cylindrical passage in said cylindrical member and said cylindrical member reciprocally rotates in opposite directions within said cylindrical guide opening in said cap holder.

66. A method as claimed in claim 65, comprising rotating said eccentric member in said orbit about said axis during rotation of said cam member in a first direction about said axis, and selectively rotating said cam member in an opposite second direction about said axis while preventing rotation of said eccentric member about said axis.

* * * * *